United States Patent
Chibber et al.

(10) Patent No.: US 8,197,794 B2
(45) Date of Patent: Jun. 12, 2012

(54) CORE 2 GLCNAC-T INHIBITORS

(75) Inventors: Rakesh Chibber, Exeter (GB); Russell Hagan, London (GB)

(73) Assignee: MS Therapeutics Limited, Crowthorne, Berkshire (GB)

( * ) Notice: Subject to any disclaimer, the term of this patent is extended or adjusted under 35 U.S.C. 154(b) by 214 days.

(21) Appl. No.: 12/461,776

(22) Filed: Aug. 24, 2009

(65) Prior Publication Data

US 2010/0256077 A1    Oct. 7, 2010

Related U.S. Application Data

(63) Continuation of application No. 11/980,727, filed on Oct. 31, 2007, now abandoned, which is a continuation-in-part of application No. 10/584,470, filed on Aug. 9, 2006, now Pat. No. 7,906,493, and a continuation-in-part of application No. 11/481,256, filed on Jul. 6, 2006, and a continuation-in-part of application No. 11/481,255, filed on Jul. 6, 2006, and a continuation-in-part of application No. 11/472,554, filed on Jun. 22, 2006.

(30) Foreign Application Priority Data

Dec. 22, 2003  (GB) .................................. 0329667.0
Dec. 22, 2004  (WO) ................ PCT/GB2004/005398

(51) Int. Cl.
   *A61K 49/00*   (2006.01)
(52) U.S. Cl. .......................................... 424/9.1; 514/23
(58) Field of Classification Search .................. None
   See application file for complete search history.

(56) References Cited

U.S. PATENT DOCUMENTS

| | | |
|---|---|---|
| 4,602,003 A | 7/1986 | Malinow |
| 5,104,856 A | 4/1992 | Esko et al. |
| 5,360,733 A | 11/1994 | Fukuda et al. |
| 5,461,143 A | 10/1995 | Wong et al. |
| 5,470,879 A | 11/1995 | Sauvaire et al. |
| 5,486,510 A | 1/1996 | Bouic et al. |
| 5,589,182 A | 12/1996 | Tashiro et al. |
| 5,624,832 A | 4/1997 | Fukuda et al. |
| 5,658,778 A | 8/1997 | Fukuda et al. |
| 5,684,134 A | 11/1997 | Fukuda et al. |
| 5,827,884 A | 10/1998 | Obagi |
| 5,843,707 A | 12/1998 | Larsen et al. |
| 5,880,091 A | 3/1999 | Cummings et al. |
| 5,886,029 A | 3/1999 | Dhaliwal |
| 5,952,393 A | 9/1999 | Sorkin, Jr. |
| 5,958,770 A | 9/1999 | Cham et al. |
| 5,965,449 A | 10/1999 | Novak |
| 5,985,936 A | 11/1999 | Novak |
| 5,997,877 A | 12/1999 | Chang |
| 6,042,834 A | 3/2000 | Baraka |
| 6,087,353 A | 7/2000 | Stewart et al. |
| 6,131,578 A | 10/2000 | King et al. |
| 6,197,832 B1 | 3/2001 | Sorkin, Jr. |
| 6,294,157 B1 | 9/2001 | Rubinstenn et al. |
| 6,346,267 B1 | 2/2002 | Fry et al. |
| 6,383,514 B1 | 5/2002 | Weitkemper et al. |
| 6,407,085 B1 | 6/2002 | Kief |
| 6,451,355 B1 | 9/2002 | Reisner |
| 6,593,301 B1 | 7/2003 | Ma et al. |
| 6,635,461 B1 | 10/2003 | Schwientek et al. |
| 6,787,151 B2 | 9/2004 | Meijer et al. |
| 6,933,291 B2 | 8/2005 | Qi et al. |
| 6,998,501 B1 | 2/2006 | Wright et al. |
| 2002/0016314 A1 | 2/2002 | Schersi |
| 2002/0018811 A1 | 2/2002 | Penteado et al. |
| 2002/0098563 A1 | 7/2002 | Korczak et al. |
| 2002/0107292 A1 | 8/2002 | Bortlik et al. |
| 2002/0156051 A1 | 10/2002 | Kutney et al. |
| 2002/0183294 A1 | 12/2002 | Barraclough et al. |

(Continued)

FOREIGN PATENT DOCUMENTS

CA    2 186987    4/1998

(Continued)

OTHER PUBLICATIONS

Mimaki et al. Phytochemistry (1996), vol. 42, pp. 1065-1070.*
Milgate et al. Nutrition Research (1995), vol. 15, pp. 1223-1249.*
Zheng et al. Steroids (2004), vol. 69, pp. 111-119.*
Hu et al. Planta Medica (1997), vol. 63, pp. 161-165.*
Yang et al. Journal of Food and Drug Analysis (2003), vol. 11, pp. 271-276.*
Guo et al. Analytica Chimica Acta (2001), vol. 436, pp. 41-47.*
Derwent Publications Ltd., London, GB AN 2001-412294 & JP 2001 072597 A (Mercian) Corp; Mar. 21, 2001; (abstract).

(Continued)

*Primary Examiner* — Patrick Lewis
(74) *Attorney, Agent, or Firm* — Brown Rudnick LLP; Thomas Meyers

(57) ABSTRACT

Treatments for conditions involving detrimental activity of the enzyme core 2 GlcNAc-T are provided using compounds of the formula I

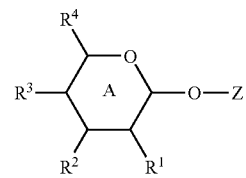

wherein
  $R^1$ is H, —OH, $C_{1-6}$ alkoxy, —$NR^5R^6$, or Sac 1;
  $R^2$ is H, —OH, $C_{1-6}$ alkoxy or Sac 2;
  $R^3$ is H, —OH, $C_{1-6}$ alkoxy or Sac 3;
  $R^4$ is H, $C_{1-6}$ alkyl, $C_{1-6}$ hydroxyalkyl or $C_{1-6}$-alkoxy-$C_{1-6}$-alkyl;
  $R^5$ is H, $C_{1-6}$ alkyl or $C_{1-6}$ acyl;
  $R^6$ is H, $C_{1-6}$ alkyl or $C_{1-6}$ acyl;
  Sac 1 Sac 2 and Sac 3 are independently selected saccharide moieties; and
  Z is a steroid moiety;
or a pharmaceutically acceptable salt, ether or ester form thereof.

5 Claims, 21 Drawing Sheets

U.S. PATENT DOCUMENTS

| | | | |
|---|---|---|---|
| 2002/0193317 A1 | 12/2002 | Xia et al. |
| 2003/0004147 A1 | 1/2003 | Barraclough et al. |
| 2003/0096316 A1 | 5/2003 | Wester |
| 2003/0148962 A1 | 8/2003 | Guan et al. |
| 2004/0033521 A1 | 2/2004 | Korczak et al. |
| 2004/0038923 A1 | 2/2004 | Marth et al. |
| 2004/0049352 A1 | 3/2004 | Andre et al. |
| 2004/0203111 A1 | 10/2004 | Schwientek et al. |
| 2004/0220115 A1 | 11/2004 | Cham |
| 2004/0249138 A1 | 12/2004 | Lawson |
| 2006/0052351 A1 | 3/2006 | Platt et al. |
| 2007/0254847 A1 | 11/2007 | Liu et al. |

FOREIGN PATENT DOCUMENTS

| | | |
|---|---|---|
| CA | 2186987 | 4/1998 |
| CA | 2 335 436 | 8/2001 |
| CN | 1 237 583 A | 12/1999 |
| CN | 1237583 A | 12/1999 |
| CN | 1243129 A | 2/2000 |
| CN | 1361111 A | 12/2000 |
| CN | 1361111 A | 7/2002 |
| CN | 1 397 545 | 2/2003 |
| CN | 1 511 535 | 7/2004 |
| CN | 1 562 064 A | 1/2005 |
| CN | ZL 00135190.7 | 1/2005 |
| DE | 4303214 A1 | 11/1994 |
| EP | 0 251 197 | 1/1988 |
| EP | 0 251 197 A2 | 1/1988 |
| EP | 0 251 197 A3 | 1/1988 |
| EP | 1 316 608 A1 | 6/2003 |
| EP | 0 850 243 B1 | 10/2003 |
| EP | 1 800 685 A1 | 6/2007 |
| JP | 03271224 A | 3/1991 |
| JP | 2004-143126 | 5/2004 |
| RU | 2 027 434 C1 | 1/1995 |
| RU | 2027434 | 1/1995 |
| SU | 833254 | 5/1981 |
| WO | WO 95/17182 A1 | 6/1995 |
| WO | WO 95/21199 A1 | 8/1995 |
| WO | WO 95/35294 A1 | 12/1995 |
| WO | WO 97/06176 A2 | 2/1997 |
| WO | WO 97/47298 A1 | 12/1997 |
| WO | WO 98/06405 A1 | 2/1998 |
| WO | 98/14459 | 4/1998 |
| WO | WO 98/33494 | 8/1998 |
| WO | WO 98/33494 A1 | 8/1998 |
| WO | WO 99/25197 | 5/1999 |
| WO | WO 99/25197 A1 | 5/1999 |
| WO | WO 99/39715 A1 | 8/1999 |
| WO | WO 99/53925 A1 | 10/1999 |
| WO | WO 00/31109 | 6/2000 |
| WO | WO 00/31109 A1 | 6/2000 |
| WO | WO 00/52029 A1 | 9/2000 |
| WO | WO 00/61153 | 10/2000 |
| WO | WO 00/78789 A1 | 12/2000 |
| WO | WO 01/32679 A2 | 5/2001 |
| WO | 01/58932 | 8/2001 |
| WO | WO 01/83717 A2 | 11/2001 |
| WO | WO 02/87548 | 11/2001 |
| WO | WO 02/03996 A1 | 1/2002 |
| WO | WO 02/24212 A1 | 3/2002 |
| WO | WO 02/069980 A2 | 9/2002 |
| WO | WO 02/087548 A1 | 11/2002 |
| WO | 03/043433 | 5/2003 |
| WO | 03/066679 | 8/2003 |
| WO | WO 03/070261 A1 | 8/2003 |
| WO | WO 03/075931 A1 | 9/2003 |
| WO | 03/092394 | 11/2003 |
| WO | WO 2004/002497 A1 | 1/2004 |
| WO | WO 2004/019960 A2 | 3/2004 |
| WO | WO 2004/029068 A1 | 4/2004 |
| WO | WO 2004/048938 A2 | 6/2004 |
| WO | WO 2004/062675 A1 | 7/2004 |
| WO | WO 2004/064852 A1 | 8/2004 |
| WO | 2004/074461 | 9/2004 |
| WO | WO 2004/093662 A2 | 11/2004 |
| WO | WO 2004/111196 A2 | 12/2004 |
| WO | WO 2005/060977 A1 | 7/2005 |
| WO | WO 2005/084323 A2 | 9/2005 |
| WO | WO 2005/120535 A1 | 12/2005 |
| WO | 2006/034655 | 4/2006 |
| WO | WO 2006/034655 A1 | 4/2006 |
| WO | WO 2006/034655 A1 | 6/2006 |

OTHER PUBLICATIONS

Belozerskaya V, et al, Effect of steroid glycosides on *Neurospora crassa* Membranes; Applied Biochemistry and Microbiology, vol. 30, No. 6 1994 pp. 724-728.

Brockhausen I et al; The separation of liquid chromatography (under elevated pressure) of phenyl, benzyl, and $_o$-nitrophenyl glycosides of oligosaccharides. Analysis of substrates and products for four $N$-acetyl$_D$-Glucosaminyl-transferases involved in mucin synthesis; Carbohydrate Research, 120(1983) pp. 3-16.

Brower Thomas D et al; Rheumatoid Arthritis; Journal of the Kentucky Medical Association, May 1983, pp. 281-286.

Chiang HC et al Xanthine Oxidase Inhibitors from the Roots of Eggplant (*Solanum melongena* L), J. Enzyme Inhibition 1993, vol. 7, pp. 225-235.

Deepak M et al., Quantitative Determination of the Major Saponin Mixture Bacoside A in *Bacopa monnieri* by HPLC; Phytochemical Analysis 16, pp. 24-29 )2005).

Djerassi C et al., J. Biol Chem. Jan. 1952; 194(1) 115-8.

Eisenreichova E et al ., A new steroidal saponin from the bulbs of *Lilium candidum* ., Pharmazie (2000) 55 (7) pp. 549-550.

Faul William h et al., Side-chain Transformations and Deuterium Labeling in the Steroidal Sapogenin Series., J. Org. Chem. vol. 35, No. 8, 1970 pp. 2571-2585.

Gautam et al ., Immunomodulatory activity of *Asparagus racemosus* on systemic Th1/Th2 immunity, Implications for immuno adjuvant potential. J. ethnopharmacology, 121, 241-247 (2009).

Girardon P et al., Volatile Constituents of Fenugreek Seeds, Planta Medica 1985, pp. 533-534.

Hayes PY., et al, Structural revision of shatavarins I and IV, the major components from the roots of *Asparagus racemosus*, Tetrahedron Letters 47 (2006) 6965-6969.

Hosny M et al., Balanitoside, A furostanol Glycoside, and 6-Methyl-Diosgenin from *Balanites Aegyptiaca*, Phytochemistry, vol. 31, No. 10 pp. 3565-3569.

Hostettmann K et a.l Saponins. Cambridge University Press UK. (1995).

Hou C et al., Bacopaside III, Bacopasaponin G, and Bacopasides A, B, and C from *Bacopa monniera*, J. Nat. Prod 2002, 65 1759-1763.

Hu K et al., Protodioscin (NSC-698 796) Its Spectrum of Cytotoxicity Against Sixty Human Cancer Cell Lines in an Anticancer Drug Screen Panel, Planta Med 2002; 68: 297-301.

Hu K et al., The cytotoxicity of protoneodioscin (NSC-698789), a furostanol saponin from the rhizomes of *Dioscorea collettii* var. *hypoglauca*, against human cancer cells in vitro, Phytomedicine 9: 560-565, 2002.

Hu K et al., The Cytotoxicity of Methyl Protoneodioscin (NSC-698791) Against Human Cancer Cell Lines In Vitro: Anticancer Research 22: 1001-1006 (2002).

Hu K et al., Antineoplastic Agents; 1. Three Spirostanol Glycosides from Rhizomes of *Dioscorea collettii* var. *hypoglauca*: Planta Medica 62 (1996) 573-575.

Inamdar AC et al., Comparison between Shatavar and *Asparagus* Spp.: Bioyigyanam 6: 27-35, 1980.

Inoue T et al., Steroidal Glycosides from *Allium macleanii* and *A. senescens*, and their inhibitory activity on tumour promoter-induced phospholipid Metabolism of Hela Cells: Phytochemistry vol. 40, No. 2, pp. 521-525 (1995).

Jin M et al., Cytotoxic Steroidal Saponins from *Polygonatum zanlanscianense*, J. Nat. Prod. , 67, 1992-1995. (2004).

Joussen Am et al., Nonsteroidal anti-inflammatory drugs prevent early diabetic retinopathy via TNF-α suppression: The FASAB Journal, Mar. 2002, vol. 16 pp. 438-440.

Kostova I et al., Two new sulfated Furostanol Saponins from *Tribulus terrestris*: Z Naturforsch, 57c, pp. 33-38 (2002).

Li M et al., Synthesis of monomethylated dioscin derivatives and their antitumor activities: Carbohydrate Research 338 (2003) 117-121.

Liu M et al., Synthesis of (25R)-ruscogenin-1-yl β-D-xylopyranosyl-(1→3)-[β-D-glucopyranosyl-(1→2)]-β-D-fucopyranoside: Carbohydrate Research 329 (2000) 745-754.

Liu H et al., New Furostanol Glycosides from the Rhizomes of *Dioscorea futschauensis* R. Kunth:Journal of Asian Natural Products Research 2003, vol. 5 (4) pp. 241-247.

Liu M et al., Diosgenin induces cell cycle arrest and apoptosis in human leukemia K562 cells with the disruption of $Ca^{2+}$ homeostasis: Cancer Chemother Pharmacol (2005) 55: 79-90.

Madar Z et al., Fenugreek (*Trigonella foenumgraecum*) as a means of reducing postprandial glucose level in diabetic rats: Nutrition Reports International Jun. 1984, vol. 29, No. 6, pp. 1267-1273.

Mahato Sb et al., Bacopasaponins E and F: two jujubogenin bisdesmosides from *Bacopa monniera*: Phytochemistry 53 (2000) 711-714.

Markine-Goriaynoff N. et al., The core 2 β-1, 6-N-acetylglucosaminyltransferase-M encoded by bovine herpesvirus 4 is not essential for virus replication despite contributing to post-translational modifications of structural proteins: Journal of General Virology (2004) 85, 355-367.

Melo PS et al., Cytotoxicity of phytosterol diosgenin and its derivatives in rat cultured hepatocytes and V79 fibroblasts: Human & Experimental Toxicology (2004) 23, 487-493.

Nakamura T et al., Interaction of Saponins with red blood cells as well as with the phosphatidylcholine liposomal membranes; J> Pharm Dyn. 2, 374-382 (1979).

Nian H et al., Protective effect of steroidal saponins from rhizome of *Anemarrhena asphodeloides* on ovarietomy-induced bone loss in rats; Acta Pharmacologica Sinica Jun. 27, 2006: (6) pp. 728 734.

Paseshnichenko Va et al., Isolation and Properties of Saponins from dioscorea deltoidea Rhizomes; Applied Biochem. Microbiol. 1975, II (1) p. 83-90.

Pawar R et al., Dammarane Triterpene Saponin from *Bacopa monniera* as the Superoxide inhibitor in Polymorphonuclear Cells; Planta Med 67 (2001) pp. 752-754.

Quan HJ et al., Preparations of heterospirostanols and their pharmacological activities; Eur. J Med. Chem 37 (2002) pp. 659-669.

Raju J et al., *Trigonella foenum graecum* (fenugreek) seed powder improves glucose homeostasis in alloxan diabetic rat tissues by reversing the altered glycolytic, gluconeogenic and lipogenic enzymes; Molecular and Cellular Biochemistry 224: 45-51, 2001.

Ribes G et al., Effects of Fenugreek Seeds on Endocrine Pancreatic Secretions in Dogs; Ann Nutr Metab 28: 37-43 (1984).

Shao Y et al., Anti-tumor activity of the crude saponins obtained from asparagus; Cancer Letters 104 (1996), 31-36.

Shao Y et al.,Steroidal Saponins from *Asparagus officinalis* and Their Cytotoxic Activity; Planta Medica 63 (1997) 258-262.

Sharma Rd; Effect of Fenugreek Seeds and Leaves on Blood Glucose and Serum Insulin Responses in Human Subjects; Nutrition Research, vol. 6, pp. 1353-1364 (1986).

Sharma Sc et al; Steroidal Saponins of *Asparagus adscendens*; Phytochemistry, vol. 21, No. 8, pp. 2075-2078 (1982).

Shimomura H et al; 26-O-Acylated Furostanol Saponins Pardarinoside A and B from the Bulbs of *Lilium pardarinum*; Chem. Pharm. Bull. 36 (8) 3226-3229, 1988.

Sheilds et al Acute Multiple Sclerosis, characterized by extensive mononuclear phagocyte infiltration. Neurochem. res. 25, 1517-1520. (2000).

Singh SB et al., Furostanol Saponins from *Paris polyphylla* Structures of Polyphyllin G and H; Phytochemistry, vol. 21, No. 8, pp. 2079-2082, 1982.

Sinha J et al; Bacopasaponin C: Critical Evaluation of Anti-Leishmanial Properties in Various Delivery Modes; Drug Delivery, 9: 55-62, 2002.

Sur P et al; *Trigonella Foenum graecum* (Fenugreek) Seed Extract as an Antineoplastic Agent; Phytotherapy Research, 15 257-259 (2001).

Spruce et al (2004) Intrinsic factors implicated in the sequence of diabetic neuropathy and foot ulceration: a potential role of core2 betal, 6-N-acetylglucoseaminyltransferase (core2GlcNAcT-I) [core 2 transferase]. *Diabetic Medicine*, 21 (Suppl. 2), 1-35.

Vachalkova A et al., Potential carcinogenic and inhibitory activity of compounds isolatyed from *Lilium candidum* L; Neoplasma, 47, 5, 2000 pp. 313-318.

Vasileva.,. Composition and Biological Activity of Steroidal Glycosides from cell suspensions of *Dioscorea deltoidea* Wall. Prikl Biokhim Mikrobiol 1995, vol. 31 (2) pp. 238-242. English Abstract.

Vasileva, Isolation and properties of Saponins from Dioscorea deltoidea Wall Rhizomes. Prikl Biokhim Mikrob, 1975, II (1), p. 94-101—English Abstract.

Van Der Elst I and Datti A. β1,6 N-Acetylglucosaminyltransferase (core 2 GlcNAc-T) expression in normal rat tissues and different cell lines: evidence for complex mechanisms of regulation. Glycobiology vol. 8 No. 7 pp. 731-740, (1998).

Vasileva, Composition and Biological Activity of Steroid Glycosides from Cell Suspensions of *Discorea deltoidea* Wall; Applied Biochemistry and Microbiology, vol. 31, No. 2 1995, pp. 206-209.

Vasyukova NI., Fungitoxic Properties of Steroid Saponins from *Dioscorea deltodea* Rhizomes; Applied Biochem Microbol. 1977, 13 (2) pp. 128-131.

Yu J et al., Progress in studies on chemical constituents and pharmacological effect of Trigonella foenum-graecum. Chinese traditional and Herbal Drugs, 34(12) 1146-1149 (2003).

Li C et al., Synthesis of diosgenyl α-L rhamnopyranosyl-(1→2)-[D-glucopyrampsyl-{1→3)]-β-D-glucopyranoside {gracillin} amd related saponins;Carbohydrate Research 306 (1998) p. 189-195.

Yu B et al., First Synthesis of a Bidesmosidic Triterpene Saponin by a Highly Efficient Procedure; J.AM.Chem.Soc. 1999, 121, pp. 12196-12197.

Zou CC et al., The synthesis of gracillin and dioscin: two typical representatives of spirostanol glycosides; Carbohydrate Research 338 (2003) pp. 721-727.

Davies, M. J., et al; "The Expression of the Adhesion Molecules Icam-1, Vcam-1, Pecam, and E-Selectin in Human Atherosclerosis", *Journal of Pathology*, vol. 171: 223-239 (1993).

Ke, H. et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Yu, J. et al, "Progress in studies on chemical constituents and pharmacological effect of *Trigonella foenum-graecum*"; *Chinese Traditional and Herbal Drugs*, vol. 34, (12) 1146-1149 (2003).

Battistini, L. et al; "CD8+ T cells from patients with acute multiple sclerosis display selective increase of adhesiveness in brain venules: a critical role for P-selectin glycoprotein ligand-1", *Blood*, vol. 101 No. 12, 4775-4780 (2003).

Ben-Mahmud, Bahaedin M., et al; "Tumor Necrosis Factor-αin Diabetic Plasma Increases the Activity of Core 2 GLcNAc-T and Adherence of Human Leukocytes to Retinal Endothelial Cells"; *Diabetes*, vol. 53, 2968-2976 (2004).

Brockhausen, I., et al; "Biosynthesis of O-Glycans in Leukocytes from Normal Donors and from Patients with Leukemia: Increase in O-Glycan Core 2 UDP-GlcNAc:Galβ1-3GalNAc-R (GlcNAc to GalNAc) β(1-6)-N-Acetylglucosaminyltransferase in Leukemic Cells"; *Cancer Research*; 51, 1257-1263 (1991).

Buerke, Michael, et al; "Sialyl Lewis$^x$-Containing Oligosaccharide Attenuates Myocardial Reperfusion Injury in Cats"; *J. Clin. Invest.*; vol. 93, 1140-1148 (1994).

Beum, P.V. and Cheng, Pi-W.; "Biosynthesis and Function of β1,6 Branched Mucin-Type Glycans"; *The Molecular Immunology of Complex Carbohydrates-2* (2001).

Beum, P.V., et al; "Mucin biosynthesis: upregulation of core 2 β1,6 N-acetylglucosaminyltransferase by retinoic acid and Th2 cytokines in a human airway epithelial cell line"; *Am J. Physiol Lung Cell Mol Physiol.*; 288: L116-L124 (2005).

Beum, P.V. et al; "Mucin Biosynthesis Epidermal Growth Factor Downregulates Core 2 Enzymes in a Human Airway Adenocarcinoma Cell Line"; *Am. J. Respir. Cell Mol. Biol.*; vol. 29, 48-56 (2003).

Celie, J.W.A.M., et al; "Identification of L-Selectin Binding Heparan Sulfates Attached to Collagen Type XVIII"; *J. Biol Chem.*; 280(29); 26965-73; Epub (2005).

Davies, Michael J., et al; "The Expression of the Adhesion Molecules Icam-1, Vcam-1, Pecam, and E-Selectin in Human Atherosclerosis", *Journal of Pathology*, vol. 171: 223-239 (1993).

Dennis, James W.; "Glyco-Forum Section; Core 2 GlcNAc-Transferase and polylactosamine expression in O-glycans", *Glycobiology*; vol. 3, No. 2, pp. 91-96 (1993).

Dube, Danielle H. et al, "Glycans in Cancer and Inflammation—Potential for Therapeutics and Diagnostics", *Nature Reviews*, vol. 4, No. 6, 477-288 (2005).

Duan L-L. et al; "Regulation of Metastasis-Suppressive Gene Nm23-H1 on Glycosy-transferases Involved in the Synthesis of Sialy Lewis Antigens"; *J. Cell. Biochem.*; 94:1248-1257 (2005).

Fox, R.I., et al; "A Novel Cell Surface Antigen (T305) Found in Increased Fequency on Acute Leukemia Cells and in Autommune Disease States"; *J. Immunol.* vol. 131, No. 2, 761-767 (1983).

Foxall, C. et al; "The Three Members of the Selectin Receptor Family Recognize a Common Carbohydrate Epitope, the Sialyl Lewis[x] Oligosaccharide"; *J. Cell Biol.*; vol. 117, 895-902 (1992).

Fugang P. et al.; "Post Translational Modifications of Recombinant P-selectin Glycoprotein Ligand-1 Required for Binding to P and E-selectin"; *J. Biol. Chem.*; vol. 271, No. 6, 3255-3264 (1996).

Fujita, M. et al; "Pulmonary hypertension in TNF-α-overexpressing mice is associated with decreased VEGF gene expression"; *J. Applied Physiol*; vol. 93, 2162-2170 (2002).

Goss, P. E. et al; "Inhibitors of Carbohydrate Processing: A New Class of Anticancer Agents[1,2]"; *Clin. Cancer Res.*; vol. 1, 935-944 (1995).

Maaheimo, Hannu et al, "Synthesis of a divalent sialyl Lewis x O-glycan, a potent inhibitor of lymphocyte-endothelium adhesion"; *Eur J. Biochem*; 234, 616-625 (1995).

Hiraoka, N. et al; "Core 2 Branching β1,6-N-Acetylglucosaminyltransferase and High Endothelial Venule-restricted Sulfotransferase Collaboratively Control Lymphocyte Homing"; *J. Biol Chem.*; vol. 279, No. 4, 3058-3067 (2004).

Ke, Hu et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res.*; 17; 620-626 (2003).

Kumar, A. et al; "Recombinant Soluble Form of PSGL-1 Accelerates Thrombolysis and Prevents reocclusion in a Porcine Model"; *Circulation*; 99, 1363-1369 (1999).

Jain, Rakesh K. et al, "Inhibition of L-and P-selectin by a rationally synthesized novel core 2-like branched structure containing GalNAc-Lewis[x] and Neu5Acα2-3Galβ-3GalNAc sequences"; *Glycobiology*, vol. 8, No. 7; 707-717 (1998).

Jones, Steven P., "A Bittersweet Modification O-GlcNAc and Cardiac Dysfunction"; *Circ Res.*; 96; 925-926 (2005).

Kamisako, Toshinori et al, "Regulation of biliary cholesterol secretion is associated with abcg5 and abcg8 expressions in the rats: effects of diosgenin and ethinyl estradiol", *Hepatology Research* 26; 348-352 (2003).

Lewis, M.J. and D 'Cruz D.; "Adhesion molecules, mycophenolate mofetil and systemic lupus erythematosus"; *Lupus*, 14, 17-26 (2005).

Martininez, M. et al; "Regulation of PSGL-1 Interactions with L-selectin, P-selectin, and E-selectin"; *J. Biol. Chem.*, vol. 280, No. 7, 5378-5390 (2005.).

Merzaban, Jasmeen S. et al.; "An Alternate Core 2 β,6-N-Acetylglucosaminyltransferase Selectively Contributes to P-Selectin Ligand Formation in Activated CD8 T Cells[1]"; *The Journal of Immunology*, 174: 4051-4059 (2005).

Morin, M.J. and Bernacki, R.J.; "Biochemical Effects and Therapeutic Potential of Tunicamycin in Murine L1210 Leukemia"; *Cancer Res.* 43, 1669-1674 (1983).

Nakamura, M. et al.; "Single Glycosyltransferase, Core 2β1-6-N-acetylglucosaminyltransferase, Regulates Cell Surface Sialy-Le[x] Expression Level in Human Pre-B Lymphocytic Leukemia Cell Line KM3 Treated with Phorbolester"; *J. Biol. Chem.*; 273, No. 41; 26779-26789 (1998).

Narumi, S. et al; "Tissue-Specific Induction of E-Selectin in Glomeruli is Augmented following Diabetes mellitus"; *Nephron*; 89, 161-171 (2000).

Okada, S. et al; "Intercellular Adhesion Molecule-1—Deficient Mice are Resistant Against Renal Injury After Induction of Diabetes"; *Diabetes*; 52:2586-2593 (2003).

Piccio L. et al; "Molecular Mechanisms Involved in Lymphocyte Recruitment in Inflamed Brain Microvessels: Critical Roles for P-Selectin Glycoprotein Ligand-1 and Heterotrimeric $G_i$-Linked Receptors[1]"; *J. Immunol.*; 168: 1940-1949 (2002).

Ravnskov, U; "Is atherosclerosis caused by high cholesterol?", *Q J Med*; 95, 397-403 (2002).

Ross, Russell; "Atherosclerosis—An Inflammatory Disease", *The New England Journal of Medicine*, vol. 340, 2, 115-126 (1999).

Simmons, Rex D. and Brenda A. Cattle; "Sialyl Ligands facilitate lymphocyte accumulation during inflammation of the central nervous system", *Journal of Neuroimmunology*, 41; 123-130 (1992).

Steinberg, D.; "Atherogenesis in perspective: Hypercholesterolemia and inflammation as partners in crime"; *Nature Medicine*; vol. 8, No. 11; 1211-1217 (2002).

Steinman, Lawrence; "Blocking Adhesion Molecules as Therapy for Multiple Sclerosis: Natalizumab"; *Nature Reviews: Drug Discovery*, vol. 4, 510-518 (2005).

Baek, Suk Hwan, et al, "Inactivation of Human Pleural Fluid Phospholipase $A_2$ by Dioscin"; *Arch. Pharm. Res.*; vol. 17, No. 4, 218-222 (1994).

Ulbrich, Holger, et al; "Leukocyte and endothelial cell adhesion molecules as targets for therapeutic interventions in inflammatory disease"; *Trends in Pharmacological Sciences*, vol. 24, No. 12; 640-647 (2003).

Williams, D. et al; "Mucin Synthesis II. Substrate Specificity and Product Identification Studies on Canine Submaxillary Gland UDP-GlcNAc:Galβ1-3GalNAc(GlcNAc—GalNAc) β6-N-acetylglucosaminyltransferase"; *J. Biol. Chem.*; 255, No. 23; 1253-1261 (1980).

Yanagihara, K., et al; "Lipopolysaccharide Induces Mucus Cell Metaplasia in Mouse Lung"; *Am. J. Respir. Cell Mol. Biol.*; 24, 66-73 (2001).

Yu, Jing et al, "Progress in studies on chemical constituents and pharmacological effect of *Trigonella foenum-graecum*"; *Chinese Traditional and Herbal Drugs*, vol. 34, (12) 1146-1149 (2003).

Zak, I., et al; "Selectin Glycoprotein Ligands"; *Acta Biochemica Polonica*; vol. 47, No. 2; 393-412 (2000).

Droogan A G et al "Serum and cerebrospinal fluid levels of solube adhesion molecules in multiple sclerosis: predominant intrathecal release of vascular cell adhesion molecule-1"; Journal of Neuroimmunology 64 (1996) 185-191.

Shinya Hanashima et al "Systematic Synthesis of Bisubstrate-Type Inhibitors of N-Acetylglucosaminyltransferases" Chem. Eur. J. 2006, 12, 3449-3462.

Mohamed S Kamel et al, "Studies on Balanites aegyptiaca Fruits, an Antidiabetic Egyptian Folk Medicine"; Chemical & Pharmaceutica Bulletin 1991, 39(5), 1229-1233.

Takao Konoshima et al "Anti-Aids Agents, 21 Triterpenoid saponins as anti-HIV principles from fruits of gleditsia Japonica and gymnocladus chinesis and a structure-activity correlation"; Journ of Nat. Prods. vol. 58, No. 9, pp. 1372-1377, Sep. 1995.

Laurence A Lasky, "Selectin-Carbohydrate interactions and the initiation of the inflammatory response", Annual Review of Biochemistry 1995 vol. 64, pp. 113-139.

Daniel Lazarevia et al; "Artificial N-functionalised UDP-glucosamine analogues as modified substrates for N-acetylglycosaminyl transferases" Carbohydrate Research 2006, vol. 341(5), 569-576.

Hiromichi Matsuura; "Saponins in Garlic as Modifiers of the Risk of Cardiovascular Disease"; Journal of Nutrition 131, 1000S-1005S, 2001.

John G Ondeyka et al; "Discovery of structurally diverse natural product antagonists of chemokine receptor CXCR3"; Molecular Diversity (2005), 9, 123-129.

Carlo A Palmerini et al "An approach for fluorometric determination of glycosyltransferase activites", Glycoconjugate Journal (1996) 13, 631-636.

M M Vaghefi et al; "Synthesis of Glycopyranosylphosphonate Analogues of Certain Natural Nucleoside Diphosphate Sugars as Potential Inhibitors of Glycosyltransferases", Journal of Medicinal Chemistry, 1987, (30), 1383-1391.

M M Vaghefi et al, "Synthesis of certain nucleoside methylenediphosphonate sugars as potential INHIB", Journal of Medicinal Chemistry 1987, 30 1391-1399.

Co-Pending U.S. Appl. No. 10/584,470, filed Jun. 22, 2006.
Co-Pending U.S. Appl. No. 11/472,554, filed Jun. 22, 2006.
Co-Pending U.S. Appl. No. 11/481,255, filed Jul. 6, 2006.
Co-Pending U.S. Appl. No. 11/481,256, filed Jul. 6, 2006.

Rita Aquino et al, "Furostanol Oligosides from Tamus Communis", Journal of Natural Products vol. 49, No. 6, pp. 1096-1101, Nov.-Dec. 1986.

Jean-Guy Bienvenu et al, "Recombinant Soluble P-Selectin Glycoprotein Ligan-1-Ig Reduces Restenosis through Inhibition of Platelet-Neutrophil Adhesion after Double Angioplasty in Swine", Circulation. 27;103(8):1128-34 (2001).

Chen C. et al, Yunnan Zhiwu Yanjiu, 9(4), 495-502 (1987).

Chow F. et al., "Macrophages in streptozotocin-induced diabetic nephropathy: potenial role in renal fibrosis" Nephrol Dial Transplant. 19(12):2987-96 (2004).

Fujita S. et al, "Dammarane Glycosides from Aerial parts of Neoalsomitra Integrifoliola", Phytochemistry, 38(2), 465-72 (1995).

Guofeng Gu, et al, "Facile Synthesis of Saponins Containing 2,3-Branched Oligosaccharides by Using Partially Protecgted Glycosyl Donors", J. Org. Chem 2004, 69, 5497-5500.

Haladova M. et al., "Steroids saponins from the petals of Lilium candidum L.", Pharmazie, 54(2), 159-160 (1999).

Hansen A. et al., "Evaluation of Cardioprotective Effects of Recombinant Soluble P-Selectin Glycoprotein Ligan-Immunoglobulin in Myocardial Ischemia-Reperfusion Injury by Real-Time Myocardial Contrast Echocardiography" J Am Coll Cardiol. 18;44(4):887-91 (2004).

Hans-Peter Hartung et al, "Circulating Adhesion Molecules and Tumor Necrosis Factor Receptor in Multiple Sclerosis: Correlation with Magnetic Resonance Imaging" Ann Neurol 1995; 38(2), 186-193.

Hickey M. et al., "Leukocyte-Endothelial Cell Interactions are enhanced in Dermal Postcapillary Venules of MRL/fas[lpr] (Lupus-Prone) Mice: Roles of P- and E-Selectin[1]" J Immunol. 168(9):4728-36 (2002.

Haworth and Hirst, XXII—The Constitution of the Disaccharides. Part V, Vellobiose (Cellose)J. Chem. Soc. 119, 193 (1921).

Ke Hu et al, "Methyl protogracillin (NSC-698792): the spectrum of cytotoxicity against 60 human cancer cell lines in the National Cancer Institute;s anticancer drug screen panel", Anti-cancer Drugs 2001, 12, pp. 541-547.

Ke Hu et al "The Cytotoxity of Methyl Protoneogracillin (NSC-698793) and Gracillin (NSC-698787), Two Steroidal Saponins from the Rhizomes of Dioscorea collettii var. hypoglauca, against Human Cancer Cells in vitro", Phytother. Res. 17, 620-626 (2003).

Ke Hu et al "Antineoplastic Agents; 11. Four Furostanol Glycosides from Rhizomes of Dioscorea collettii var. hypoglauca", Planta Medica 63 (1997) 161-165.

Hurwitz AA et al "Tumor Necrosis Factor α Induces Adhesion Molecule Expression on Human Fetal Astrocytes", J. Exp. Med, 1992 vol. 176, Dec. 1992 pp. 1631-1636.

Kentaro Inoue et al, "Purification and characterization of furostanol glycoside 26-0-β-glucosidase from Costus speciosus rhizomes", FEDS Letters, 278 (1996) pp. 157-160.

Inoue T. et al., "Blockade of PSGL-1 attenuates CD14 +monocytic cell recruitment in intestinal mucosa and ameliorates ileitis in SAMP1/Yit mice", J Leukoc Biol. 77(3):287-95 (2005).

Kessar S. et al., "Synthetic Studies in Steroidal Sapogenins and Alkaloids-III" Tetrahedron. 24(2):887-92 (1968).

Kessar S et al., "Synthetic Studies in Steroidal Sapogenins and Alkaloids-V", Tetrahedron vol. 24, pp. 899-904 (1968).

Kessar S et al., "Synthetic Studies in Steroidal Sapogenins and Alkaloids-VI", Tetrahedron vol. 24, pp. 905-907 (1968).

Ravindra Kumar et al., "Core 1 β-1,6-N-Acetylglucosaminyltransferase Enzyme Activity is Critical for P-Selectin Glycoprotein Ligand-1 Binding to P-Selectin", Blood, vol. 88, No. 10, pp. 3872-3879 (1996).

Martina Lahmann et al.,"A facile approach to diosgenin and furostan type saponins bearing a 3β-chacotriose moiety"., Carbohydrate Research 337 (2002) 2153-2159.

Marion Lanteri et al., "Altered T cell surface glycosylation in HIV-1 infection results in increased susceptibility to galectin-1-induced cell death", Glycobiology vol. 13, No. 12, pp. 909-918 (2003).

Sohpie Lautrette et al., "A new method of solvent free 0- and N-glycosylation using activated carbon fiber 9ACF) as a promoter. Application to the synthesis of saponin and nucleoside analogues", Chem Commun. (2004) pp. 586-587.

Chuan Li et al., "Synthesis of diosgenyl α-L-rhamnopyransoyl-(1→2)-[β-D-glycopyranosyl-(1→3)]-β-D-glucopyranoside (gracillin) and related saponins", Carbohydrate Research 306 (1998) 189-195.

Ming Li et al., "Synthesis of monomethylated dioscin derivatives and their antitumor activities", Carbohydrate Research 338 (2003) 117-121.

Liu C. et al, Yaoxue Xuebao, (1983) vol. 18, p. 8 pp. 597-606.

Hongwei Liu et al ., "Two new Pregnane Glycosides from Dioscorea futschauensis R. Kunth"., Chem. Pharm. Bull. 51(9) 1089-1091 (2003).

Robert W McMurray et al., "Adhesion Molecules in Autoimmune Disease"., Semin. Arthritis and Rheumatism vol. 25, No. 4, Feb. 1996, pp. 215-233.

Yoshihiro Mimaki et al., "Steroidal Saponins from the bulbs of Lilium regale and L. henryI"., Phytochemistry, vol. 33 No. 3 pp. 675-682, 1993.

Yoshihiro Mimaki et al., "Steroidal Saponins from the bulbs of Lilium longiglorum and their antitumour-promoter activity"., Phytochemistry, vol. 37, No. 1 pp. 227-232 (1994).

Yoshihiro Mimaki et al., "New Steroidal Constituents from the Bulbs of Lilium candidum", Chem. Pharm. Bull 46 (11) 1829-1832 (1998).

Daniel Myers, et al., "New and Effective Treatment of Experimentally Induced Venous Thrombosis with Anti-inflammatory rPSGL-lg", Throm Haemost 2002, 87, 374-82.

Osamu Nakamura, et al., "Steroidal Saponins from the Bulbs of Lilium speciosum x L. nobilissimum 'Star Gazer' and their antitumour-promoter activity", Phytochemistry, vol. 36, No. 2, pp. 463-467 (1994).

Kenji Oda et al., "Adjuvant and Haemolytic Activities of 47 Saponins Derived from Medicinal and Food Plants"., Biol. Chem. vol. 381, pp. 67-74, Jan. 2000.

Kazutomo Ori et al., "Jatropham Derivatives and steroidal saponins from the Bulbs of Lilium hansonlI"., Phytochemistry., vol. 31, No. 8, pp. 2767, 2775, (1992).

Jean-Hugues Renault et al., "Dammarane Saponins from Zizyphus lotus", Phytochemistry vol. 44, No. 7., pp. 1321-1327 (1997).

Emile M. Rijcken et al., "Immunoblockade of PSGL-1 attenuates established experimental murine colitis by reduction of leukocyte rolling", Am J Physiol 287, G115-G124, (2004).

Shengmin Sang et al., "Furostanol saponins from Allim tuberosum"., Phytochemistry 52 (1999) pp. 1611-1615.

Serban C Stoica et al., "Endothelial Activation in the Transplanted Human Heart from Organ Retrieval to 3 months after Transplantation: an Observational Study", J. Heart Lung/Transplant., 24(5) 593-601 (2005).

Kurt Hostettmann et al., Saponins (Chemistry and pharmacology of natural products) (1995), Cambridge University Press 1995.

Erich C Strauss et al ., "Soluble P-Selectin Glycoprotein Ligand 1 Inhibits Ocular Inflammation in a Murine Model of Allergy", Invest Ophthalmol/Vis Sci. 40(7); 1336-421 (1999).

Jean-Francois Tanguay et al., "Prevention of in-stent restenosis via reduction of thrombo-inflammatory reactions with recombinant P-selectin glycoprotein ligand-1", thromb Haemost 2004, 91, 1186-93.

Akihiko Tobari et al, "Spirostanols obtained by cyclization of pseudosaponin derivatives and comparison of anti-platelet agglutination activities of spirostanol glycosides", Eur. J. Med. Chem 35 (2005) 511-527.

M. Tomova et al., "Steroidal Saponins from Tribulus Terrestris L. with a Stimulating Action on the Sexual Functions", Int. Conf. Chem Biotechnol (1981), 3, 1, 298-302.

I. S Vail'eva et al., "Steroid Saponins from Rhizomes of the Caucasian Yam", Pnkl. Biochim Mikrobiol (1984) 20(3) p. 330-332.

Kai Wang et al., "Recombinant Soluble P-Selectin Glycoprotein Ligand-lg (rPSGL-lg) Attenuates Infarct Size and Myeloperoxidase Activity in a Canine Model of Ischemia-Reperfusion", Thromb Haemost (2002) 88, 149-54.

Shao-Min Wang et al., "Syntheses of acetylated steroid glycosides and selective cleavage of O-acetyl groups in sugar moiety", Steroids 69 (2004) 599-604.

Tadayuki Yago et al., "Structurally Distinct Requirements for Binding of P-selectin Glycoprotein Ligand-1 and Sialyl Lewis × to *Anaplasma phagocytophilum* and P-selectin", J. Biol Chem. (2003) vol. 278, No. 39, 37987-37997.

Deng-Jye Yang et al., "Isolation and Identification of Steroidal Saponins in Taiwanese Yam Cultivar (Dioscorea pseudojaponica Yamamoto", J. Agric. Food Chem. (2003) 51, 6438-6444.

Feng Yin et al., "Dammarane-Type Glycosides from *Gynostemma pentaphyllum*", J. Nat. Prod. (2004) 67 pp. 942-952.

Kazuko Yoshikawa et al., "Antisweet Natural Products. VII. Hodulosides I, II, III, IV and V from the Leaves of *Hovenia dulcis* THUNB", Chem Pharm. Bull. 40(9) 2287-2291 (1992).

Kazuko Yoshikawa et al.,"Antisweet Natural Products. VI. Jujubasaponins IV, V and VI from *Zizyphus jujube mill*.", Chem. Pharm. Bull. 40(9) 2275-2278 (1992).

Qing-An Zheng et al., "Steroidal saponins from fresh stem of *Dracaena cochinchinensis*", Steroids 69 (2004) 111-119.

PCT Notification of Transmittal of the International Search Report and the Written Opinion of the International Searching Authority, or the Declaration, International Application No. PCT/GB2004/005398, filed Dec. 22, 2004; Applicant's or agent's file Reference No. 500496WO01; May 31, 2005.

Cheng, M.S., et al; "Total Synthesis of Methyl Protodioscin: A Potent Agent with Antitumor Activity"; *J. Org. Chem*.; vol. 68; pp. 3658-3662 (2003); Citation May 31, 2005; XP-002328851.

Ravikumar, P.R., et al; Chemistry of Ayurvedic Crude Drugs: Part VI[a]-(Shatavari-1): Structure of Shatavarin-IV[b,c]; *Indian Journal of Chemistry*; vol. 26B, pp. 1012-1017 (1987); Citation May 31, 2005; XP-001096221.

Toki, D., et al; "Inhibition of UDP-GlcNAc:Galβ-3GalNAc-R (GlcNAc to GalNAc) β6-N-acetylglucosaminyltransferase from acute myeloid leukaemia cells by photoreactive nitrophenyl substrate derivatives"; *Biochemical and Biphysical Research Communications*; vol. 193, No. 2; pp. 417-423 (1994); Citation May 31, 2005; XP002922997.

Yoshikawa, M., et al; "Medicinal Foodstuffs. VIII.[1] Fenugreek Seed. (2) : Structures of Six New Furostanol Saponins, Trigoneosides IVa, Va, Vb, VI, VIIb, and VIIIb, From the Seeds of Indian *Trigonella Foenum-Graecum L*."; *Heterocycles*, vol. 47, No. 1; pp. 397-405 (1998); Citation May 31, 2005; XP-001205771.

PCT Notification of Transmittal of the International Search Report and the Written Opinion of the International Searching Authority, or the Declaration, International Application No. PCT/GB2006/002301, filed Jun. 22, 2006; Applicant's or agent's file Reference No. 500966WO01 Nov. 15, 2006.

Orlacchio, A., et al; "Activity levels of a β1,6 N-acetylglucosaminyltransferase in lymphomonocytes from multiple sclerosis patients"; *Journal of the Neurological Sciences*; vol. 151; pp. 177-183 (1997); Citation Nov. 15, 2006; XP-002232475.

PCT Notification of Transmittal of the International Search Report and the Written Opinion of the International Searching Authority, or the Declaration, International Application No. PCT/GB2006/002500, filed Jul. 6, 2006; Applicant's or agent's file Reference No. 500964WO01 May 25, 2007.

Derwent Publications Ltd., London, GB; AN 2003-664094 & CN 1 415 625 A (Jilin Tianyao Sci & Technology Co. Ltd) May 7, 2003; Citation May 25, 2007; (Abstract) XP-002433233.

Derwent Publications Ltd., London, GB; AN 2001-412294 & JP 2001 072597 A (merican Corp); Mar. 21, 2001; Citation May 25, 2007; (Abstract) XP-002433234.

Derwent Publications Ltd., London, GB; AN 2000-476485 & CN 1 243 129 A (Univ. Shenyang Medicine); Feb. 2, 2000; Citation May 25, 2007; (Abstract) XP-002433235.

Hu, K., et al; "The Cytotoxicity of Methyl Protoneogracillin (NSC-698793) and Gracillin (NSC-698787), Two Steroidal Saponins from the Rhizomes of *Dioscorea collettii* var. *hypoglauca*, against Human Cancer Cells in vitro"; *Phytother. Res*., vol. 17, pp. 620-626 (2003); Citation May 25, 2007.

Aquino, R., et al; "Antiviral Activity of Constituents of *Tamus communis*"; *Journal of Chemotherapy*; vol. 3, No. 5; pp. 305-309 (1991); Citation May 25, 2007.

Baek, S.H., et al; "Inactivation of Human Pleural Fluid Phospholipase $A_2$ by Dioscin"; *Arch. Pharm. Res*.; vol. 17, No. 4; pp. 218-222 (1994); Citation May 25, 2007.

Ondeyka, J.G., et al; "Discovery of structurally diverse natural product antagonists of chemokine receptor CXCR3"; *Molecular Diversity*; vol. 9; pp. 123-129 (2005); Citation May 25, 2007.

Sautour, M., et al; "Antifungal steroid saponins from Dioscorca caycncnsis. Plant Medica;" *Antimicrobial Activity*; vol. 70(1); pp. 90-92 (2004); Citation May 25, 2007.

PCT Notification of Transmittal of the International Search Report and the Written Opinion of the International Searching Authority, or the Declaration, International Application No. PCT/GB2006/002518, filed Jul. 6, 2006; Applicant's or agent's file Reference No. 500965WO01; Dec. 19, 2006.

Derwent Publications Ltd., London, GB; AN 2004-239758; Huang, H., et al; "Medicine composition for treating myocardial ischemia, angina pectoris and cardiac infraction"; & CN 1 465 344 A (Chengdu Diao Pharm Group Co Ltd) Jan. 7, 2004 (Abstract) XP-002409228; Citation Dec. 19, 2006.

Derwent Publications Ltd., London, GB; AN 2005-426073; Wang Jingang; "Dioscin oral disintegration tablet and its preparing method"; & CN 1 586 493 A (Kexinbicheng Medicine Science) Mar. 2, 2005 (Abstract) XP-002409229; Citation Dec 19, 2006.

Derwent Publications Ltd., London, GB; AN 2002-751531; Zhu Dayuan et al; "Furost saponine analogue and its separatin process and use" & CN 1 184 229 C (Shanghai Inst of Pharmacology) Jan. 12, 2005 (Abstract) XP-002409230; Citation Dec. 19, 2006.

Derwent Publications Ltd., London, GB; AN 2005-631469; Han J. et al; "Medicine for regulating blood fat and treating cardiocerebral disease and preparing method"; & CN 1 615 896 A (Yunnan Prov Medicine Inst) May 18, 2005 (Abstract) XP-002409231; Citation Dec. 19, 2006.

Derwent Publications Ltd., London, GB; AN 2000-443110; Li Pingya et al; "Process for extracting ginsenoside Re, and use of medicine thereof"; & CN 1 242 374 A (Xinliheng Pharmaceutical Scien) Jan. 26, 2000; (Abstract) XP-002409232; Citation Dec. 19, 2006.

Derwent Publications Ltd., London, GB, AN 1998-087548; Junpeng Peng et al; "Anti-thrombosis glucoside medicine"; & CN 1 138 984 A (Radiomedicine Inst Military ME) Jan. 1, 1997; (Abstract) XP-002409233; Citation Dec. 19, 2006.

Derwent Publications Ltd., London, GB, AN 2006-272298; Fu T., et al; "Steroidal saponin pharmaceutical composition, its preparation method and use"; & WO 2006/034655 A (chengdu Diao Pharm Group Co Ltd) Apr. 6, 2006 (Abstract) XP-002409234; Citation Dec. 19, 2006.

Zhang, J., et al; "Effect of six steroidal saponins isolated from anemarrhenae rhizome on platelet aggregation and hemolysis in human blood"; *Clinica Chimica Acta*; vol. 289; pp. 79-88 (1999); Citation Dec. 19, 2006.

L. S. Akhov et al.2000, Biological Activity of Deltoside from *Allium nutans* L. In Saponins in Food, Feedstuffs and Medicinal Plants edited by W Oleszek and A Marston.

Bemadete P. da Silva, et al, A New Bioactive Steroidal Saponin from *Agave attenuata*; Z. Naturforsch, 57c, 423-428 (2002).

Mei Dong et al, Two New Steroidal Saponins from the Rhizomes of Dioscorea panthaica and their Cytotoxic Activity; Planta Med. 67 (2001) 853-857.

Dong et al, Steroidal saponins from Dioscorea panthaica and their cytotoxic activity; Pharmazie 59, 294-296 (2004).

B. B. Gaitonde et al; Antioxytocic action of Saponin isolated from *Asparagus racemosus* Willd (Shatavari) on Uterine Muscle; Arch. int. Pharmacodyn., 1969, 179, No. 121-129.

Antonio G. Gonzalez et al; Steroidal Saponins from the Bark of *Dracaena draco* and Their Cytotoxic Activities; J. Nat. Prod. 2003, 66, 793-798.

Juan C. Hernandez et al, Icogenin, a new cytotoxic steroidal saponin isolated from *Dracaena draco*; Bioorganic & Medicinal Chemistry 12 (2004) 4423-4429.

Hiroschige Hibasami et al, Protodioscin isolated from fenugreek (*Trigonella foenumgraecum* L). induces cell death and morphological change indicative of apoptosis in leukemic cell line H-60, but not in gastric cancer cell line KATO III; International Journal of Molecular Medicine 11: 23-26, 2003.

Ke Hu et al; Methyl protogracillin (NSC-698792): the spectrum of cytotoxicity against 60 human cancer cell lines in the National Cancer Institute's anticancer drug screen panel, Anti-Cancer Drugs 2001, 12, pp. 541-547.

Sung Yong Kim et a!; Inhibition of Mouse Ear Edema by Steroidal and Triterpenoid Saponins: Arch Pharm Res, vol. 22, No. 3, 313-316, 1999.

M. A. Lacaille-Dubois et al; A review of the biological and pharmacological activities of saponins: Phytomedicine vol. 2(4), pp. 363-386, 1996.

H.W. Liu et al; Bioactive saponins from *Dioscorea futschauensis*: Pharmazie 57 (2002) 8 570-572.

Hisashi Matsuda et al; Protective Effects of Steroid Saponins from *Paris polyphylla* var. *yunnanensis* on Ethanol- or Indomethacin-Induced Gastric Mucosal Lesions in Rats: Structural Requirement for Activity and Mode of Action: Bioorganic & Medicinal Chemistry Letters 13 (2003) 1101-1106.

Yoshihiro Mimaki et al; Steroidal Saponins from the bulbs of *Triteleia Lactea* and their inhibitory activity on cyclic amp phosphodiesterase: Phytochemistry, vol. 38, No. 5, pp. 1279-1286, 1995.

Yoshihiro Mimaki et al; Cytotoxic Activities and Structure-Cytotoxic Relationships of Steroidal Saponins: Biol. Pharm. Bull, 24(II) 1286-1289 (2001).

Pierre R Petit et al; Steroid saponins from fenugreek seeds: Extraction, purification, and pharmacological investigation on feeding behaviour and plasma cholesterol: Steroids, 60: 674-680, 1995.

P. Sur et al; Short Communication *Trigonella foenum* graecum (Fenugreek) Seed Extract as an Antineoplastic Agent: Phytotherapy Research, 15, 257-259 (2001).

Yi-Fei Wang et al; Inhibitory Effects of Some Steroidal Saponins on Human Spermatozoa in vitro: Planta Medica 62 (1996)130-132.

Ethan Basch et al; Therapeutic Applications of Fenugreek: Alternative Medicine Review vol. 8, No. 1, 2003 pp. 20-27.

Dinesh Puri; Therapeutic Potentials of Fenugreek: Indian J Physiol Pharmacol. 1998; 42(3) pp. 423-424.

L. S. Akhov et al Structure of Steroidal Saponins from Underground Parts of *Allium nutans L*.; J. Agric. Food Chem. 1999, 47, 3193-3196.

Paul V. Beaum et al; Expression of Core 2 β-1,6-N-Acetylglucosaminyltransferase in a Human Pancreatic Cancer Cell Line Results in Altered Expression of MUC1 Tumor-associated Epitopes; The Journal of Biological Chemistry, vol. 274, No. 35, Issue of Aug. 27, pp. 24641-24648, 1999.

Christopher Boca et al; 4-Hydroxyisoleucine: effects of synthetic and natural analogues on insulin secretion; European Journal of Pharmacology 390 (2000) 339-345.

I. Brockhausen et al; Biosynthesis of O-Glycans in Leukocytes from Normal Donors and from Patients with Leukemia: Increase in O-Glycan Core 2 UDP-GlcNAc:Galβ3GalNAcα-R(GlcNAc to GalNAc)β(1-6)-N-Acetylglucosaminyltransferase in Leukemic Cells; Cancer Research 51, 1257-1263, Feb. 15, 1991.

Mao S. Cheng et al; Total Synthesis of Methyl Protodioscin: A Potent Agent with Antitumor Activity; J.Org.Chem. 2003, 68, 3658-3662.

Rakesh Chibber et al; Activity of the Glycosylating Enzyme, Core 2 GlcNAc (β1,6) Transferase, Is Higher in Polymorphonuclear Leukocytes from Diabetic Patients Compared with Age-Matched Control Subjects; Diabetes, vol. 49, Oct. 2000, pp. 1724-1730.

Karen J. Colley; Golgi localization of glycosyltransferases: more questions than answers; Glycobiology vol. 7, No. 1 pp. 1-13, 1997.

Martin Dalziel et al; The Relative Activities of the C2GnT1 and ST3Gal-I Glycosyltransferases Determine O-Glycan Structure and Expression of a Tumor-associated Epitope on MUCI; The Journal of Biological Chemistry Vo. 276, No. 14, Issue of Apr. 6, pp. 11007-11015, 2001.

Matthew D. Davis et al, Diabetic Retinopathy; Diabetes Care, vol. 15, No. 12, Dec. 1992, pp. 1844-1874.

Michael J. Davies et al; The expression of the adhesion molecules ICAM-1, VCAM-1, PECAM, and E-Selectin in Human Atherosclerosis; Journal of Pathology, vol. 171, 223-229 (1993).

Shaojiang Deng et al; Synthesis of three diosgenyl saponins: dioscin, polyphyllin D, and balanitin 7; Carbohydrate Research 317 (1999) 53-62.

Yuguo Du et al; Synthesis of Saponins Using Partially Protected Glycosyl Donors; Organic Letters 2003, vol. 5, No. 20, 3627-3630.

Lesley G. Ellies et al; Core 2 Oligosaccharide Biosynthesis Distinguishes between Selectin Ligands Essential for Leukocyte Homing and Inflammation; Immunity, vol. 9, 881-890, Dec. 1998.

Umit Guray et al; Levels of Soluble adhesion molecules in various clinical presentations of coronary atherosclerosis; International Journal of Cardiology 96 (2004) 235-240.

Umit Guray et al; Poor coronary collateral circulation is associated with higher concentrations of soluble adhesion colecules in patients with single-vessel desease; Coronary Artery Disease 2004, 15: 413-417.

Jayshree Joshi et al; Chemistry of Ayurvedic Crude Drugs: Part VIII—Shatavari-2: Structure Elucidation of Bioactive Shatavarin-I & other Glycosides: Indian Journal of Chemistry, vol. 27B, Jan. 1988, pp. 12-16.

Ronald Klein et al; The Wisconsin Epidemiologic Study of Diabetic Retinopathy: X. Four-Year Incidence and Progression of Diabetic Retinopathy When Age at Diagnosis is 30 years or More; Arch Ophthalmol 1989; 107: 244-249.

Eva M. Kohner et al; Diabetic Retinopathy in Diabetic Angiopathy, Tooke J.E., pp. 233-247, Oxford University Press (1999).

Daisuke Koya et al; Perspectives in Diabetes: Protein Kinase C Actibvation and the Development of Diabetic Complications; Diabetes, vol. 47, 859-866, 1998.

Diasuke Koy et al; Overexpression of core 2, N-acetylglycosaminyltransferase enhances cytokine actions and induces hypertrophic myocardium in transgenic mice: FASEB J. 13, 2329-2337 (1999).

William Kuhns et al; Procession O-glycan core 1, Galβ1-3GalNAcα-R, Specificities of core 2, UDP-GLcNAc: Galβ1-3GalNAc-R(GLcNAc to GalNAc)β6-N-acetylglycosaminyltransferase and CMP-sialic acid: Galβ1-3GalNAc-R α3-sialyltransferase: Glycoconjugate Journal (1993) 10 : 381-394.

Kensuke Kumamoto et at; Specific Detection of Sialyl Lewis X Determinant Caried on the Mucin GlcNAβ1→6GaINAcα Core Structure as a Tumor-Associated Antigen; Biochemical and Biophysical Research Communications 247, 514-517 (1998).

Suzanne Laferte et al; Glycosylation-dependent Collagen-binding Activities of Two Membrane Glycoproteins in MDAY-D2 Tumor Cells: Cancer Research 48, 4743-4748, Sep. 1, 1988.

Chuan Li, et al; Synthesis of Diosgenyl α-L-rhamnopyranosyl-(1→2)—[β-D-glucopyranosyl-(1→3)]-β-D-glucopyranoside (gracillin) and related saponins; Carbohydrate Research 306 (1998) 189-195.

Bing Li et al; An improved synthesis of the saponin, polyphyllin D; Carbohydrate Research 331 (2001) 1-7.

Emi Machida et a!; Clinicopathological Significance of Core 2 β,6-N- Acetylglucosaminyltransferase Messenger RNA Expressed in the Pulmonary Adenocarcinoma Determined by in situ hybridization; Cancer Research 61, 2226-2231, Mar. 1, 2001.

Marja-Leena Majuri et al; Recombinant E-selectin-protein mediates tumor cell adhesion via sialyl-Lea and sialyl-Lex; Biochemical and Biophysical Research Communications, vol. 182, No. 3 1992, Feb. 14, 1992, pp. 1376-1382.

Matthias Meier et al; Protein kinase C activation and its pharmacological inhibition in vascular disease; Vascular Medicine 2000; 5: 173-185.

Yoshihiro Mimaki et al; Steroidal Saponins and Alkaloids from the Bulbs of *Lilium brownie* var. *colchesteri*; Chem. Pharm. Bull 38(11) 3055-3059 (1990).

N T Mulvihill et al ; Inflammation in acute coronary syndromes; Heart 2002, 87, 201-204.

Toshiyuki Murakami et al; Medicinal Foostuffs. XVII. Fenugreek Seed. (3): Structures of New Furostanol-Type Steroids Saponins, Trigoneosides Xa, Xb, XIb, XIIa, XIIb, and XIIIa, from the Seeds of Egyptian *Trigonella Foenum-graecum L*; Chem. Pharma. Bull. 48(7)1994-1000 (2000).

,Mitsuru Nakamura et al; Simultaneous core 2 β1→6N-acetylglycosaminyltransferase up-regulation and sialyl-Le expression during activation of human tonsillar B lymphocytes; FEBS Letters 463 (1999) 125-128.

Yoshihiko Nishio et al; Identification and Characterization of a Gene Regulating Enzymatic Glycosylation which is Induced by Diabetes and Hyperglycemia Specifically in Rat Cardiac Tissue; J. Clin. Invest. vol. 96, Oct. 1995, 1759-1767.

Kevin D O'Brien et al; Neovascular Expression of E-Selectin, Intercellular Adhesion Molecule-1, and Vascular Cell Adhesion Molecule-1 in Human Atherosclerosis and Their Relation to Intimal Leukocyte Content; 1996 American Heart Association, In.c. 1996; 93: 672-682.

Katsuyuki Ohmori et al; A Distinct Type of Sialyl Lewis X Antigen Defined by a Novel Monoclonal Antibody is Selectively Expressed on Helper Memory T Cells; Blood, vol. 82, No. 9 (Nov. 1, 1993) pp. 2797-2805.

Hans Paulsen et al; Synthese von modifizierten Derivaten des Disaccharides β-D-Gal-(1→3)-α-D-GalNAc zur Untersuchung der Substratspezifitat der Core-2-β6-GlcNAc-Transferase and α-3-Sialyltransferase der Biosynthese von O-Glycoproteinen: Liebigs Ann. Chem. 1992, 747-758.

George R Pettit et al: Isolation and Structure of Cytostatic Steroidal Saponins from the African Medicanal Plant Balanites Aegyptica; Journal of Natural Products Vo. 54, No. 6 pp. 1491-1502 Nov.-Dec. 1991.

Friedrich Piller et al; Human T-lymphocyte Activation is Associated with changes in O-Glycam Biosynthesis; The Journal of Biological Chemistry, vol. 263, No. 29, Issue of Oct. 15, pp. 15146-15150, 1988.

Jutta Renkonen et al; Core 2 β1,6-N-acetylglycosaminyltransferases and α1,3-fucosyltransferases regulate the synthesis of O-glycans on selectin ligands on oral cavity carcinoma cells; APMIS 109, 500-6, 2001.

P. R. Ravikumar et al; Chemistry of Ayurvedic Crude Drugs: Part VI-(Shatavari-1):Structure of Shatavarin-IV; Indian Journal of Chemistry vol. 26B, Nov. 1987, pp. 1012-1017.

Osamu Saitoh et al; Expression of Aberrant O-Glycans attached to Leukosialin in Differentiation-deficient HL-60 Cells; Cancer Research 51, 2854-2862, Jun. 1, 1991.

Yutaka Sashida et al; Studies on the Chemical Constituents of the Bulbs of *Lilium mackliniae*; Chem. Pharm. Bull. 39 (9) 2362-2368 (1991).

Yves Sauvaire et al; 4-Hydroxyisoleucine. A novel amino acid potentiator of insulin secretion; Diabetes, vol. 47, Feb. 1998 pp. 206-210.

S C Sharma et al; Oligofurostanosides from *Asparagus curillus* leaves; Phytochemistry, Vo. 33, No. 3, pp. 683-686, 1993.

R D Sharma et al; Effect of fenugreek seeds on blood glucose and serum lipds in Tyupe 1 diabetes; European Journal of Clinical Nutrition (1990) 44, 301-306.

Kazuhisa Shimodaira et al; Carcinoma-associated Expression of Core 2 β-1,6-N-Acetylglucosaminyltransferase Gene in Human Colorectal Cancer: Role of O-Glycans in Tumor Progression; Cancer Research 57, 5201-5206 Dec. 1, 1997.

Hiroko Shimomura et al; Steroidal Saponins, PardarinosideA-G from the Bulbs of Lilium Pardarinum; Phytochemistry, Vo. 28, No. 11 pp. 3163-3170, 1989.

Markus Sperandio et al; Severe impairment of leukocyte rolling in venules of core 2 glyucosaminyltransferase-deficient mice; Blood, Jun. 15, 2001, vol. 97. No. 12, pp. 3812-3819.

Akiko Takada et al; Contribution of Carbohydrate Antigens Sialyl Lewis a and Sialyl Lewis X to Adhesion of Human Cancer Cells to Vascular Endothelium; Cancer Research 53, 354-361, Jan. 15, 1991.

Shigeru Tsuboi et al; Branched O-linked oligosaccharides ectopically expressed in transgenic mice reduce primary T-cell immune responses; The EMBO Journal vol. 16, No. 21, pp. 6364-6373, 1997.

Shigeru Tsuboi et al; Overexpression of Branched O-Linked Oligosaccharides on T Cell Surface Glycoproteins Impairs Humoral Immune Responses in Transgenic Mice; The Journal of Biological Chemistry Vo. 273, No. 46, Issue of Nov. 13, pp. 30680-30687, 1998.

Shigeru Tsuboi et al; Roles of O-linked oligosaccharides in immune responses; BioEssays 23:46-53, 2001.

Ajit Varki; Special Invited Review: Biological roles of oligosaccharides: all of the theories are correct; Glycobiology Vo. 3, No. 2 pp. 97-130, 1993.

I.S.Vasil'eva et al; Composition and Biological Activity of Steroid Glycosides from Cell Suspensions of *Discorea deltoidea* Wall; Applied Biochemistry and Microbiology, vol. 31, No. 2, 1995 pp. 206-209.

Gerd Walz et al; Recognition by ELAM-1 of the Sialyl-Le Determinant on Myeloid and Tumor Cells; Science, vol. 250 pp. 1132-1135, 1990.

Patricia P Wilkins et al; Structures of the O-Glycans on P-selectin Glycoprotein Ligand-1 from HL-60 Cells; The Journal of Biological Chemistry, vol. 271, No. 31, Issue of Aug. 2, pp. 18732-18742, 1996.

David Williams et al; Detection in Canine Submaxillary glands of an N-Acetylglucosaminyltransferase which acts on mucin substrates; The Journal of Biological Chemistry, vol. 255, No. 23, Issue of Dec. 10, pp. 11247-11252, 1980.

Masayuki Yoshikawa et al; Medicinal Foodstuffs IV. Fenugreek Seed. (1): Structures of Trigoneosides Ia, Ib, IIa, II13, IIIa and IIIb, New Furostanol Saponins from the Seeds of Indian *Trigonella foenum-graecum* L; Chem. Pharm. Bull. 45(1) 81-87 (1997).

Masayuki Yoshikawa et al; Medicinal Foodstuffs, VIII. Fenugreek Seed (2): Structures of six new Furostanol Saponins Trigoneosides IVa, Va, Vb, Vi, VIIb, and VIIIb, from the Seeds of Indian *Trigonella foenum-Graecum L*.; Heterocycles, vol. 47, No. 1, 1998, pp. 397-405.

Shida Yousefi et al; Increased UDP-GlcNAc:Galβ1-3GalNAc-R (GlcNAc to GalNAc) β-1, 6-N-Acetylglucosaminyltransferase Activity in Metastatic Murine Tumor Cell Lines; The Journal of Biological Chemistry, vol. 266, No. 3, Issue of Jan. 25, pp. 1772-1782, 1991.

Biao Yu, A "Double Random" Strategy for the Preparation of Saponin Libraries; J. Comb. Chem. 2001, 3, 404-406.

Biao Yu et al; The first synthetic route to furostan saponins; Tetrahedron Letters 42 (2001) pp. 77-79.

Biao Yu, et al; Glycosyl Trifluoroacetimidates.2. Synthesis of Dioscin and Xiebai Saponin 1; J. Org Chem. 2002, 67, 9099-9102.

Robert A Moreau et al; Phytosterols, phytostanols, and their conjugates in Foods: structural diversity, quantitative analysis, and health-promoting uses; Progress in Lipd Research 41, (2002) 457-500.

Hostettmann, K. et al; Chemistry and pharmacology of natural products; Saponins Cambridge University Press (1995) (extracted book pages).

Chibber, R., et al; "Protein Kinase C (β2-Dependent Phosphorylation of Core 2 GlcNAc-T Promotes Leukocyte-Endothelial Cell Adhesion"; *Diabeties*; vol. 52; pp. 1519-1527 (2003).

Goekjian, P.G., et al; "Protein kinase C inhibitors as novel anticancer drugs"; *Expert Opin. Investig. Drugs*; vol. 10, No. 12; pp. 2117-2140 (2001).

Hindsgaul, O., et al; "Evaluation of Deoxygenated Oligosaccharide Acceptor Analogs as Specific Inhibitors of Glycosyltransferases"; *The Journal of Biological Chemistry*; vol. 266, No. 27; pp. 17858-17862 (1991).

Kim, S.Y., et al; "Inhibition of Mouse Ear Edema by Steroidal and Triterpenoid Saponins"; *Arch Pharm Res*.; vol. 22, No. 3, pp. 313-316 (1999).

Matsuda, H., et al; "Protective Effects of Steroid Saponins from *Paris polyphylla* var. *yunnanensis* on Ethanol- or Indomethacin-Induced Gastric Mucosal Lesions in Rats: Structural Requirement for Activity and Mode of Action"; *Bioorganic & Medicinal Chemistry Letters*; vol. 13; pp. 1101-1106 (2003).

Toki, D., et al; "Inhibition of UDP-GlcNAc:Galβ1-3GalNAc-R (GlcNAc to GalNAc)β6-N-acetylglucosaminyltransferase from acute myeloid leukaemia cells by photoreactive nitrophenyl substrate derivatives"; *Biochemical and Biophysical Research Communications*; vol. 198, No. 2; pp. 417-423 (1994).

Washington, R., et al; "Expression of Immunologically Relevant Endothelial Cell Activation Antigens on Isolated Central Nervous System Microvessels from Patients with Multiple Sclerosis"; *Ann. Neurol*; vol. 35, No. 1; pp. 89-97 (1994).

Li, Cheng-Ming, et al; "Development of monoclonal antibodies against bovine mucin core 2 β6 N-acetylglucosaminyltransferase"; *Glycoconjugate Journal*; vol. 16; pp. 555-562 (1999).

Confavreux, C., et al; "Age at disability milestones in multiple sclerosis"; *Brain*; vol. 129; pp. 595-605 (2006).

Confavreux, C., et al; "Natural history of multiple sclerosis: a unifying concept"; *Brain*, vol. 129; pp. 606-616 (2006).

Elovaara, I., et al; "Adhesion Molecules in Multiple Sclerosis"; *Arch Neurol*; vol. 57, pp. 546-551 (2000).

McDonnell, G.V., et al; "Serum soluble adhesion molecules in multiple sclerosis: raised sVCAM-1, sICAM-1 and sE-selectin in primary progressive disease"; *J. Neurol*; vol. 246; pp. 87-92 (1999).

Musso, A.M., et al; "Increased serum levels of ICAM-1, ELAM-1 and TNF-α in inflammatory disorders of the peripheral nervous system"; *Ital. J. Neurol. Sci.*; vol. 15; pp. 267-271 (1994).

Rao, A.V., et al; "The Bioactivity of Saponins: Triterpenoid and Steroidal Glycosides"; *Drug Metabolism and drug interactions*; vol. 17, No. 1-4; pp. 212-235 (2000).

Simmons, R.D., et al; "Sialyl ligands facilitate lymphocyte accumulation during inflammation of the central nervous system"; *Journal of Neuroimmunology*; vol. 41; pp. 123-130 (1992).

Ulbrich, H., et al; "Leukocyte and endothelial cell adhesion molecules as targets for therapeutic interventions in inflammatory disease"; *Trends in Pharmacological Sciences*; vol. 24, No. 12; pp. 640-647 (2003).

VanderElst, I.E., et al; "β1,6 N-Acetylglucosaminyltransferase (core 2 GlcNAc-T) expression in normal rat tissues and different cell lines: evidence for complex mechanisms of regulation"; *Glycobiology*, vol. 8, No. 731-740 (1998).

Washington, R., et al; "Expression of Immunologically Relevant Endothelial Cell Activation Antigens on Isolated Central Nervous System Microvessels from Patients with Multiple Sclerosis"; *Annals of Neurology*; vol. 35, No. 1; pp. 89-97 (1994).

Mimaki, Y., et al; "Steroidal Saponins from *Hosta Longipes* and Their Inhibitory Activity on Tumour Promoter-Induced Phospholipid Metabolism of HeLa Cells"; *Phytochemistry*, vol. 42, No. 4, pp. 1065-1070 (1996).

Australian Office Action; Examiner's first report on Patent Application No. 2004305302, dated Aug. 27, 2009 (2 pgs).

Chinese Office Action; Second Office Action on Patent Application No. 200480041735.3, dated Dec. 22, 2004, pp. 1-5.

Chinese Office Action; First Office Action on Patent Application No. 200680032400.4, dated Jul. 6, 2006, pp. 1-5.

Chinese Office Action; First Office Action on Patent Application No. 200680031670.3, dated Jul. 6, 2006, pp. 1-5.

Chinese Office Action; First Office Action on Patent Application No. 200480041735.3, dated Dec. 22, 2004, pp. 1-4.

British Search Report; Application No. GB0513888.8, Date of Search Nov. 1, 2005 (3 pgs).

British Search Report; Application No. GB0513881.3, Date of Search Nov. 1, 2005 (3 pgs).

Mexican Office Action; Application No. PA/a/2006/007087, dated Nov. 19, 2009 (2 pgs).

Xu, X., et al; "Studies on saponin from seeds of *Trigonella foenumgraecum* (II) Isolation and structural elucidation for a new saponin a and its secondary glucosides"; *Chinese Traditional and Herbal Drugs*; p. 679 (2003).

Friedman, M., et al; "Effect of feeding solanidine, solasodine and tomatidine to non-pregnant and pregnant mice"; *Food and Chemical Toxicology*, vol. 41, pp. 61-71 (2003).

Skulina, C., et al; "Multiple sclerosis: Brain-infiltrating CD8$^+$ T cells persist as clonal expansions in the cerebrospinal fluid and blood"; *PNAS*; vol. 101, No. 8; pp. 2428-2433 (2004).

Ley, K., et al; "Selectins in T-Cell Recruitment to Non-Lymphoid Tissues and Sites of Inflammation"; *Nature Reviews Immunology*; vol. 4, pp. 1-11 (2004).

* cited by examiner

FIG. 1 (Continue)
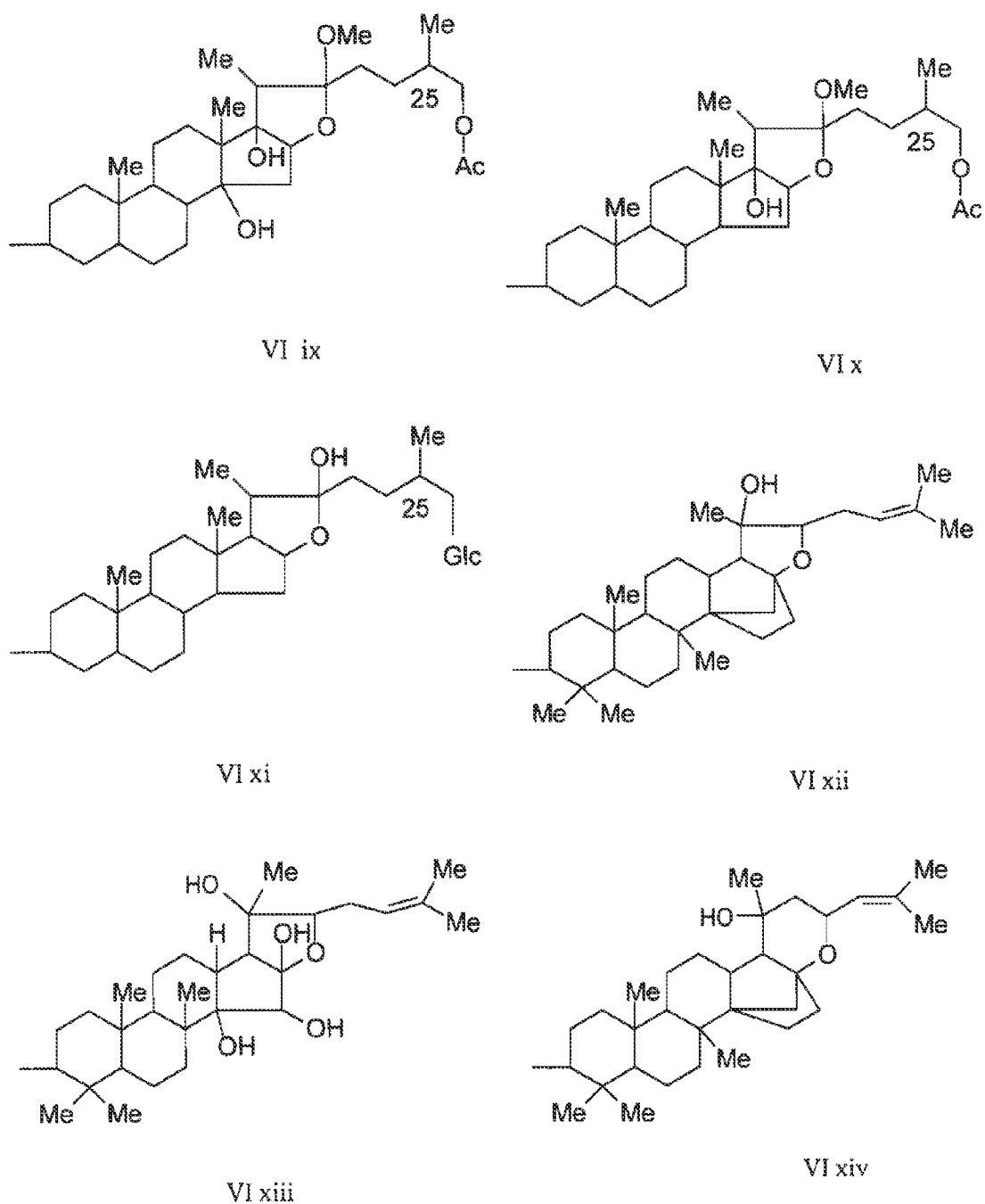

VI xv

VI xvi

VI xvii

VI xviii

VI xix

VI xx

VI xxi

VI xxii

FIG. 2 (Continue)
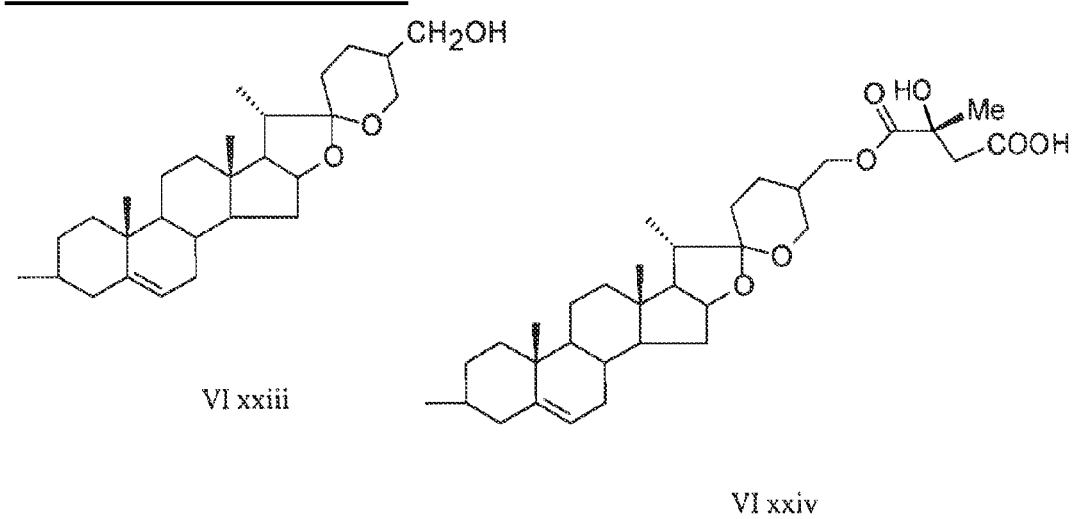
VI xxiii
VI xxiv
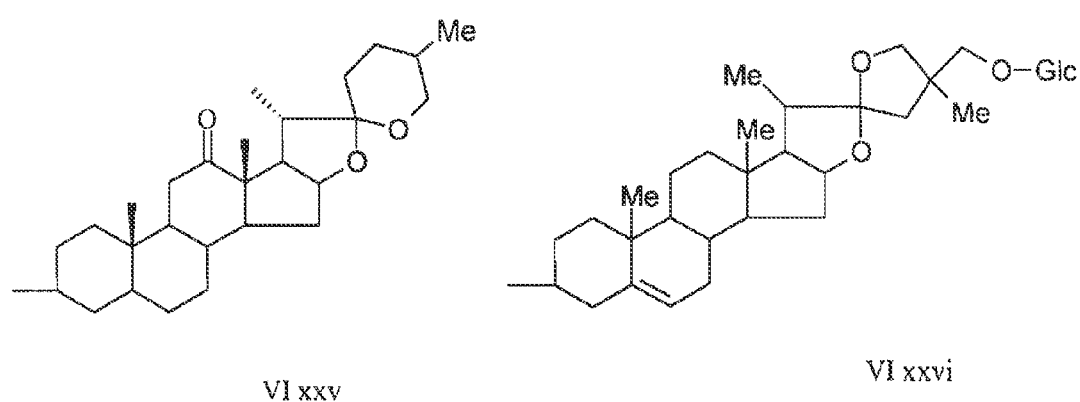
VI xxv
VI xxvi
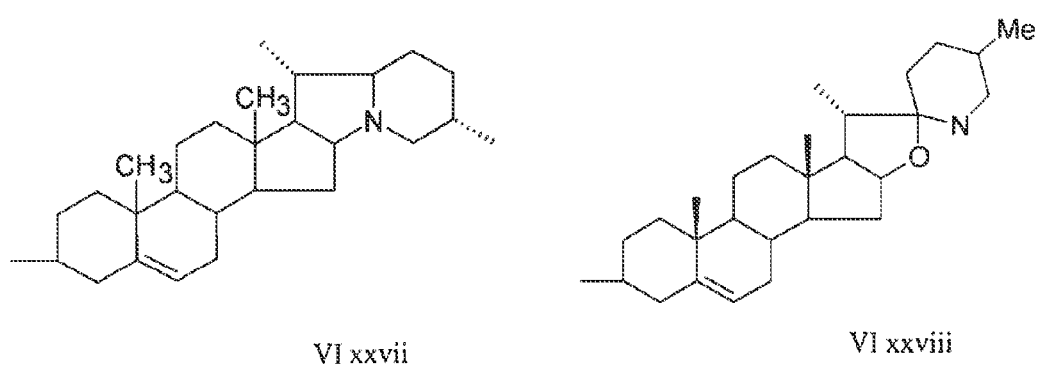
VI xxvii
VI xxviii VI xxviii VI xxix VI xxx VI xxxi VI xxxii

FIG. 16 (Continue)
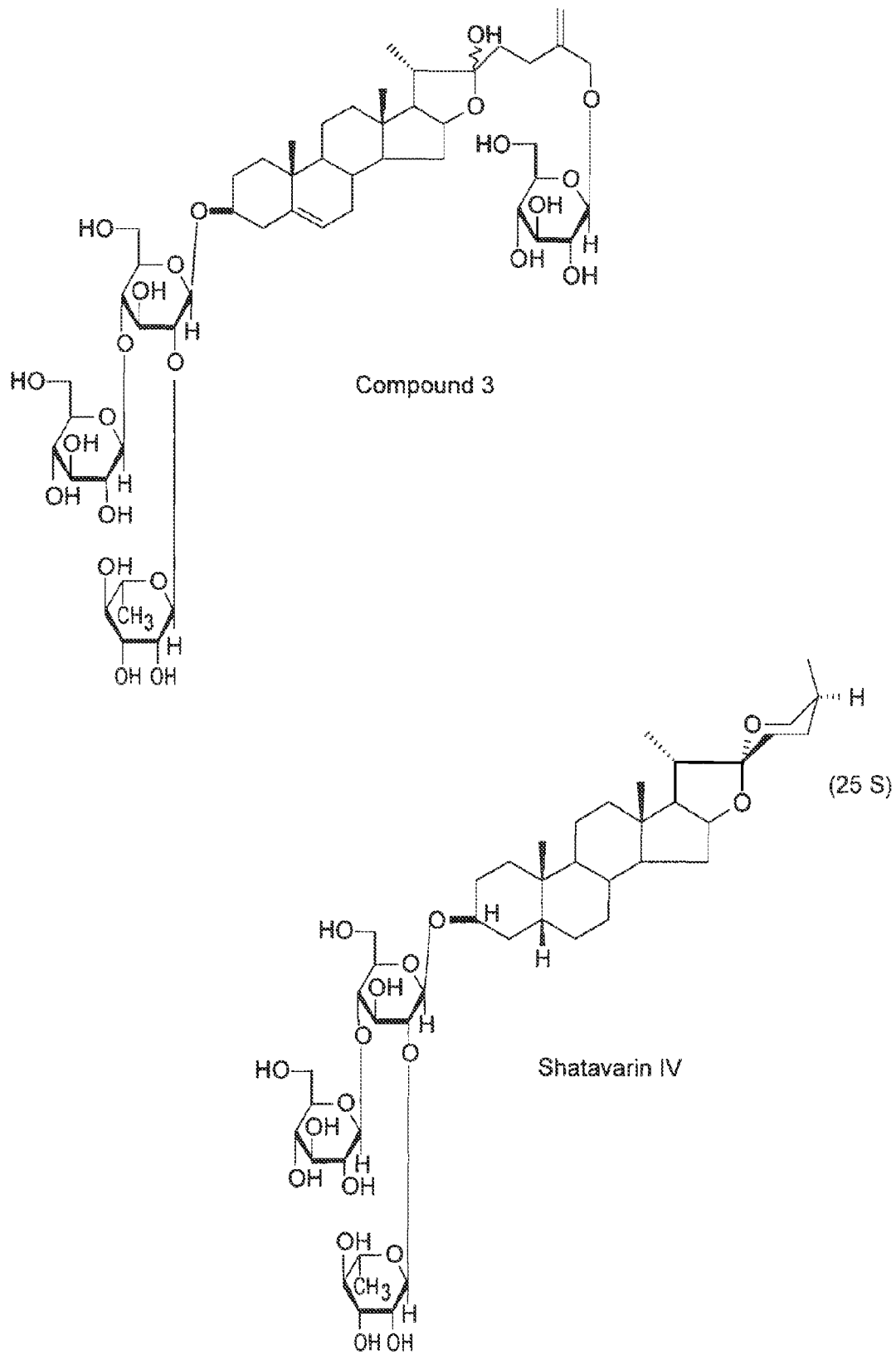
Compound 3
Shatavarin IV

FIG. 16 (Continue)
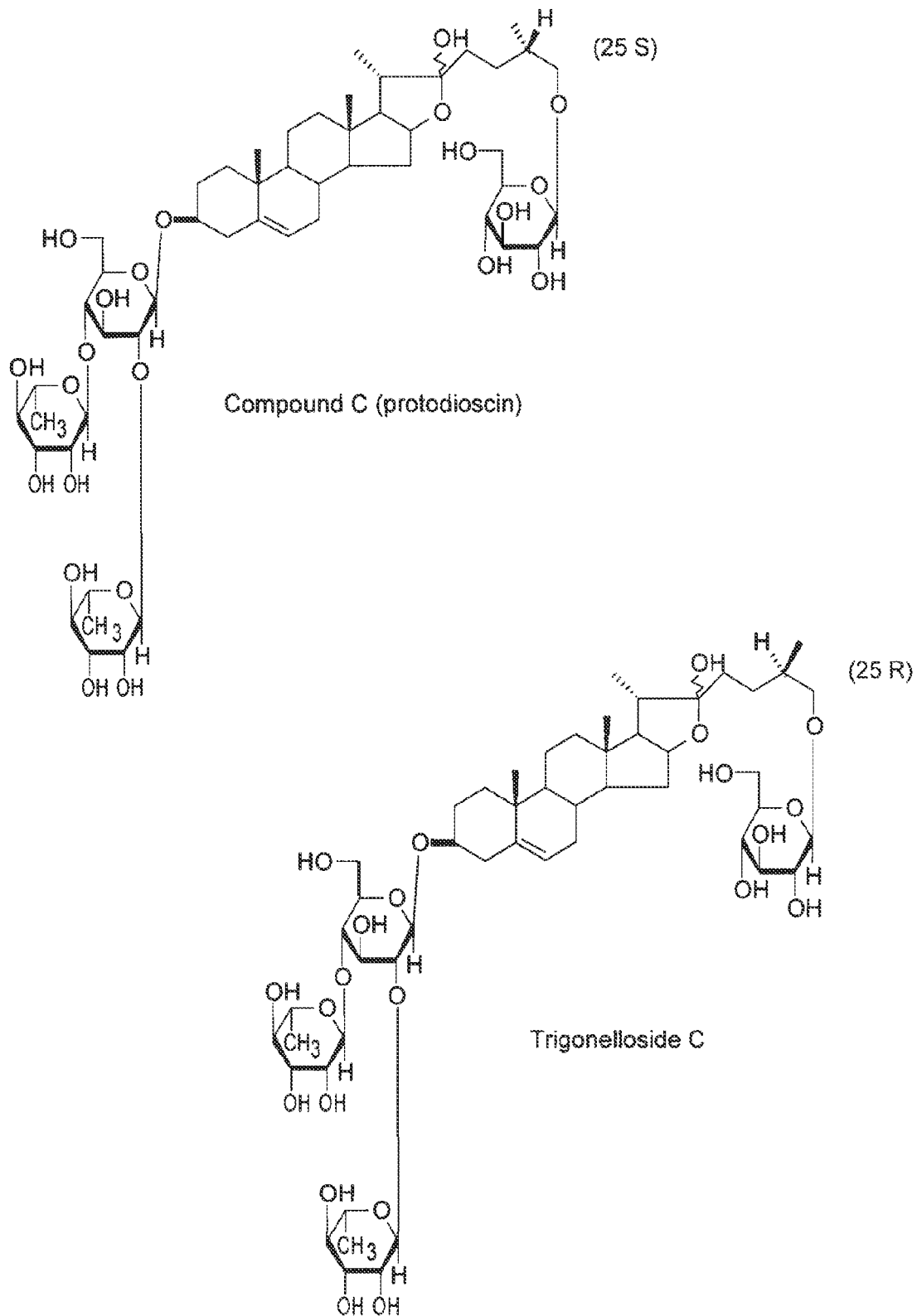

Protogracillin

Gracillin

CORE 2 GLCNAC-T INHIBITORS

This application is a continuation of Application No. 11/980,727, filed Oct. 31, 2007, now abandoned which is a continuation-in-part of Application No. 10/584,470, filed Aug. 9, 2006 now U.S. Pat. No. 7,906,493, and is a continuation-in-part of Application No. 11/472,554, filed Jun. 22, 2006, and is a continuation-in-part of Application No. 11/481,255, filed Jul. 6, 2006, and is a continuation-in-part of Application No. 11/481,256, filed Jul. 6, 2006, the entire content of which is hereby incorporated by reference in this application.

The present invention relates to the use of known and novel compounds as inhibitors of UDP-GlcNAc:Galβ1,3Gal-NAc—R (GlcNAc to GalNAc) β-1,6-N-acetylglucosaminyl transferase (core 2 β-1,6 N-acetylaminotransferase, core 2 GlcNAc-T-EC 2.4.1.102). The present invention relates to the use of known and novel compounds as pharmaceutical actives against diseases susceptible to treatment by modulation, eg. inhibition, of Core 2 GlcNAc-T.

Inhibitors of Core 2 GlcNAc-T, and the present compounds in particular, have application in therapy for diseases in which core 2 GlcNAc-T is implicated and especially those in which the enzyme activity is raised relative to the normal level in the tissue type concerned, or those conditions in which it is advantageous to lower the activity of core 2 GlcNAc-T for example to its normal level or below. Examples of such conditions are inflammatory diseases such as atherosclerosis and multiple sclerosis, diabetes, cancer including treatment or prevention of metastasis.

Inhibitors of Core 2 GlcNAc-T are known but none are in clinical development as isolated actives for pharmaceutical use. Examples of known compounds are disclosed in WO0187548, Kuhns et al., *Glycoconjugate Journal* 10 381-394 (1993), Hindsgaul et al., *J Biol. Chem.* 266(27):17858-62 (1991), and Told et al, *Biochem Biophys Res Commun.* 198 (2):417-23 (1994).

Applicant's co-pending application WO05/060977 (incorporated herein by reference) discloses known and novel steroidal glycosides that have therapeutic use as Core GlcNAc-T inhibitors, discusses the basis for use of such inhibitors in therapy and discloses published documents detailing the basis for Core 2 GlcNAc-T involvement in a number of diseases. Compounds of the formula IIb are not disclosed therein. The present application discloses further steroidal glycoside compounds that are inhibitors of core 2 GlcNAc-T and additional conditions in which these compounds have a therapeutic use.

The present inventors have determined that the compounds herein described can inhibit glucose-induced activity of core 2 GlcNAc-T and glucose induced binding of human leukocytes to cultured bovine retinal capillary endothelial cells as measured in assays described herein. The administration of these compounds, hereinafter referred to as Core 2 GlcNAc-T inhibitors to patients can prevent or treat the abnormal formation of core 2 O-glycans and sialyl Lewis$^x$ by inhibiting raised activity of core 2 GlcNAc-T in the aforementioned disease states.

Following initiation of glycosylation by the attachment of an N-acetylglucosamine (GalNAc) to either a serine or threonine residue in a protein to be glycosylated, processing proceeds by elongation, branching and then terminal modification of the O-glycans.

Essential steps in O-glycan elongation and branching are catalysed by multiple glycosyl transferase isoforms from families of homologous glycosyltransferases. Depending on which saccharide groups are subsequently attached to this first GalNAc residue, O-glycans are divided into four major subtypes (FIG. 1). The core 1 structure is formed by addition of galactose to form Galβ1-3GalNAc-αSer/Thr. The core 2 structure requires the core 1 structure as substrate and is formed by addition of GlcNAc to form Galβ1-3(GlcNAcβ1-6)GalNAc-αSer/Thr. The core 3 structure is formed by the addition of GlcNAc to form GlcNAcβ1-3GalNAc-αSer/Thr. The core 4 structure requires the core 3 structure as substrate and is formed by addition of GlcNAc to form GlcNAcβ1-3 (GlcNAcβ1-6)GalNAc-αSer/Thr. Other modifications to the core GalNAc structure have also been found, but appear to be uncommon. All these core structures are further modified by galactosylation, sialylation, fucosylation, sulfation or elongation to eventually form the O-glycan.

Three forms of Core 2 GlcNAc-T are known. Core 2 GlcNAc-T I identified in from leukemic cells, core 2 GlcNAc-T II identified in mucin secreting tissue, and a third thymus associated type designated core 2 GlcNAc-T III.

Cell surface O-glycans are known to play a crucial role in mediating cell-cell interactions in development and certain disease states. The patterns of protein glycosylation are determined largely by the activity and specificity of the glycotransferase enzymes, such as core 2 GlcNAc-T which is expressed in the Golgi apparatus (Colley K. J. *Glycobiology* 7, 1-13 (1997) Varki A. *Glycobiology* 3, 97-130 (1993)) Core 2 GlcNAc-T plays a crucial role in the biosynthesis of O-linked glycans (3-4) and represents an important regulatory step for the extension of O-linked sugars with polylactosamine (i.e. repeating Galβ1-4GlcNAcβ1-3), a structure associated with malignant transformation (Leferte S. *Cancer Res.* 48, 4743-4748 (1988) Ellies L. G. *Immunity* 9, 881-890 (1998)).

Changes in the activity of core 2 GlcNAc-T have been associated with various disease states, such as T-cell activation, cancers, metastasis, myeloblastic leukaemia, myocardial dysfunction and inflammation (Brockhausen I. et al. *Cancer Res.* 51, 1257-1263 (1991) Renkonen J., *APMIS* 109, 500-506 (2001) Machida E. et al., *Cancer Res.* 61, 2226-2231 (2001) Dalziel M. *Biol. Chem.* 276, 11007-11105 (2001) Perandio M., *Blood* 97, 3812-3819 (2001) Yousefi S., *J. Biol. Chem.* 266, 1772-1782 (1991) Higgins E. A., *J. Biol. Chem.* 266, 6280-6290 (1991) Piller F. *J. Biol. Chem.* 263, 15146-15150 (1988). Koya D. et al., *FASEB J.* 13, 2329-2337 (1999) Nishio Y. *J. Clin. Invest.* 96, 1759-1767 (1995) Tsuboi S., *Bioassays* 23, 46-53 (2001) Tsuboi S., *EMBO J.* 16, 6364-6373 (1997)). Regulation of core 2 GlcNAc-T is thought to be particularly important, because addition of lactosamine structures to the basic core oligosaccharides formed by this enzyme and subsequent modification with fucose and sialic acid, results in the formation of the Lewis$^x$, sialyl-sialyl Lewis$^a$, and Lewis$^x$ sugar groups that constitute the ligands of selectins which are cell adhesion proteins. This selectin-ligand interaction plays an important role in many processes.

Inflammation is how the body generally responds to infection or to some other form of trauma. One of the major events during inflammation is the movement of cells of the immune system from the blood stream to the infected or injured area. Once at the site of injury, these cells are responsible for the isolation, destruction and removal of the offending agent.

Acute inflammation, characterised by short duration (minutes to days), is essential for health, but sometimes the inflammatory process does not end when appropriate, and it is this that causes problems. Chronic inflammation is characterised by long duration (days, weeks, months and even years), lymphocytes and macrophages, tissue destruction and repair, and vascular proliferation and fibrosis. Inflammation can also be triggered inappropriately by the body's normal constituents and plays a role in common diseases, such as asthma, rheumatoid arthritis and inflammatory bowel disease.

Many cell adhesion molecules are known to be involved in the process of inflammation. At the site of inflammation, leukocytes first adhere to the vascular endothelial cells prior to the extravasation process. It is postulated that selectins play a crucial role in the initial adhesion of leukocytes to endothelial cells. Cell adhesion mediated by selectins and their carbohydrate ligands leads to the tethering and rolling of leukocytes on endothelial linings. This then leads to the secondary firm adhesion. Within hours of the initial stimulus, neutrophils begin to enter the tissue and may continue transmigration for many days. In some inflammatory conditions, tissue damage is caused by direct injury of the vessels and amplified by the subsequent recruitment of neutrophils into the tissue.

The expression of O-glycans reduces cell-cell interactions because of the bulkiness of these adducts. The expression of core 2 O-glycans is regulated by the transcriptional levels of core 2 GlcNAc-T in all of these cases. Antigen-mediated activation of peripheral T and B-cells is characterised by increased activity of core 2 GlcNAc-T and branched O-glycans on CD43 (leukosialin) (Tsuboi S., *Bioassays* 23, 46-53 (2001) Piller F. et al., *J. Biol. Chem.* 263, 15146-15150 (1988)).

Leukocyte extravasation, lymphocyte trafficking and other processes involve O-glycan synthesised by core 2 GlcNAc-T. Specifically, cell-surface O-glycan structures terminating in sialyl Lewis$^x$ are involved, in the recruitment of leukocytes to the site of inflammation. Core 2 GlcNAc-T is not important for T-cell development, but over expression of this enzyme has been shown to completely block the development of myeloid lineages.

Over expression of core 2 O-glycans has also been reported to affect the interaction between T-cells and B-cells (TB interaction). This T-B interaction is crucial for humoral immune response and is mediated through binding of the CD40 ligand (CD40L) on T-cells with CD40 on B-cells (CD40L-CD40 interaction). This interaction induces the proliferation of B-cells. Over expression of core 2 O-glycans has been shown to cause significant reduction in CD40L-CD40 interaction (Tsuboi S., *J. Biol. Chem.* 273(46), 30680-30687 (1998)).

It is possible to effectively block the initial step of leukocyte invasion from taking place, by blocking the synthesis of sialyl Lewis$^x$ on the cell surface of activated leukocytes and thereby halting their interactions with selectins. Therefore, inhibitors of core 2 GlcNAc-T that can reduce the activity of core 2 GlcNAc-T have utility in modulating inflammation.

Atherosclerosis is a progressive inflammatory disease of unknown mechanism. Recruitment and adhesion of circulating leukocytes to the endothelium particularly at arterial branches and bifurcations is one of the earliest events known to occur in atherogenesis. Integrins on the leukocytes then cause a stronger attachment between the cells. Leukocytes transmigrate through into the sub-endothelial space where they begin to accumulate in the intima. Monocytes become converted to activated macrophages with the presence of oxidised low density lipoprotein (LDL-oxLDL), these activated macrophages take up the modified types of lipoprotein via their scavenger receptors and differentiate to become foam cells. Histological analysis of atherosclerotic coronary arteries from patients who died of acute coronary syndromes demonstrate foam cells, macrophages, lymphocytes and mast cells were present in unstable or ruptured plaques (Mulvihill N. T. Heart. 87(3):201-4. (2002)).

At least three leukocyte adhesion molecules, E-selectin, ICAM-1, and VCAM-1, have been identified in human atherosclerosis (Guray U. et al. Int J Cardiol. 2004 96(2):235-40. O'Brien K D Circulation. 15; 93(4):672-82. (1996).). Further, in contrast to normal vessels, P selectin is overly expressed by epithelial cells in atherosclerotic lesions and expression of E-selectin and ICAM-1 (Davies M J. J Pathol. 171(3):223-9 (1993).) at the arterial lumen, has been found to be increased in arterial segments with mononuclear leukocyte accumulation. A third adhesion molecule, VCAM-1, has been detected in animal models of atherosclerosis, and also has been shown to be more prevalent in the intima of atherosclerotic plaques than in non atherosclerotic segments of human coronary arteries.

Chibber et al (Chibber R; Diabetes; 49(10):1724-30 (2000).) evaluated the importance of core 2 GlcNAc-T in increased leukocyte-endothelial cell adhesion and found significant increases in the activity of this enzyme in leukocytes of diabetic patients. However, until now there has been no evidence that core 2 GlcNAc-T activity is raised in circulating leukocytes of patients suffering from atherosclerosis. The applicants have now demonstrated that activity of the enzyme Core 2 GlcNAc-T is indeed raised in circulating leukocytes from patients with atherosclerosis, suggesting that compounds capable of lowering the activity of core 2 GlcNAc-T would be useful in the treatment or prevention of atherosclerosis or in preventing reoccurrence of atherosclerotic plaques in patients following interventions.

Although the clinical symptoms of diabetic cardiomyopathy have been identified, its pathogenesis is uncertain. The definition of diabetic cardiomyopathy describes both specific defects in the diabetic's myocytes, such as fibrosis leading to myocardial hypertrophy and diastolic dysfunction, and associated changes in the heart which have developed during the course of diabetes.

There is now strong evidence suggesting that raised activity of core 2 GlcNAc-T is directly responsible for elevated glycoconjugates, commonly observed in the heart tissue of diabetic animals and patients. In support of this, it has recently been shown that increased core 2 GlcNAc-T activity causes pathology similar to that observed in the heart of diabetic patients after years with the condition, in the heart of diabetic experimental animal models. Studies were carried out using a transgenic mouse with core 2 GlcNAc-T expression driven by a cardiac myosin promoter. At 4 months, a marked hypertrophy of the left ventricle and general hypertrophy of the heart was observed (Nishio Y., *J. Clin. Invest.* 96, 1759-1767 (1995) Tsuboi S, *Bioassays* 23, 46-53 (2001)).

Marked changes in core 2 branching and core 2 GlcNAc-T activities are associated with malignant transformation, leukaemia and carcinomas (Tsuboi S. *J. Biol. Chem.* 273(46), 30680-30687 (1998) Saitoh O., *Cancer Res.* 51(11), 2854-2862 (1991) Brockhausen I., *Cancer Res.* 51, 1257-1263 (1991) Renkonen J., *APMIS* 109, 500-506 (2001) Shimodaira K., *Cancer Res.* 1; 57(23), 5201-5216 (1997)). Rat fibroblasts and mammary carcinoma cells transfected with T24H-ras express core 2 O-glycans as they become metastatic tumours.

There is a great deal of evidence pointing to the involvement of core 2 GlcNAc-T in cancer and cancer metastasis. For example, highly metastatic colonic carcinoma cells both express more sialyl Lewis$^x$ than their low metastatic counterparts and adhere more strongly to E-selectin than poorly metastatic cells. There is a strong correlation between the expression of sialyl Lewis$^x$ in tumour cells and tumour progression (Brockhausen I, ibid). Moreover, a good correlation exists between the expression of sialyl Lewis$^x$ in core 2 O-glycans and lymphatic and venous invasion.

Recent findings suggest that core 2 GlcNAc-T in combination with α-1,3-Fuc-T contributes to the selectin-mediated metastasis in oral cavity carcinomas (Renkonen J., *APMIS*

109, 500-506 (2001)). Moreover, Western blot analysis revealed the presence of a major approximately 150 kDa glycoprotein that carries a-linked oligosaccharides recognised by anti-sLe$^x$ monoclonal antibody in sLe$^x$-positive pre-B leukaemia cell lines. This correlation of core 2 GlcNAc-T with CD15 expression suggests that core 2 GlcNAc-T is a regulator of the cell surface expression of sialyl Lewis$^x$ in human pre-B lymphoid cells. These results indicate that core 2 GlcNAc-T mRNA detected by in situ hybridisation reflects the malignant potentials of pulmonary adenocarcinoma, because lymph node metastasis is the most affecting factor to the patient's prognosis.

Expression of sialyl Lewis$^x$ in mouse melanoma B16-FI by transfection with the enzyme 1,3-fucosyltransferase have also confirmed the importance of sialyl Lewis$^x$ in tumour metastasis. Intravenous injection of the transfected cells into mice formed a large number of lung tumour nodules, while the parent B16-FI cells scarcely formed tumours.

The expression of sialyl Lewis$^a$, sialyl Lewis$^x$ (both selectin ligand carbohydrate structures) and raised activity of core 2 GlcNAc-T are all closely associated with malignancy of colorectal cancer (Numahata K., *Blood* 82(9), 2797-805 (2002))

Recently, Numahata demonstrated that sialyl Lewis$^x$ expression in primary bladder carcinoma is a predictor of invasive and metastatic outcome. No other carbohydrate epitope examined to date has equal prognostic value. Recently US 2004/0033521 disclosed that core 2b GlcNAc-T is over expressed in both liver and stomach tumours and in colon cancer and liver metastasis samples. Furthermore, WO 04/093662 demonstrates that core 2 GlcNAc-T is raised in prostate cancer testicular and bladder cancer. Levels of core 2 GlcNAc-T increase with increasing chance of metastasis or recurrence of disease.

Accordingly inhibitors of core 2 GlcNAc-T would be expected to reduce the production of the O-glycans, for example those bearing sialyl Lewis$^x$, and would reduce cancer invasiveness and metastasis and be useful in treatment of cancers where core 2 GlcNAc-T expression is raised above normal levels for that tissue type.

Diabetic retinopathy is a progressive vision threatening complication of diabetes (Klein R., *Arch. Opthalmol.* 107, 244-250 (1989)) characterised by capillary occlusion, formation of microvascular lesions and retinal neovascularisation adjacent to ischaemic areas of the retina (Davis M. D., *Diabetes Care* 15, 1844-1873 (1993) Kohner E. M. in *Diabetic Angiopathy*, ed. Tooke J. E., pages 233-247, Oxford University Press (1999)).

It has recently been found that raised activity of core 2 GlcNAc-T is directly responsible for increased leukocyte-endothelial cell adhesion and capillary occlusion in diabetic retinopathy (Chibber R. et al., *Diabetes* 49, 1724-1730 (2000)). It has now also been demonstrated that elevated glucose and diabetic serum increase the activity of core 2 GlcNAc-T and the adhesion of human leukocytes to endothelial cells. This occurs through PKCβ2-dependent phosphorylation of core 2 GlcNAc-T (Koya D., *Diabetes* 47, 859-866 (1998), Meier M. et al., *Vasc. Med.* 5, 173-185 (2000)). This regulatory mechanism involving phosphorylation of core 2 GlcNAc-T is also present in polymorphonuclear leukocytes (PMNs) isolated from Type 1 and Type 2 diabetic patients.

Inhibition of PKCβ32 activation by the specific inhibitor, LY379196, attenuates serine phosphorylation of core 2 GlcNAc-T, prevents the increase in activity and thus prevents increased leukocyte-endothelial cell adhesion. Such an inhibitor provides validation that reduction of core 2 GlcNAc-T activity provides a method of preventing increased leukocyte-endothelial cell adhesion and preventing capillary occlusion in retinopathy associated with diabetes or hyperglycaemia.

Fenugreek has been used for thousands of years for the treatment of diabetes. The plant contains many active ingredients, such as coumarins, saponins and glycosides, Many studies (44) have demonstrated the hypoglycaemic properties of fenugreek in both animals and humans. The hypoglycaemic properties have been attributed to the amino acid 4-hydroxyisoleucine which has potent insulinotropic activity (Broca C, *Eur. J. Pharmacol.* 390(3), 339-345 (2000), Sauvaire Y., *Diabetes* 47(2), 206-210 (1998)).

Some of the presently disclosed steroidal glycosides have been tested previously in a limited number of disease paradigms. For example in protection against gastric mucosal lesions in rats (Matsuda H et al *Bioorg Med Chem. Lett.* 24; 13(6):1101-6, 2003), in mouse ear edema tests for anti inflammatory activity (Kim et al *Arch Pharm Res.* 22(3): 313-6 (1999)), in treatment of dementia (U.S. Pat. No. 6,593, 301) as "immuno-modulators" and spermatogenesis and ovulation stimulators (Vasil'eva and Paseshnichenko Adv. Exp. Med. Biol. 404, 15-22 (1996)) and as adjuvants (Oda et al *Biol. Chem.* 381(1):67-74 (2000)). Compounds of the invention have also been used in in vitro cytotoxicity assays (e.g. Hu et al Planta Medica, 63(2), 161-165 (1997), Mimaki et al Phytochemistry 37(1):227-32 (1994), Akhov et al Proc. *Phytochem. Soc. Euprope* 45, 227-231 (2000) Hernandez, J. C. *Bioorganic & Medicinal Chemistry* 12(16), 4423-4429 (2004), Mimaki Y. et al *Natural Product Letters*, 14(5), 357-364 (2000), Dong M. et al *Planta Med.* 67(9):853-7 (2001), Nakamura O. et al Phytochemistry. 36(2):463-7 (1994), Hu K. et al *Planta Med.* 62(6):573-5 (1996), Hu K and Yao X. *Anticancer Drugs*.12(6):541-7 (2001), Hu K and Yao X. *Phytother Res.* 17(6):620-6 (2003)), however cytotoxic concentrations in cell based assays are several orders of magnitude higher than those currently disclosed for inhibition of Core 2 GlcNAc-T activity. CN1243129 and CN1237583 disclose the use of certain compounds presently disclosed in cancer. None of the aforementioned publications discloses that certain steroidal glycosides are inhibitors of Core 2 GlcNAc-T.

Certain plant sterol compounds, some of which are used as dietary supplements, impede the uptake of cholesterol from the gut and consequently lower plasma LDL cholesterol. However these compounds are generally used in doses of several grams per day and are not known to be inhibitors of Core 2 GlcNAc-T.

The present invention also relates to treatments for and diagnosis of neuroinflammatory diseases and in particular multiple sclerosis (MS). Multiple sclerosis is a disease with a significant inflammatory component. Although this enzyme has been implicated in inflammation (WO 0031109), Orlacchio A. et al (1997) *J Neurol Sci.* 22; 151(2):177-83 discloses that the level of activity of Core 2 GlcNAc-T is reduced in lymphomonocytes from patients with both relapsing remitting and progressive MS.

The present inventors have now surprisingly determined that Core 2 GlcNAc-T activity is in fact significantly raised in leukocyte preparations containing peripheral blood mononuclear cells (PBMNC) and polymorphonuclear (PMN) leukocytes from sample patients with MS. As Core 2 based oligosaccharides are found inter alia as a component of the ligands of proteins that are thought to mediate aspects of cell adhesion during the inflammatory response this has implications for increased leukocyte infiltration of tissues in MS. As raised Core 2 GlcNAc-T contributes to increased adhesiveness of leukocytes, the present inventors have determined that lowering the activity of Core 2 GlcNAc-T should tend to normalise adhesiveness of leukocytes, reduce leukocyte extravasation and reduce neuro-inflammation and associated plaque in MS patients.

Thus, in a first aspect the present invention is provided a method of treating a subject in need of therapy for a condition involving detrimental activity of the enzyme core 2 GlcNAc-T, particularly raised activity, comprising administration of a therapeutically effective amount of an inhibitor of core 2 GlcNAc-T of formula I to a patient in need thereof

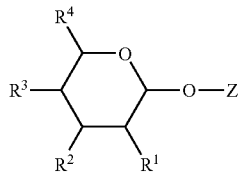

wherein $R^1$ is H, —OH, $C_{1-6}$ alkoxy, —$NR^5R^6$, or Sac 1; $R^2$ is H, —OH, $C_{1-6}$ alkoxy or Sac; $R^3$ is H, —OH, $C_{1-6}$ alkoxy or Sac 3; $R^4$ is H, $C_{1-6}$ alkyl, $C_{1-6}$ hydroxyalkyl or $C_{1-6}$-alkoxy-$C_{1-6}$-alkyl; $R^5$ is H, $C_{1-6}$ alkyl or $C_{1-6}$ acyl; $R^6$ is H, $C_{1-6}$ alkyl or $C_{1-6}$ acyl;

Sac 1, Sac 2 and Sac 3 are independently selected saccharide moieties attached to the ring through an oxygen; and Z is a steroid moiety attached to the oxygen shown by its 3 position ring carbon;

or a pharmaceutically acceptable salt, ether, ester or tautomeric form thereof. When one of $R^1$ to $R^3$ is a saccharide moiety, the ring of formula I is designated ring A.

preferably $R^1$, $R^2$ and $R^3$ are independently selected from H, —OH, or a saccharide moiety Sac 1, Sac 2 and Sac 3 respectively; more preferably $R^1$ is Sac 1; more preferably $R^2$ is —OH; more preferably $R^3$ is Sac 3;

preferably $R^4$ is H, $C_{1-6}$ alkyl or $C_{1-6}$ hydroxyalkyl; more preferably. $R^4$ is H, —$CH_2OH$ or —$CH_3$; more preferably still $R^4$ is —$CH_2OH$; more preferably still $R^4$ is —$CH_2OH$ and the resultant moiety is a glucose or galactose moiety; most preferably a glucose moiety;

preferably $R^5$ is H or $C_{1-6}$ alkyl; more preferably $R^5$ is H or —$CH_3$; most preferably $R^5$ is H;

preferably $R^6$ is H —$CH_3$ or —$COCH_3$; most preferably $R^6$ is —$COCH_3$; and Sac 1, Sac 2 and Sac 3 are attached to the ring through an oxygen; preferably Sac 1 Sac 2 and Sac 3 are independently selected from monosaccharide moieties and disaccharide moieties; preferably monosaccharide moieties; more preferably they are independently selected from a tetrose a pentose and a hexose. Preferably Sac 1 is selected from a pentose, a deoxy-aldohexose and an aldohexose; more preferably Sac 1 is selected from arabinose, xylose, glucose, mannose, galactose, and a deoxy-aldohexose; more preferably Sac 1 is selected from arabinose, xylose, glucose, mannose, galactose, and a 6-deoxyaldohexose; more preferably Sac 1 is selected from. glucose, galactose, arabinose, xylose and rhamnose; most preferably it is rhamnose;

Preferably Sac 2 is selected from a pentose, a deoxy-aldohexose and an aldohexose; more preferably Sac 2 is selected from arabinose, xylose, glucose, mannose, galactose, and a deoxyaldohexose; more preferably Sac 2 is selected from arabinose, xylose, glucose, mannose, galactose, and a 6-deoxyaldohexose; more preferably Sac 2 is selected, from glucose, galactose, arabinose, xylose and rhamnose;

Preferably Sac 3 is selected from a pentose, a deoxy aldohexose and an aldohexose; more preferably Sac 3 is selected from arabinose, xylose, quinovose rhamnose or an aldohexose, more preferably Sac 3 is selected from arabinose, xylose, quinovose, rhamnose, mannose, glucose and galactose, most preferably Sac 3 is rhamnose or glucose; and Z is a steroid moiety;

or a pharmaceutically acceptable salt, ether, ester or tautomeric form thereof.

The prior art associates Core 2 GlcNAc-T (particularly through its involvement with branched oligosaccharide synthesis) with a number of conditions, accordingly the present inventors have determined that Core 2 GlcNAc-T modulation, particularly inhibition, may be used to treat inter alia, vascular diseases, (including complications of diabetes such as diabetic retinopathy and diabetic cardiomyopathy), autoimmune and acute or chronic inflammatory conditions. Particular conditions associated with this enzyme and thus subject to treatment by the present invention are myopathy, retinopathy, nephropathy, atherosclerosis, myocardial dysfunction, asthma, rheumatoid arthritis, inflammatory bowel disease, transplant rejection, ischemia reperfusion injury (eg stroke, myocardial ischemia, intestinal reperfusion e.g. after hemorrhagic shock), restenosis, ileitis, Crohn's disease, thrombosis, cholitis including for example ulcerative cholitis), lupus, frost bite injury, acute leukocyte mediated lung injury (eg adult respiratory distress syndrome), traumatic shock, septic shock, nephritis, psoriasis, cholicytitis, cirrhosis, diverticulitis, fulminant hepatitis, gastritis, gastric and duodenal ulcers, hepatorenal syndrome, irritable bowel syndrome, jaundice, pancreatitis, ulcerative cholitis, human granulocyte ehlichiosis, Wiskott-Aldrich syndrome, T-cell activation, AIDS, infection with viruses, bacteria, protozoa and parasites adapted to use particular core 2 derived glycans and cancer. Cancer metastasis is particularly treatable by the present method.

Cancers may include, for example, leukemias (for example myoblastic leukemia), lymphomas, melanomas, adenomas, sarcomas, and carcinomas of solid tissues; particularly cancers include prostate, testicular, mammary, pancreatic, cervical, uterine, kidney, lung, rectum, breast, gastric, thyroid, neck, cervix, bowel, salivary gland, bile duct, pelvis, mediastinum, urethra, bronchogenic, bladder, esophagus, colon, small intestine and sarcomas (eg. Kaposi's sarcoma) and adenomatous polyps. Particularly susceptible cancers for treatment are leukemia oral cavity carcinomas, pulmonary cancers such as pulmonary adenocarcinoma, colorectal cancer, bladder carcinoma, liver tumours, stomach tumours colon tumours, prostate cancer, testicular tumour, mammary cancer, lung tumours oral cavity carcinomas. Particular application is found in cancer or its metastasis where Core 2 GlcNAc-T activity is raised. or is raised above normal levels for that tissue type. Preferably the compound of the formula I is a compound of the formula IIa or formula IIb

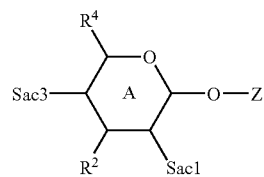

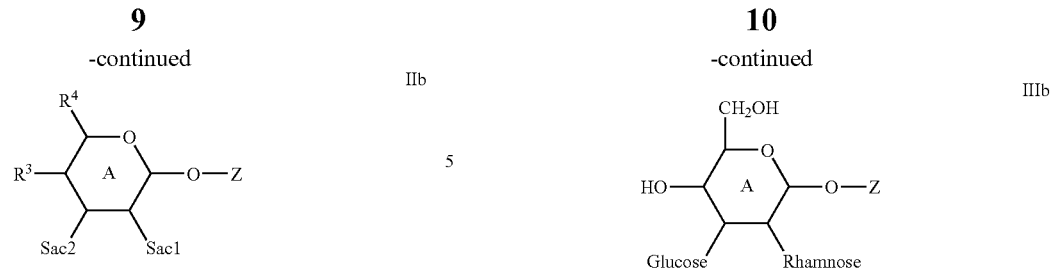

wherein

R² is H, —OH, or C₁₋₆ alkoxy; more preferably R² is H or —OH; R⁴ is as defined above; and Sac 1, Sac 2 and Sac 3 are independently selected saccharide moieties.

More preferred compounds are those of the formula IIa or IIb wherein R⁴ is H, —CH₂OH or —CH₃;

Particularly preferred still are those compounds wherein: R₄ is —CH₂OH;

More preferred still are those compounds wherein: R₄ is —CH₂OH and the moiety A is a glucose moiety;

In compounds of the formula IIb R³ is preferably H or —OH.

In a preferred combination, for compounds of the formula IIa, Ring A is either glucose or galactose; preferably glucose; Sac 1 is selected from glucose, galactose, arabinose, xylose and rhamnose and is preferably rhamnose; Sac 3 is selected from glucose, galactose, arabinose, xylose and rhamnose; preferably glucose.

In compounds of the formula III), saccharides Sac 1 and Sac 2 include, but are not limited to, monosaccharides, disaccharides, trisaccharides, tetrasaccharides and polysaccharides. Preferably Sac¹ and Sac² are monosaccharides, but may be independently selected as di- or oligosaccharides. Preferably Sac¹ and Sac² are independently selected from a tetrose a pentose and a hexose;

Preferably Sac 1 is selected from a pentose, a deoxy-aldohexose and an aldohexose; more preferably Sac 1 is selected from arabinose, xylose, glucose, mannose, galactose, and a deoxyaldohexose; more preferably Sac 1 is selected from the group consisting of arabinose, xylose, glucose, mannose, galactose, and a 6-deoxyaldohexose; more preferably Sac 1 is selected from. glucose, galactose, arabinose, xylose and rhamnose; more preferably it is rhamnose.

Preferably Sac 2 is selected from a pentose, a deoxy aldohexose and an aldohexose; more preferably Sac2 is selected from arabinose, xylose, quinovose rhamnose or an aldohexose, more preferably Sac2 is selected from the group consisting of arabinose, xylose, quinovose, rhamnose, glucose, mannose, gulose, altrose, allose idose and talose, more preferably still Sac2 is rhamnose or glucose; most preferably it is glucose.

In a preferred combination of formula IIb, the group A is glucose or galactose, Sac 1 is rhamnose and Sac 2 is arabinose, xylose, quinovose, rhamnose, glucose, mannose, galactose, altrose, allose idose and talose, more preferably is glucose or rhamnose. Most preferred are compounds of the formula I which are of the formula IIIa and formula IIIb:

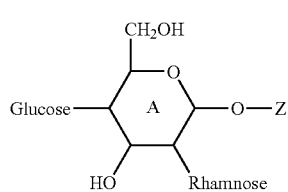

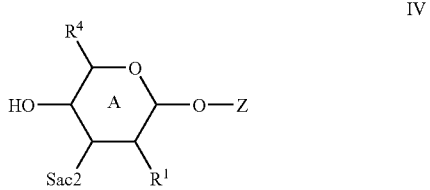

Wherein the ring A is a glucose moiety, and which formulae may be written

In which Rha represents rhamnose, Glc represents glucose and 2, 3 and 4 are the positions of ring A to which the saccharides are attached.

Most preferred are compounds which are 6-deoxy-α-L-mannopyranosyl-(1→2)-O-[β-D-glucopyranosyl-(1→4)]-β-D-glucopyranosides or 6-deoxy-α-L-mannopyranosyl (1→2)-O-[β-D-glucopyranosyl-(1→3)]-β-D-glucopyranosides respectively, of steroid moieties Z.

Alternatively compounds of the formula I are compounds of the formula IV:

wherein:

wherein R¹ is H, —OH, C₁₋₆ alkoxy, —NR⁵R⁶, or Sac 1; preferably R¹ is —OH, C₁₋₆ alkoxy or —NR⁵R⁶; more preferably R¹ is —NR⁵R⁶R³ is H, —OH or C₁₋₆ alkoxy; preferably R³ is H or —OH R⁴ and Sac2 are as defined above;

Preferred compounds of the formula N are compounds in which:

R¹ is —OH, C₁₋₆ alkoxy or NR⁵R⁶; R⁴ is H, C₁₋₆ alkyl or C₁₋₆ hydroxyalkyl; Sac 2 is glucose, galactose, arabinose, xylose and rhamnose More preferred compounds of the formula IV are those in which: R¹ is —NH—C₁₋₆-acyl; R⁴ is —CH₃ or —CH₂OH; Most preferred are the compounds of the formula IV which are of the formula Galβ1→3(6-deoxy)GalNAcα-Z The term "steroid moiety" denotes a moiety comprising a tetracyclic ring system shown as formula V:

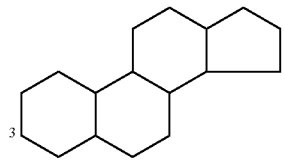

V

Typically the steroid moiety ring system is modified, for example by the addition of one or more further rings and/or one or more double bonds and/or one or more substituents. Typically the saccharide ring A is attached to the steroid moiety at the 3 position. The steroid moiety may for example have the ring system of cholestane, pregnane, androstane, estrane, cholesterol, cholane, progestin, a mineralocorticoid, such as dehydroepiandrosterone or its 7-keto or 7-hydroxy analogue or a bile acid.

In one preferred embodiment the steroid moiety is that of a steroid that is in itself beneficial or neutral. By neutral is meant that the steroid ring is that which is considered suitable, whether as approved eg. by the FDA or as GRAS, for use in a human or animal. By beneficial is meant that the steroid has effects of benefit to the human or animal if it were administered separately.

The steroid moiety Z may for example be that of a steroidal sapogenin derivable from natural sources (for example plant sources) or a steroidal moiety which is itself derivable from such steroidal sapogenins by chemical modification. The sapogenin may for example be that of a furostanol glycoside, a spirostanol glycoside (including those with nitrogen and oxygen containing rings) a damarane glycoside or other steroidal saponin. The steroid moiety Z for example may be a steroid moiety of the formula VI

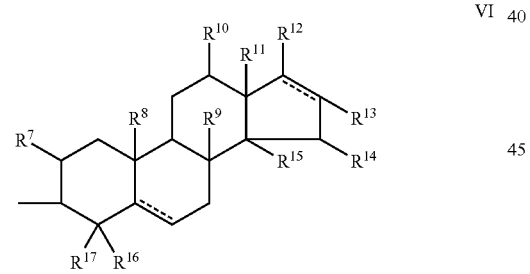

VI

Groups or rings that may be incorporated into the steroid core V or VI are selected from those set out in formulae VI a to VI e wherein the dotted lines represent the relevant rings of the steroid core.

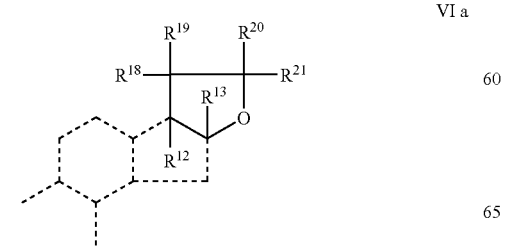

VI a

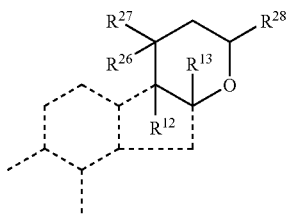

VI b

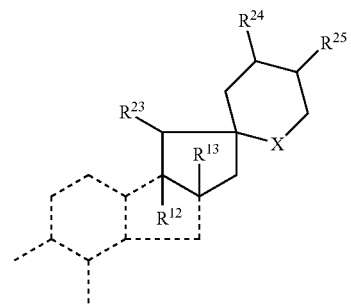

VI c

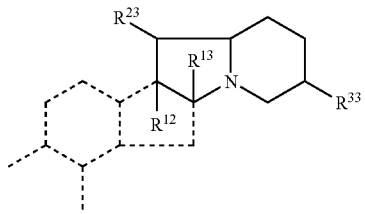

VI d

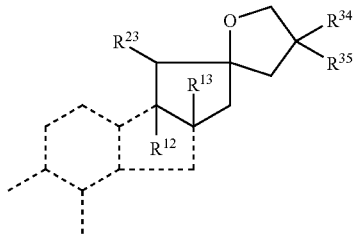

VI e wherein:

$R^7$, $R^{14}$, $R^{22}$ and $R^{24}$ are independently selected from H and —OH;

$R^8$, $R^{18}$, $R^{23}$, $R^{27}$ $R^{29}$ and $R^{33}$ are independently selected from $C_{1-6}$ alkyl; preferably $R^8$, $R^{18}$, $R^{23}$, $R^{27}$, $R^{29}$ and $R^{33}$ are —$CH_3$;

$R^9$, $R^{11}$ and $R^{16}$ are independently selected from H and $C_{1-6}$ alkyl; preferably $R^9$, $R^{11}$ and $R^{16}$ are independently selected from H and —$CH_3$;

$R^{10}$ is H or —OH or the H normally also present is absent and $R^{10}$ is =O;

$R^{12}$ is H, —OH or $C_{1-6}$ acyl or a group selected from VII a or VII b; preferably $R^{12}$ is H, —OH or acetyl or a group selected from VII a or VII b;

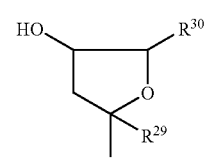

VII a

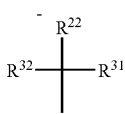

VIIb $R^{13}$ is H.

$R^{15}$ is H, $C_{1-6}$ alkyl or —OH or $R^{13}$ and $R^{15}$ taken together form a —$CH_2$—$CH_2$— group; preferably $R^{15}$ is H, —OH or —$CH_3$ or $R^{13}$ and $R^{15}$ taken together form a —$CH_2$—$CH_2$— group;

$R^{17}$ is H, $C_{1-6}$ alkyl or $C_{1-6}$ hydroxyallyl; preferably $R^{17}$ is H, —$CH_2OH$, or —$CH_3$. $R^{19}$ is H or —OH.

$R^{20}$ is H, —OH or $C_{1-6}$ alkoxy or $R^{19}$ and $R^{20}$ taken together represent the second bond of a double bond joining adjacent carbon atoms; preferably $R^{20}$ is H, —OH or —$OCH_3$ or $R^{19}$ and $R^{20}$ taken together represent the second bond of a double bond joining adjacent carbon atoms.

$R^{21}$ is $C_{1-6}$ alkyl, $C_{2-6}$ alkenyl, $C_{2-6}$ alkynyl or a $C_{1-6}$ alkyl or $C_{2-6}$ alkenyl group substituted by one or more groups selected from the group consisting of —OH, $C_{1-6}$ alkoxy and Sac 4; preferably $R^{21}$ is $C_{1-6}$ alkyl, $C_{2-6}$ alkenyl, $C_{2-6}$ alkynyl or a $C_{1-6}$ alkyl group substituted by one or more groups selected from the group consisting of —OH, $C_{1-6}$ alkoxy and Sac 4; more preferably $R^{21}$ is $C_{2-6}$ alkenyl, or a $C_{1-6}$ alkyl group substituted by one or more groups selected from the group consisting of —OH, $C_{1-6}$ alkoxy and Sac 4; more preferably $R^{21}$ is $C_{2-6}$ alkenyl or a $C_{1-6}$ alkyl group substituted by one or more groups selected from the group consisting of —OH, —$OCH_3$ and Sac 4; most preferably $R^{21}$ is selected from the group consisting of 3-methyl but-2-eneyl, 2-methyl-prop-2-enyl, 3-methylbutanyl substituted at the 4-position by Sac 4, 1-hydroxy-3-methylbutanyl substituted at the 4-position by Sac 4, or 1-methoxy-3-methylbutanyl substituted at the 4-position by Sac 4, In compounds of the formula I and particularly for compounds of the formula IIa $R^{21}$ may be 3-methylenebutyl substituted at the 4-position by Sac 4.

$R^{21}$ may be 4-hydroxy-3-methylbutanyl.

$R^{25}$ is $C_{1-6}$ alkyl, $C_{1-6}$ hydroxyalkyl or =$CH_2$; preferably $R^{25}$ is —$CH_3$, —$CH_2OH$ or =$CH_2$;

$R^{26}$ is —OH;

$R^{28}$ is $C_{1-6}$ alkyl, $C_{2-6}$ alkenyl or $C_{2-6}$ alkynyl; preferably $R^{28}$ is $C_{2-6}$ alkenyl; most preferably it is 2-methylprop-2-enyl $R^{30}$ is $C_{1-6}$ hydroxyalkyl;

$R^{31}$ is $C_{1-6}$ alkyl, $C_{1-6}$ hydroxyalkyl or $C_{1-6}$ alkyl substituted by Sac 5; preferably $R^{31}$ is $C_{1-6}$ alkyl or $C_{1-6}$ alkyl substituted by Sac 5; more preferably $R^{31}$ is —$CH_3$ or —$CH_2$-Sac 5.

$R^{32}$ is $C_{1-8}$ alkyl, $C_{2-8}$ alkenyl or $C_{2-8}$ alkynyl; preferably $R^{32}$ is $C_{1-8}$ alkyl or $C_{2-8}$ alkenyl; more preferably 3-ethyl-4-methyl-pentanyl or 5-methyl-hex-4-enyl;

$R^{34}$ is $C_{1-6}$ hydroxyalkyl or $C_{1-6}$ alkyl substituted by Sac 6; preferably $R^{34}$ is $C_{1-6}$ alkyl substituted by Sac 6; more preferably $R^{34}$ is —$C_{1-12}$-Sac 6;

$R^{35}$ is $C_{1-6}$ alkyl; preferably $R^{35}$ is —$CH_3$; and

Sac 4, Sac 5 and Sac 6 are independently selected saccharides; preferably Sac 4, Sac5 and Sac 6 are independently selected monosaccharides; more preferably they are independently selected a hexose, a pentose or a tetrose; more preferably still they are independently selected from glucose, galactose, quinovose, fucose, arabinose and xylose, most preferably they are glucose.

- - - - - Represents a bond that is either double or single; and

X is either O or NH; preferably X is O.

For compounds of the formula I and particularly of the formula IIa and IV the following preferences pertain.

Preferred steroid moieties Z that do not incorporate further groups VI(a) to VI(e) are those in which $R^9$ is $C_{1-6}$ alkyl; $R^{11}$ is H; and $R^{12}$ is VII(a); preferably $R^9$ is $C_{1-6}$ alkyl; $R^{11}$ is H; $R^{12}$ is VII(a); $R^{15}$ is $C_{1-6}$ alkyl and $R^{10}$ is H or —OH; more preferably $R^9$ is $C_{1-6}$ alkyl; $R^{11}$ is H; $R^{12}$ is VII(a); $R^{15}$ is $C_{1-6}$ alkyl; $R^{10}$ is H or —OH, $R^{16}$ is $C_{1-6}$ alkyl and $R^{17}$ is $C_{1-6}$ alkyl or $C_{1-6}$ hydroxyalkyl.

Further preferred steroid moieties Z that do not incorporate further groups VI(a) to VI(e) are those in which $R^9$ is $C_{1-6}$ alkyl; $R^{11}$ is H; and $R^{12}$ is VII(b); preferably $R^9$ is $C_{1-6}$ alkyl; $R^{11}$ is H; $R^{12}$ is VII(b) and $R^{16}$, $R^{17}$ and $R^{15}$ are $C_{1-6}$ alkyl; more preferably $R^9$ is $C_{1-6}$ alkyl; $R^{11}$ is H; $R^{12}$ is VII(b) and $R^{16}$, $R^{17}$ and $R^{15}$ are $C_{1-6}$ alkyl and $R^{10}$ is H or —OH.

Further preferred steroid moieties Z that do not incorporate further groups VI(a) to VI(e) are those in which $R^9$ is H; is $C_{1-6}$ alkyl; and $R^{12}$ is $C_{1-6}$ acyl; preferably $R^9$ is H; $R^{11}$ is $C_{1-6}$ alkyl; $R^{12}$ is $C_{1-6}$ acyl; $R^{16}$ and $R^{17}$ are H $R^{15}$ is H or —OH.

Further preferred steroid moieties Z that do not incorporate further groups VI(a) to VI(e) are those in which $R^9$ is H; $R^{11}$ is $C_{1-6}$ alkyl; and $R^{12}$ is VII b; preferably $R^9$ is H; $R^{11}$ is $C_{1-6}$ alkyl; $R^{12}$ is VIIb; $R^{16}$ and $R^{17}$ are H; and $R^{15}$ is H or —OH;

Preferred steroid moieties Z incorporating further groups VI a are those in which $R^9$ is H, $R^{11}$ is $C_{1-6}$ alkyl; $R^{12}$ is H or —OH; $R^{16}$ and $R^{17}$ are H and $R^{21}$ is a $C_{2-6}$ alkenyl group or a $C_{1-6}$ alkyl or $C_{2-6}$ alkenyl group substituted by one or more groups selected from the group consisting of —OH, —$OCH_3$ and Sac 4, preferably $R^{21}$ is a $C_{2-6}$ alkenyl group or a $C_{1-6}$ alkyl group substituted by one or more groups selected from the group consisting of —OH, —$OCH_3$ and Sac 4 preferably $R^8$ is $C_{1-6}$ alkyl and $R^9$ is H and $R^{11}$ is $C_{1-6}$ alkyl; $R^{12}$ is H or —OH; $R^{16}$ and $R^{17}$ are H and $R^{21}$ is 3-methyl but-2-eneyl, 2-methyl-prop-2-enyl, 3-methylbutanyl substituted at the 4-position by Sac4, 1-hydroxy-3-methylbutanyl substituted at the 4-position by Sac4, 1-methoxy-3-methylbutanyl substituted at the 4-position by Sac4, 3-methylenebutyl substituted at the 4-position by Sac 4, and 4-hydroxy-3-methylbutanyl.

Alternatively, steroid moieties Z incorporating further groups VI a are those in which $R^9$ is $C_{1-6}$ alkyl; $R^{11}$ is H; $R^{20}$ is H; and $R^{21}$ is a $C_{2-6}$ alkenyl; preferably $R^9$ is $C_{1-6}$ alkyl; $R^{11}$ is H; $R^{20}$ is H; $R^{21}$ is a $C_{2-6}$ alkenyl; and $R^{10}$ is H; more preferably $R^9$ is $C_{1-6}$ alkyl; $R^{11}$ is H; $R^{20}$ is H; $R^{21}$ is a $C_{2-6}$ alkenyl; $R^{10}$ is H; and $R^{15}$ is —OH or —$CH_2$—$CH_2$—; more preferably $R^9$ is $C_{1-6}$ alkyl; $R^{11}$ is H; $R^{20}$ is H; $R^{21}$ is a $C_{2-6}$ alkenyl; $R^{10}$ is H; $R^{15}$ is —OH or —$CH_2$—$CH_2$—; and $R^{16}$ and $R^{17}$ is $C_{1-6}$ alkyl.

Preferred steroid moieties Z incorporating further groups VI c are those in which $R^8$ is $C_{1-6}$ alkyl and $R^9$ is H and $R^{11}$ is $C_{1-6}$ alkyl; $R^{12}$ is H or —OH; $R^{15}$ is H or —OH; $R^{16}$ and $R^{17}$ are H; more preferred steroid moieties Z incorporating further groups VI c are those in which $R^8$ is $C_{1-6}$ alkyl and $R^9$ is H and $R^{11}$ is $C_{1-6}$ alkyl; $R^{12}$ is H or —OH; $R^{15}$ is H or —OH; $R^{16}$ and $R^{17}$ are H and X is O.

For compounds of the formula I of the formula IIb the following further preferences pertain.

Preferred steroid moieties Z that do not incorporate further groups VI(a) to VI(e) are those in which $R^9$ is $C_{1-6}$ alkyl; $R^{11}$ is H; and $R^{12}$ is VII(a); preferably $R^9$ is $C_{1-6}$ alkyl; $R^{11}$ is H; $R^{12}$ is VII(a); $R^{15}$ is $C_{1-6}$ alkyl and $R^{10}$ is H or —OH; more preferably $R^9$ is $C_{1-6}$ alkyl; $R^{11}$ is H; $R^{12}$ is VII(a); $R^{15}$ is $C_{1-6}$ alkyl; $R^{10}$ is H or —OH, $R^{16}$ is $C_{1-6}$ alkyl and $R^{17}$ is $C_{1-6}$ alkyl or $C_{1-6}$ hydroxyalkyl.

Further preferred steroid moieties Z that do not incorporate further groups VI(a) to VI(e) are those in which $R^9$ is $C_{1-6}$ alkyl; $R^{11}$ is H; and $R^{12}$ is VII(b); preferably $R^9$ is $C_{1-6}$ alkyl;

$R^{11}$ is H; $R^{12}$ is VII(b) and $R^{16}$, $R^{17}$ and $R^{15}$ are $C_{1-6}$ alkyl; more preferably $R^9$ is $C_{1-6}$ alkyl; $R^{11}$ is H; $R^{12}$ is VII(b) and $R^{16}$, $R^{17}$ and $R^{15}$ are $C_{1-6}$ alkyl and $R^{10}$ is H.

Further preferred steroid moieties Z that do not incorporate further groups VI(a) to VI(e) are those in which $R^9$ is H; $R^{11}$ is $C_{1-6}$ alkyl; and $R^{12}$ is $C_{1-6}$ acyl; preferably $R^9$ is H; $R^{11}$ is $C_{1-6}$ alkyl; $R^{12}$ is $C_{1-6}$ acyl; $R^{16}$ and $R^{17}$ are H; $R^{15}$ is H or —OH.

Further preferred steroid moieties Z that do not incorporate further groups VI(a) to VI(e) are those in which $R^9$ is H; $R^{11}$ is $C_{1-6}$ alkyl; and $R^{12}$ is VII b; preferably $R^9$ is H; $R^{11}$ is $C_{1-6}$ alkyl; $R^{12}$ is VIIb; $R^{16}$ and $R^{17}$ are H; and $R^{15}$ is H or —OH;

Preferred steroid moieties Z incorporating further groups VI(a) are those in which $R^9$ is H, $R^{11}$ is $C_{1-6}$ alkyl; $R^{12}$ is H or —OH; $R^{16}$ and $R^{17}$ are H and $R^{21}$ is $C_{2-6}$ alkenyl or a $C_{1-6}$ alkyl group substituted by one or more groups selected from the group consisting of —OH, —OCH$_3$ and Sac 4; preferably $R^9$ is H and $R^{11}$ is $C_{1-6}$ alkyl; $R^{12}$ is H or —OH; $R^{16}$ and $R^{17}$ are H and $R^{21}$ is selected from the group comprising 3-methyl but-2-eneyl, 2-methyl-prop-2-enyl, 3-methylbutanyl substituted at the 4-position by Sac 4,1-hydroxy-3-methylbutanyl substituted at the 4-position by $S^3$ or 1-methoxy-3-methylbutanyl substituted at the 4-position by Sac 4.

Further preferred steroid moieties Z incorporating further groups VI(a) are those in which $R^9$ is $C_{1-6}$ alkyl, and $R^{11}$ is H and $R^{21}$ is $C_{2-6}$ alkenyl; preferably $R^9$ is $C_{1-6}$ alkyl, $R^{11}$ is H, $R^{21}$ is $C_{2-6}$ alkenyl, $R^{16}$ and $R^{17}$ are $C_{1-6}$ alkyl; more preferably $R^9$ is $C_{1-6}$ alkyl, and $R^{11}$ is H, $R^{21}$ is $C_{2-6}$ alkenyl, $R^{16}$ and $R^{17}$ are $C_{1-6}$ alkyl; more preferably $R^9$ is $C_{1-6}$ alkyl, and $R^{11}$ is H, $R^{21}$ is $C_{2-6}$ alkenyl, $R^{16}$ and $R^{17}$ are $C_{1-6}$ alkyl; and $R^{19}$ is —OH.

Preferred steroid moieties Z incorporating further groups VI(c) are those in which $R^9$ is H, $R^{11}$ is $C_{1-6}$ alkyl, $R^{12}$ is H or —OH, $R^{15}$ is H or —OH; $R^{16}$ and $R^{17}$ are H.

For compounds of the formula I of the formula IIa, IIb or IV, preferred steroid moieties of formula VI a and VI b are those having the ring structures illustrated in FIG. 1 still more preferably having the substitutions as set forth therein. In each case the chiral centre at the carbon labelled "25" can be in either the R or S configuration.

More preferred steroid moieties, Z, of the formula VI c in which X=O are for example those having the radicals of sarsasapogenin, smilagenin, 12β-hydroxysmilagenin, rhodeasapogenin, isorhodiasapogenin, samogenin, 12β-hydroxysamogenin, markogenin, yonogenin, convallagenin A, convallagenin B, tokorogenin, tigogenin, neotigogenin, gitogenin, agigenin digitogenin, chlorogenin, paniculogenin, (25R)-spirostan-3β,17α,21-triol, allogenin, (25R)-5α-spirostan-2α,3β,5α,6α-tetraol, (24S,25R)-5α-spirostan-2α, 3β,5α,6β,24-pentaol, yamogenin diosgenin, yuccagenin, lilagenin, ruscogenin, (25S)-ruscogenin, neopraserigenin, pennogenin, isonuatigenin, cepagenin, 24a-hydroxypennogenin, ophiogenin, sibiricogenin, convallamarogenin, neoruscogenin, hecogenin, neohecogenin, manogenin, sisalagenin and hispigenin.

Preferred steroid moieties, Z, of the formula VI c in which X=NH are for example those that have the radicals of: solasodine, soladulcidine, tomatidine and 5-dehydrotomatidine.

Preferred steroidal moieties Z of the formula VI c are those having the ring structures illustrated in FIG. 2; still more preferably having the substitutions as set forth therein.

Further preferred steroidal moieties Z of the formula VI are those having the ring structures of FIG. 3; still more preferably having the substitutions as set forth therein.

Preferred steroid moieties VI i to VI xxxiii of FIG. 3 can be derived from steroidal glycoside compounds herein, of references of table 2 and additionally from the following references: Hostettman K. and Marston A (1995), *ibid.*, Mimaki et al *Phytochemistry* 37(1):227-32 (1994), Li et al *Phytochemistry* 29(12), 3893-8 (1990), Hernandez et al *bioorganic and med. chem.* 12(16) 4423-4429 (2004), Renault et al, *Phytochemistry,* 44(7), 1321-1327 (1997). Zheng et al *Steroids,* 69(2), 111-119 (2004), Yoshikawa et al. *Chemical & Pharmaceutical Bulletin,* 40(9), 2287-91 (1992), Yoshikawa. et al *Chemical & Pharmaceutical Bulletin,* 40(9), 2275-8 (1992), Chen. et al *Yunnan Zhiwu Yanjiu,* 9(4), 495-502 (1987), Fujita et al *Phytochemistry,* 38(2), 465-72 (1995), Yin et al *J. Nat. Products,* 67(6), 942-952 (2004), Sang *Phytochemistry,* 52(8), 1611-1615 (1999), Chen et al *Yunnan Zhiwu Yanjiu,* 6(1), 111-17 (1984), which are incorporated by reference and from On K. et al. *Phytochemistry.* 31(8):2767-75 (1992), Shimomura H. et al., Phytochemistry 28, 3163-3170 (1989).

Preferred compounds of the formula I combine preferred steroid moieties -Z- with preferred saccharide moieties.

In one embodiment compounds of the invention are those of the formula IIIa in which the steroid moiety -Z- is selected from group V which incorporate the further group VIa and in which $R^7$, $R^9$, $R^{10}$, $R^{13}$, $R^{14}$, $R^{16}$, $R^{17}$ and $R^{19}$ are H; $R^{12}$ is H or —OH; $R^8$, $R^{11}$ and $R^{18}$ are —CH$_3$; $R^{15}$ is H or —OH; $R^{20}$ is —OH or —OCH$_3$ and $R^{21}$ is 4-hydroxy-3-methylbutanyl, 3-methylenebutyl substituted at the 4-position by Glc, 3-methylbutanyl substituted at the 4-position by Glc, 1-hydroxy-3-methylbutanyl substituted at the 4-position by Glc or 1-methoxy-3-methylbutanyl substituted at the 4-position by Glc. It is particularly preferred that when $R^{21}$ is 3-methylenebutyl substituted at the 4-position by Glc then the compound of the formula IIIa is compound 25 of table 1a. and when $R^{21}$ is 4-hydroxy-3-methylbutanyl, then the compound of the formula IIIa is either compound 9 or compound 10 of table 1.

In certain embodiments the core 2 GlcNAc-T inhibitor preferably comprises a sugar-derived substituent. The term sugar-derived substituent means a saccharide, in which optionally one or more hydrogens and/or one or more hydroxyl groups have been replaced by —R, —OR, —SR, —NR wherein R is methyl, ethyl or propyl to form a derivative.

Saccharides include, but are not limited to, monosaccharides, disaccharides, trisaccharides, tetrasaccharides and polysaccharides.

Monosaccharides include, but are not limited to, arabinose, xylose, lyxose, ribose, glucose, mannose, galactose, allose, altrose, gulose, idose, talose, ribulose, xylulose, fructose, sorbose, tagatose, psicose, sedoheptulose, deoxyribose, fucose, rhamnose, 2-deoxy-glucose, quinovose, abequose, glucosamine, mannosamine, galactosamine, neuraminic acid, muramic acid, N-acetyl-glucosamine, N-acetyl-mannosamine, N-acetyl-galactosamine, N-acetylneuraminic acid, N-acetylmuramic acid, O-acetylneuraminic acid, N-glycolylneuraminic acid, fructuronic acid, tagaturonic acid, glucuronic acid, mannuronic acid, galacturonic acid, iduronic acid, sialic acid and guluronic acid.

Preferably, the core 2 GlcNAc-T inhibitor comprises at least one sugar-derived substituent; more preferably, the core 2 GlcNAc-T inhibitor comprises at least two sugar-derived substituents.

Preferably, each sugar-derived substituent is independently a mono-, di-, tri- or tetrasaccharide; more preferably, each sugar-derived substituent is independently a mono- or trisaccharide.

Preferably the core 2 GlcNAc-T inhibitor is a compound of the formula VIII

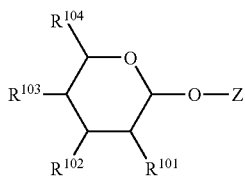

wherein $R^{101}$ is —OH, $C_{1-6}$ alkoxy, —$NR^{108}R^{109}$, or a monosaccharide of the formula:

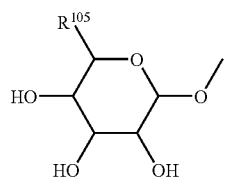

Preferably $R^{101}$ is —OH, —$NR^{108}R^{109}$, or a monosaccharide of the formula IXa; more preferably $R^{101}$ is —$NR^{108}R^{109}$, or a monosaccharide of the formula IXa; most preferably $R^{101}$ is a monosaccharide of the formula IXa;

$R^{102}$ is —OH, $C_{1-6}$ alkoxy or a monosaccharide of the formula IXb:

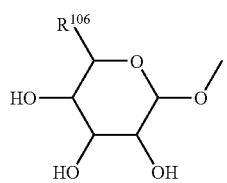

Preferably $R^{102}$ is —OH or a monosaccharide of the formula IXb; more preferably $R^{102}$ is —OH or a monosaccharide of the formula IXb; most preferably $R^{102}$ is —OH;

$R^{103}$ is —OH, $C_{1-6}$alkoxy or a monosaccharide of the formula IXc:

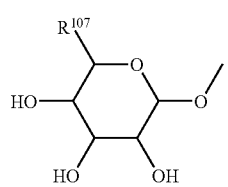

Preferably $R^{103}$ is —OH or a monosaccharide of the formula IXc; more preferably $R^{103}$ is a monosaccharide of the formula IXc; most preferably $R^{103}$ is glucose;

$R^{104}$ is $C_{1-6}$ alkyl, $C_{1-6}$ hydroxyalkyl or $C_{1-6}$-alkoxy-$C_{1-6}$-alkyl; preferably $R^{104}$ is $C_{1-6}$ alkyl or $C_{1-6}$ hydroxyalkyl; more preferably $R^{104}$ is —$CH_2OH$ or —$CH_3$; most preferably $R^{104}$ is —$CH_2OH$;

$R^{105}$ is $C_{1-6}$ alkyl, $C_{1-6}$ hydroxyalkyl or $C_{1-6}$-alkoxy-$C_{1-6}$-alkyl; preferably $R^{105}$ is $C_{1-6}$ alkyl or $C_{1-6}$ hydroxyalkyl; more preferably $R^{105}$ is —$CH_3$, —$C_2H_5$, —$CH_2OH$ or —$C_2H_4OH$; most preferably $R^{105}$ is —$CH_3$;

$R^{106}$ is $C_{1-6}$ alkyl, $C_{1-6}$ hydroxyalkyl or $C_{1-6}$-alkoxy-$C_{1-6}$-alkyl; preferably $R^{106}$ is $C_{1-6}$ alkyl or $C_{1-6}$ hydroxyalkyl more preferably $R^{106}$ is —$CH_2OH$ or —$CH_3$; most preferably $R^{106}$ is —$CH_2OH$;

$R^{107}$ is $C_{2-6}$ alkyl, $C_{1-6}$ hydroxyalkyl or $C_{1-6}$-alkoxy-$C_{1-6}$-alkyl; preferably $R^{107}$ is $C_{1-6}$ hydroxyalkyl or $C_{1-6}$-alkoxy-$C_{1-6}$-alkyl; more preferably $R^{107}$ is —$CH_2OH$ or $C_{1-6}$ alkoxymethyl; most preferably $R^{107}$ is —$CH_2OH$;

$R^{108}$ is H, $C_{1-6}$ alkyl or $C_{1-6}$ acyl; preferably $R^{108}$ is H or $C_{1-6}$ alkyl; more preferably $R^{108}$ is H or $CH_3$; most preferably $R^{108}$ is H;

$R^{109}$ is H, $C_{1-6}$ alkyl or $C_{1-6}$ acyl; preferably $R^{109}$ is H or $C_{1-6}$ acyl more preferably $R^{109}$ is H or —$COCH_3$; most preferably $R^{109}$ is —$COCH_3$; and Z is a steroid group;

or a pharmaceutically acceptable salt, ester or tautomeric form or derivative thereof.

In these embodiments preferably the compound of the formula VIII is a compound of the formula X:

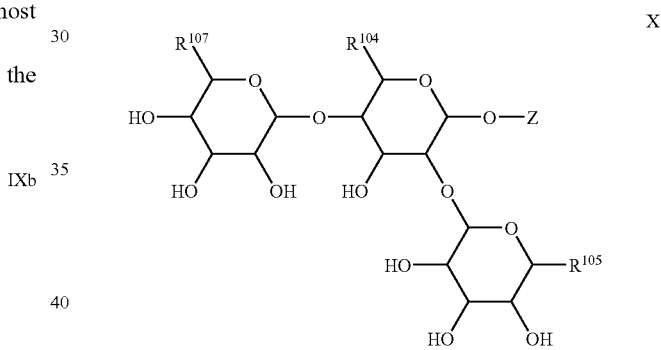

wherein:

$R^{104}$ is $C_{1-6}$ alkyl, $C_{1-6}$ hydroxyalkyl or $C_{1-6}$-alkoxy-$C_{1-6}$-alkyl; preferably $C_{1-6}$ alkyl or $C_{1-6}$ hydroxyalkyl more preferably —$CH_2OH$ or —$CH_3$; most preferably —$CH_2OH$;

$R^{105}$ is $C_{1-6}$ alkyl, $C_{1-6}$ hydroxyalkyl or $C_{1-6}$-alkoxy-$C_{1-6}$-alkyl; preferably $R^{105}$ is $C_{1-6}$ alkyl or $C_{1-6}$ hydroxyalkyl; more preferably $R^{105}$ is —$CH_3$, —$C_2H_5$, —$CH_2OH$ or —$C_2H_4OH$; most preferably $R^{105}$ is —$CH_3$; and $R^{107}$ is $C_{2-6}$ alkyl, $C_{1-6}$ hydroxyalkyl or $C_{1-6}$-alkoxy-$C_{1-6}$-alkyl; preferably $R^{107}$ is $C_{1-6}$ hydroxyalkyl or $C_{1-6}$-alkoxy-$C_{1-6}$-alkyl; more preferably $R^{107}$ is —$CH_2OH$ or $C_{1-6}$ alkoxymethyl; most preferably $R^{107}$ is —$CH_2OH$.

More preferred are compounds of the formula X wherein: $R^{104}$ is $C_{1-6}$ hydroxyalkyl or $C_{1-6}$ alkyl; $R^{105}$ is $C_{1-6}$ alkyl, $C_{1-6}$ hydroxyalkyl; and $R^{107}$ is $C_{1-6}$ hydroxyalkyl or $C_{1-6}$-alkoxy-$C_{1-6}$-alkyl.

More preferred are compounds wherein: $R^{104}$ is —$CH_2OH$ or —$CH_3$; $R^{105}$ is —$CH_3$; and $R^{107}$ is —$CH_3OH$.

Most preferred compounds of the formula X are compounds of the formula VIII wherein: $R^{101}$ is rhamnose; $R^{102}$ is —OH; $R^{103}$ is glucose; and $R^{104}$ is —$CH_2OH$.

Most preferred are compounds of the formula VIII which are of the formula IV:

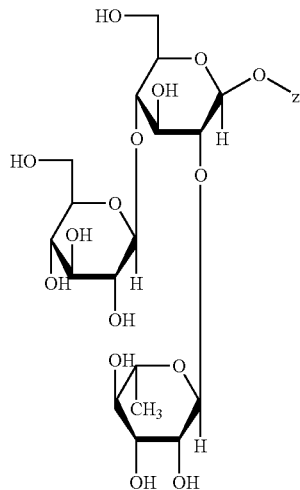

XI

Also provided are compounds wherein the compound of the formula VIII is a compound of the formula V:

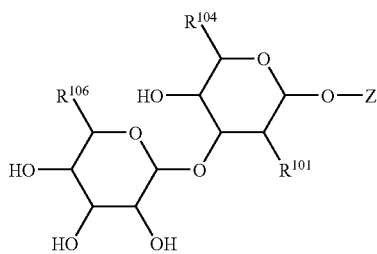

XII wherein:
$R^{101}$ is —OH, $C_{1-6}$ alkoxy or $NR^{108}R^{109}$, or a monosaccharide of the formula IXa:

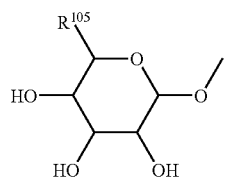

IXa

Preferably $R^{101}$ is —OH, or $NR^{108}R^{109}$, more preferably $R^{101}$ is $NR^{108}R^{109}$.

$R^{104}$ is $C_{1-6}$ alkyl, $C_{1-6}$ hydroxyalkyl or $C_{1-6}$-alkoxy-$C_{1-6}$-alkyl; preferably $R^{104}$ is $C_{1-6}$ alkyl or $C_{1-6}$ hydroxyalkyl more preferably $R^{104}$ is $C_{1-6}$ alky; most preferably —$CH_3$;

$R^{105}$ is $C_{1-5}$ alkyl, $C_{1-6}$ hydroxyalkyl or $C_{1-6}$-alkoxy-$C_{1-6}$-alkyl; preferably $R^{105}$ is $C_{1-6}$ alkyl or $C_{1-6}$ hydroxyalkyl; more preferably $R^{105}$ is —$CH_3$ or —$CH_2OH$; most preferably $R^{105}$ is —$CH_3$; and $R^{106}$ is $C_{1-6}$ alkyl, $C_{1-6}$ hydroxyalkyl or $C_{1-6}$-alkoxy-$C_{1-6}$-alkyl; preferably $R^{106}$ is $C_{1-6}$ alkyl or $C_{1-6}$ hydroxyalkyl more preferably $R^{106}$ is —$CH_2OH$ or —$CH_3$; most preferably $R^{106}$ is —$CH_2OH$;

$R^{108}$ is H, $C_{1-6}$ alkyl or $C_{1-6}$ acyl; preferably $R^{1138}$ is H or $C_{1-6}$ alkyl; more preferably $R^{108}$ is H or $CH_3$; most preferably $R^{108}$ is H;

$R^{109}$ is H, $C_{1-6}$ alkyl or $C_{1-6}$ acyl; preferably $R^{109}$ is H or $C_{1-6}$ acyl more preferably $R^{1139}$ is H or —$COCH_3$; most preferably $R^{109}$ is —$COCH_3$; and Z is a steroid group.

Preferred compounds of the formula XII are compounds in which $R^{101}$ is —OH, $C_{1-6}$ alkoxy or $NR^{108}R^{109}$; $R^{104}$ is $C_{1-6}$ alkyl or $C_{1-6}$ hydroxyalkyl; $R^{106}$ is $C_{1-6}$ alkyl or $C_{1-6}$ hydroxyalkyl; $R^{108}$ is H, $C_{1-6}$ alkyl or $C_{1-6}$ acyl; and $R^{109}$ is H, $C_{1-6}$ alkyl or $C_{1-6}$ acyl.

More preferred compounds of the formula XII are those in which $R^{101}$ is —NH—$C_{1-6}$-acyl; $R^{104}$ is $C_{1-6}$ alkyl or —$CH_2OH$; and $R^{106}$ is $C_{1-6}$ hydroxyalkyl.

Most preferred are the compounds of the formula IV which are of the formula:

Galβ1→3(6-deoxy)GalNAcα-Z

In one such embodiment the steroid group is a steroidal sapogenin of the formula VII:

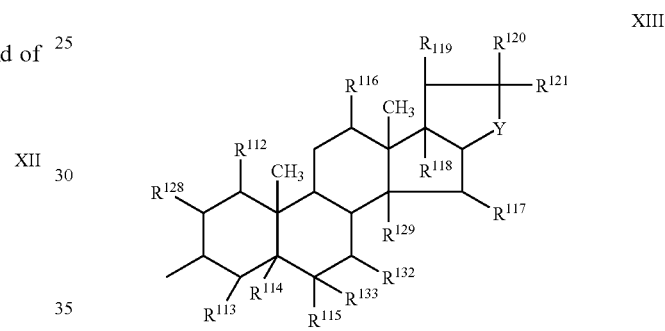

XIII wherein:
$R^{112}$ is H, OH, $C_{1-6}$ alkyl or $C_{1-6}$ alkoxy; preferably $R^{112}$ is H or —OH; most preferably $R^{12}$ is H;

$R^{113}$ is H, —OH, =O, or $C_{1-6}$ alkyl; preferably $R^{113}$ is H or —OH; most preferably $R^{113}$ is H;

$R^{114}$ is H, —OH or $C_{1-6}$ alkyl or $R^{114}$ and $R^{133}$ taken together represent the second bond of a double bond joining adjacent carbon atoms; preferably $R^{114}$ is H or $R^{114}$ and $R^{133}$ taken together represent the second bond of a double bond joining adjacent carbon atoms;

$R^{115}$ is H, or —OH, or $R^{115}$ and $R^{133}$ taken together are =O; preferably $R^{115}$ is H, or $R^{115}$ and $R^{133}$ taken together are =O; more preferably $R^{115}$ is H;

$R^{116}$ is H, OH or =O; preferably $R^{116}$ is H or =O; more preferably $R^{116}$ is H;

$R^{117}$ is H, OH or =O; preferably $R^{117}$ is H or —OH; more preferably $R^{117}$ is H;

$R^{118}$ is H, OH, $C_{1-6}$ alkoxy or $C_{1-6}$ alkyl; preferably $R^{118}$ is H, OH, $C_{1-6}$ alkoxy; more preferably $R^{118}$ is H or OH; most preferably $R^{118}$ is H;

$R^{119}$ is H, OH, $C_{1-6}$ alkyl or $C_{1-6}$ alkoxy; preferably $R^{119}$ is H, OH, $C_{1-6}$ alkyl; more preferably $R^{119}$ is H, OH or $C_{1-6}$ alkyl; most preferably $R^{119}$ is $C_{1-6}$ alkyl; and particularly $R^{119}$ is —$CH_3$;

$R^{120}$ is H, OH, $C_{1-6}$ alkoxy or $C_{1-6}$ alkyl; preferably $R^{120}$ is H, —OH, or $C_{1-6}$ alkoxy; more preferably $R^{120}$ is —OH or $C_{1-6}$ alkoxy; most preferably $R^{120}$ is —OH;

$R^{121}$ is H, OH, $C_{1-6}$ alkyl, $C_{1-6}$ alkoxy or is a group of the formula XIV:

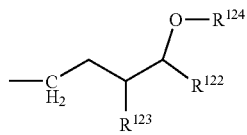

preferably $R^{121}$ is a group of the formula XIV;

$R^{122}$ is H, OH, $C_{1-6}$ alkyl or $C_{1-6}$ alkoxy; preferably $R^{122}$ is H, OH, or $C_{1-6}$ alkoxy; preferably $R^{122}$ is H or OH, —OCH$_3$ or —O—C$_2$H$_5$; most preferably $R^{122}$ is H;

$R^{123}$ is H, OH, $C_{1-6}$ alkyl, $C_{1-6}$ hydroxyallyl, $C_{1-6}$-alkoxy-$C_{1-6}$alkyl, =CH$_2$ or =CH—$C_{1-6}$-alkyl; preferably $R^{123}$ is $C_{1-6}$ alkyl, $C_{1-6}$ hydroxyalkyl, $C_{1-6}$-alkoxy-$C_{1-6}$-alkyl, =CH$_2$ or =CH—$C_{1-6}$-alkyl; more preferably $R^{123}$ is $C_{1-6}$ alkyl, $C_{1-6}$ hydroxyalkyl or =CH$_2$; most preferably $R^{123}$ is —C$_2$H$_4$OH, —CH$_2$OH, $C_{1-6}$ alkyl, or =CH$_2$, even more preferably $R^{123}$ is —C$_2$H$_4$OH, —CH$_2$OH, —C$_2$H$_5$, —CH$_3$ or =CH$_2$ and particularly $R^{123}$ is —CH$_3$ or =CH$_2$; and $R^{124}$ is H, $C_{1-6}$ alkyl, $C_{1-6}$ acyl or a monosaccharide Sac 7; preferably $R^{124}$ is $C_{1-6}$ alkyl, $C_{1-6}$ acyl or a monosaccharide Sac 7; more preferably $R^{124}$ is $C_{1-6}$ acyl or a monosaccharide SAC 7; most preferably $R^{124}$ is a monosaccharide SAC 7.

$R^{128}$ and $R^{129}$ are the same or different and are H or —OH; preferably $R^{128}$ is H and $R^{129}$ is —OH; more preferably both $R^{128}$ and $R^{129}$ are H;

$R^{132}$ is H, OH or =O; preferably $R^{132}$ is H or OH; most preferably $R^{132}$ is H; and $R^{133}$ is H, or $R^{133}$ and $R^{115}$ taken together are =O, or $R^{133}$ and $R^{114}$ taken together represent the second bond of a double bond joining adjacent carbon atoms; preferably $R^{133}$ is H or $R^{133}$ and $R^{114}$ taken together represent the second bond of a double bond joining adjacent carbon atoms;

Sac 7 is selected from a group consisting of arabinose, xylose, lyxose, ribose, glucose, mannose, galactose, allose, altrose, gulose, idose, talose, ribulose, xylulose, fructose, sorbose, tagatose, psicose, sedoheptulose, deoxyribose, fucose, rhamnose, 2-deoxy-glucose, quinovose, abequose, glucosamine, mannosamine, galactosamine, neuraminic acid, muramic acid, N-acetyl-glucosamine, N-acetyl-mannosamine, N-acetyl-galactosamine, N-acetylneuraminic acid, N-acetylmuramic acid, O-acetylneuraminic acid, N-glycolylneuraminic acid, fructuronic acid, tagaturonic acid, glucuronic acid, mannuronic acid, galacturonic acid, iduronic acid, sialic acid and guluronic acid; preferably Sac 7 is selected from a group consisting of glucose, galactose, mannose, fucose, N-acetyl-glucosamine, N-acetyl-galactosamine and sialic acid; most preferably Sac 7 is glucose; and Y is N or O; preferably Y is O.

Preferred steroidal sapogenins of the formula XIII are those in which $R^{121}$ is of the formula XIV and Y is O.

More preferred steroidal sapogenins of the formula XIII are those in which:

$R^{112}$ is H, —OH; $R^{113}$ is H or —OH; $R^{114}$ is H, or —OH or $R_{114}$ and $R1_{33}$ taken together represent the second bond of a double bond joining adjacent carbon atoms; $R^{115}$ is H, or $R_{115}$ and $R1_{33}$ taken together are =O; $R^{118}$ is H, —OH or $C_{1-6}$ alkoxy; $R^{119}$ is $C_{1-6}$ alkyl; $R^{129}$ is H, —OH or $C_{1-6}$ alkoxy; $R^{128}$ is H; $R^{132}$ is H, —OH or =O; and $R^{133}$ is H, or $R^{133}$ and $R^{115}$ taken together are =O, or $R^{133}$ and $R^{114}$ taken together represent the second bond of a double bond joining adjacent carbon atoms.

Most preferred are steroidal sapogenins of the formula XIII in which: $R^{112}$, $R^{113}$, $R^{115}$ and $R^{128}$ each represent H; $R^{114}$ is H, or $R^{114}$ and $R^{133}$ taken together represent the second bond of a double bond joining adjacent carbon atoms; $R^{116}$ is H, or =O; $R^{117}$ is H or —OH; $R^{118}$ is H or —OH; $R^{119}$ is H, or $C_{1-6}$ alkyl; $R^{120}$ is of the formula VIII; $R^{122}$ is H, —OH, or $C_{1-6}$ alkoxy; $R^{124}$ is $C_{1-6}$ alkyl, $C_{1-6}$ acyl, or glucose; $R^{129}$ is H or —OH; and $R^{132}$ is H or —OH.

The most preferred steroidal sapogenins of the formula XIII are those in which $R^{112}$, $R^{113}$, $R^{115}$, $R^{116}$, $R^{117}$, $R^{122}$, $R^{128}$ each represent H; $R^{114}$ is H, or $R^{114}$ and $R^{133}$ taken together represent the second bond of a double bond joining adjacent carbon atoms; $R^{120}$ is —OH or $C_{1-6}$ alkoxy; $R^{121}$ is of the formula XIV; $R^{123}$ is —CH$_3$ or =CH$_2$; $R^{124}$ is $C_{1-6}$ acyl or glucose; $R^{129}$ is H or —OH; and $R^{132}$ is H.

The most preferred steroidal sapogenins of the formula XIII are selected from the group consisting of:

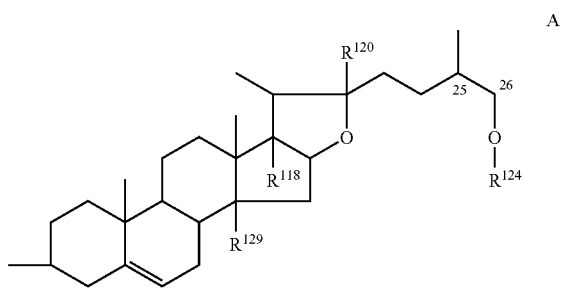

A

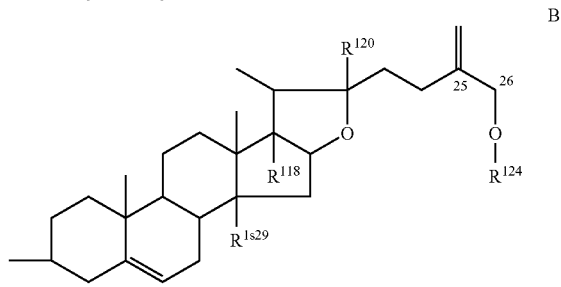

B

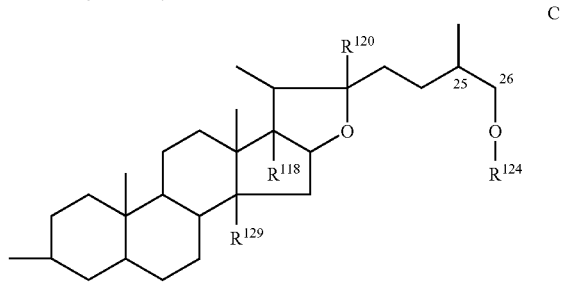

C

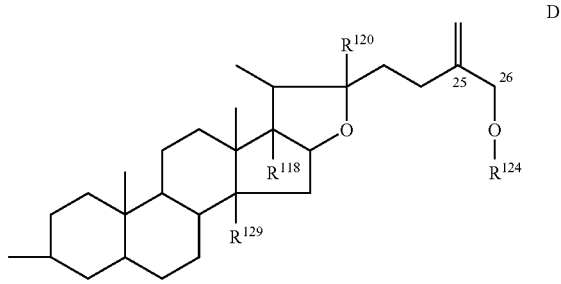

D wherein:
$R^{118}$ is H or OH; $R^{120}$ is OH or $C_{1-6}$ alkoxy; $R^{124}$ is glucose or $C_{1-6}$ acyl; and
$R^{129}$ is H or OH.

Particularly preferred compounds of the formula VIII in which the steroid group is of the formula XIII are trigoneoside IVa, glycoside F, shatavarin I, compound 3, pardarinoside C, whose structures are summarised in Table 1a.

Alternatively, the steroid group may be a steroidal sapogenin of the formula XV:

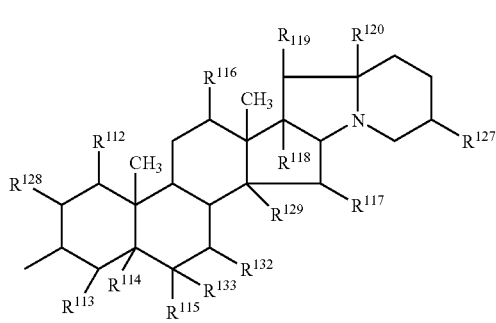

wherein:
$R^{112}$ is H, —OH, $C_{1-6}$ alkyl or $C_{1-6}$ alkoxy; preferably $R^{112}$ is H or —OH; most preferably $R^{112}$ is H;

$R^{113}$ is H, —OH, =O, or $C_{1-6}$ alkyl; preferably $R^{113}$ is H or —OH; most preferably $R^{113}$ is H;

$R^{114}$ is H —OH or $C_{1-6}$ alkyl or $R^{114}$ and $R^{13}_{3}$ taken together represent the second bond of a double bond joining adjacent carbon atoms; preferably $R^{114}$ is H or $R^{114}$ and $R^{133}$ taken together represent the second bond of a double bond joining adjacent carbon atoms;

$R^{115}$ is H, or —OH, or $R^{115}$ and $R^{133}$ taken together are =O; preferably $R^{115}$ is H, or $R^{115}$ and $R^{133}$ taken together are =O; more preferably $R^{115}$ is H;

$R^{116}$ is H, —OH or =O; preferably $R^{116}$ is H or =O; more preferably $R^{116}$ is H;

$R^{117}$ is H, —OH or =O; preferably $R^{117}$ is H or —OH; more preferably $R^{117}$ is H;

$R^{118}$ is H, —OH, $C_{1-6}$ alkoxy or $C_{1-6}$ alkyl; preferably $R^{118}$ is H, —OH, $C_{1-6}$ alkoxy; more preferably $R^{118}$ is H or OH; most preferably $R^{118}$ is H;

$R^{119}$ is H, —OH, $C_{1-6}$ alkyl or $C_{1-6}$ alkoxy; preferably $R^{119}$ is H, OH, alkoxy or $C_{1-6}$ alkyl; more preferably $R_{19}$ is $C_{1-6}$ alkyl; and particularly $R^{119}$ is —$CH_3$;

$R^{120}$ is H, —OH, $C_{1-6}$ alkoxy or $C_{1-6}$ alkyl; preferably $R^{120}$ is H, —OH, or $C_{1-6}$ alkoxy; more preferably $R^{120}$ is —OH or $C_{1-6}$ alkoxy; most preferably $R^{120}$ is —OH;

$R^{127}$ is H, —OH, $C_{1-6}$ alkyl, $C_{1-6}$ alkoxy or $C_{1-6}$ hydroxyalkyl; preferably $R^{127}$ is H, $C_{1-6}$ alkyl or $C_{1-6}$ alkoxy; more preferably $R^{127}$ is H or $C_{1-6}$ alkyl; most preferably $R^{127}$ is methyl, ethyl or propyl;

$R^{128}$ and $R^{129}$ are the same or different and are H or —OH; preferably both $R^{128}$ and $R^{129}$ are H;

$R^{132}$ is H, —OH or =O; preferably $R^{132}$ is H or —OH; most preferably $R^{132}$ is H; and 8133 is H, or $R^{133}$— and $R^{115}$ taken together are =O, or $R^{133}$ and $R^{114}$ taken together represent the second bond of a double bond joining adjacent carbon atoms; preferably $R^{133}$ is H or $R^{133}$ and $R^{114}$ taken together represent the second bond of a double bond joining adjacent carbon atoms.

Preferred steroidal sapogenins of the formula XV are those in which: $R^{112}$ is H or —OH; $R^{113}$ is H or —OH; $R^{114}$ is H or —OH, or $R^{114}$ and $R^{133}$ taken together represent the second bond of a double bond joining adjacent carbon atoms; $R^{115}$ is H or —OH $R^{116}$ is H, —OH or =O; $R^{117}$ is H, —OH or =O; $R^{118}$ is H or —OH $R^{127}$ is $C_{1-6}$ alkyl; and $R^{128}$ and $R^{129}$ are the same or different and each represent H or —OH; $R^{132}$ is H, —OH or =O.

More preferably steroidal sapogenins of the formula XV are those in which: $R^{112}$ is H or —OH; $R^{113}$ is H or —OH; $R^{114}$ is H or —OH, or $R^{114}$ and $R^{133}$ taken together represent the second bond of a double bond joining adjacent carbon atoms; $R^{115}$ is H or —OH; $R^{116}$ is H or =O; $R^{117}$ is H, —OH; $R^{118}$ is H or —OH; $R^{127}$ is $C_{1-6}$ alkyl; $R^{128}$ and $R^{129}$ are the same or different and each represent H or —OH; and $R^{132}$ is H or —OH.

More preferably steroidal sapogenins of the formula XV are those in of the general formula IXa:

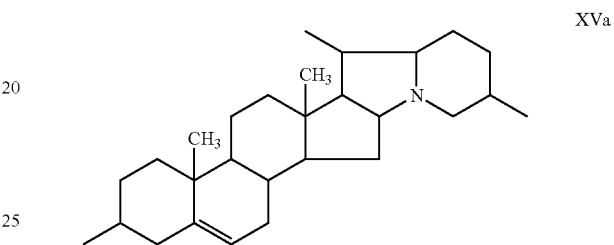

The most preferred compound of the formula VIII in which the steroid group is of the formula XV is:

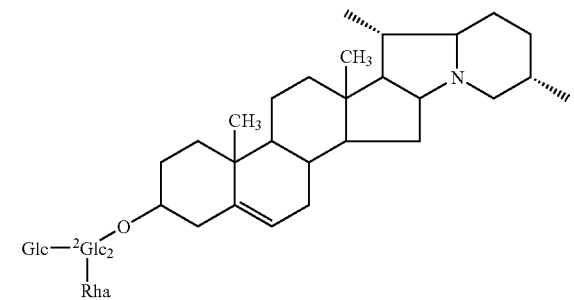

isolatable from *Lilium macklineae* (Sashida Y Chemical & Pharmaceutical Bulletin 39(9), 2362-8 (1991))

In a further embodiment the preferred group of steroidal sapogenins are those in which the steroidal sapogenin is of the formula XVI:

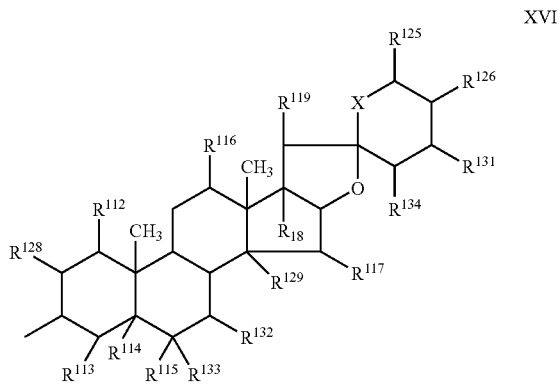

wherein:

$R^{112}$ is H, OH, $C_{1-6}$ alkyl or $C_{1-6}$ alkoxy; preferably $R^{112}$ is H or —OH; most preferably $R^{113}$ is H, —OH, =O, or $C_{1-6}$ alkyl; preferably $R^{113}$ is H or —OH; most preferably $R^{113}$ is H;

$R^{114}$ is H, —OH or $C_{1-6}$ alkyl or $R^{114}$ and $R^1_{33}$ taken together represent the second bond of a double bond joining adjacent carbon atoms; preferably $R^{114}$ is H or $R^{114}$ and $R^{133}$ taken together represent the second bond of a double bond joining adjacent carbon atoms;

$R^{115}$ is H, or —OH, or $R^{115}$ and $R^{133}$ taken together are =O; preferably $R^{115}$ is H, or $R^{115}$ and $R^{133}$ taken together are =O; more preferably $R^{115}$ is H;

$R^{116}$ is H, —OH or =O; preferably $R^{116}$ is H or =O; more preferably $R^{116}$ is H;

$R^{117}$ is H, —OH or =O; preferably $R^{117}$ is H or —OH; more preferably $R^{117}$ is H;

$R^{118}$ is H, —OH, $C_{1-6}$ alkoxy or $C_{1-6}$ alkyl; preferably $R^{118}$ is H, OH, $C_{1-6}$ alkoxy; more preferably $R^{118}$ is H or —OH; most preferably $R^{118}$ is H;

$R^{119}$ is H, —OH, $C_{1-6}$ alkyl or $C_{1-6}$ alkoxy; preferably $R^{119}$ is H, —OH, $C_{1-6}$ alkyl; more preferably $R^{119}$ is H, —OH or $C_{1-6}$ alkyl; most preferably $R^{119}$ is $C_{1-6}$ alkyl; and particularly $R^{119}$ is —CH$_3$;

$R^{125}$ is H, —OH, $C_{1-6}$ alkyl or $C_{1-6}$ alkoxy; preferably $R^{125}$ is H or —OH; more preferably $R^{125}$ is H;

$R^{126}$ is H, —OH, $C_{1-6}$ alkyl, $C_{1-6}$ hydroxyalkyl, $C_{1-6}$-alkoxy-$C_{1-6}$-alkyl, =CH$_2$ or =CH—$C_{1-6}$-alkyl; preferably $R^{126}$ is $C_{1-6}$ alkyl, $C_{1-6}$ hydroxyalkyl, $C_{1-6}$-alkoxy-$C_{1-6}$-alkyl, =CH$_2$ or =CHC$_{1-6}$ alkyl; more preferably $R^{126}$ is $C_{1-6}$ alkyl, $C_{1-6}$ hydroxyalkyl or =CH$_2$; most preferably $R^{126}$ is —C$_2$H$_4$OH, —CH$_2$OH, $C_{1-6}$ alkyl, or =CH$_2$, even more preferably $R^{126}$ is —C$_2$H$_4$OH, —CH$_2$OH, —C$_2$H$_5$, —CH$_3$ or =CH$_2$ and particularly $R^{126}$ is —CH$_3$ or =CH$_2$;

$R^{128}$ and $R^{129}$ are the same or different and are H or —OH; preferably both $R^{128}$ and $R^{129}$ are H;

$R^{131}$ is H or —OH; preferably $R^{131}$ is H;

$R^{132}$ is H, —OH or =O; preferably $R^{132}$ is H or —OH; most preferably $R^{132}$ is H;

$R^{133}$ is H, or $R^{133}$ and $R^{115}$ taken together are =O, or $R^{133}$ and $R^{114}$ taken together represent the second bond of a double bond joining adjacent carbon atoms; preferably $R^{133}$ is H or $R^{133}$ and $R^{114}$ taken together represent the second bond of a double bond joining adjacent carbon atoms;

$R^{134}$ is H or —OH; preferably $R^{134}$ is H; and

X is O, S or NH; preferably X is O or NH; more preferably X is O.

Preferred steroidal sapogenins of the formula XVI are those in which: $R^{112}$ is H or —OH; $R^{113}$ is H or —OH; $R^{114}$ is H or —OH, or $R^{114}$ and $R^{133}$ taken together represent the second bond of a double bond joining adjacent carbon atoms; $R^{115}$, $R^{118}$ $R^{128}$ and $R^{129}$ are the same or different and each represent H or —OH, $R^{116}$ is H, OH or =O; $R^{117}$ is H, —OH or =O; $R^{118}$ is H, —OH or $C_{1-6}$-alkoxy; $R^{119}$ is H, or $C_{1-6}$ alkyl; $R^{126}$ is H, $C_{1-6}$ alkyl, $C_{1-6}$ hydroxyalkyl, alkoxy-$C_{1-6}$-alkyl, =CH$_2$ or =CH—$C_{1-6}$-alkyl; $R^{129}$ is H or —OH; $R^{131}$ is H or —OH; $R^{132}$ is H, —OH or =O; and $R^{133}$ is H, or $R^{133}$ and $R^{115}$ taken together are =O, or $R^{133}$ and $R^{114}$ taken together represent the second bond of a double bond joining adjacent carbon atoms; and $R^{134}$ is H or —OH.

More preferred steroidal sapogenins of the formula XVI are those in which:

$R^{112}$, $R^{113}$, $R^{115}$ and $R^{128}$ each represent H; $R^{114}$ is H, or $R^{114}$ and $R^{133}$ taken together represent the second bond of a double bond joining adjacent carbon atoms; $R^{116}$ is H, or =O; $R^{117}$ is H or —OH; $R^{118}$ is H or —OH; $R^{119}$ is H, or $C_{1-6}$ alkyl; $R^{126}$ is $C_{1-6}$ alkyl, $C_{1-6}$ hydroxyalkyl or =CH$_2$; $R^{128}$ is H; $R^{129}$ is H or —OH; $R^{132}$ is H or —OH; and $R^{133}$ is H, or $R^{133}$ and $R^{114}$ taken together represent the second bond of a double bond joining adjacent carbon atoms.

Most preferred steroidal sapogenins of the formula XVI are those in which: $R^{112}$, $R^{113}$, $R^{115}$, $R^{116}$, $R^{117}$, $R^{125}$, $R^{128}$, $R^{131}$, $R^{132}$ and $R^{134}$, each represent H; $R^{114}$ is H, or $R^{114}$ and $R^{133}$ taken together represent the second bond of a double bond joining adjacent carbon atoms; $R^{118}$ is H or —OH; $R^{119}$ is $C_{1-6}$ alkyl; $R^{126}$ is $C_{1-6}$ alkyl or =CH$_2$; $R^{129}$ is H or —OH; $R^{132}$ is H; $R^{133}$ is H, or $R^{133}$ and $R^{114}$ taken together represent the second bond of a double bond joining adjacent carbon atoms.

The most preferred steroidal sapogenins of the formula XVI are those selected from the groups:

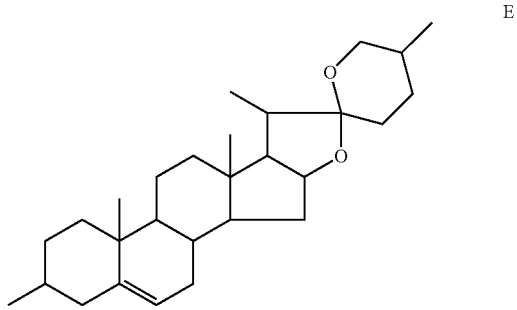

E

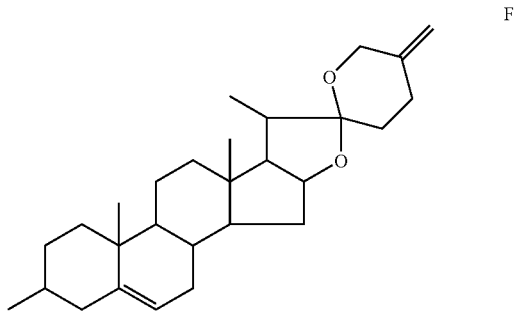

F

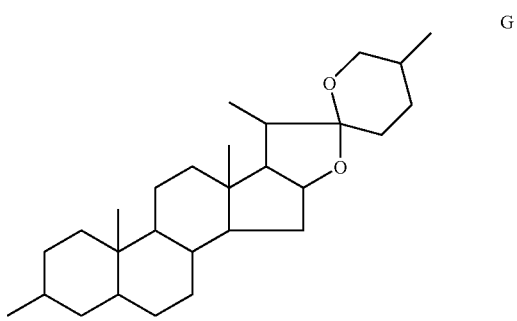

G

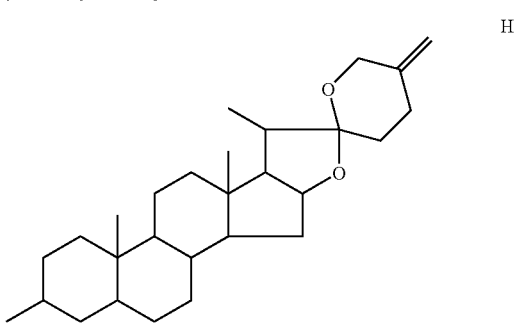

H

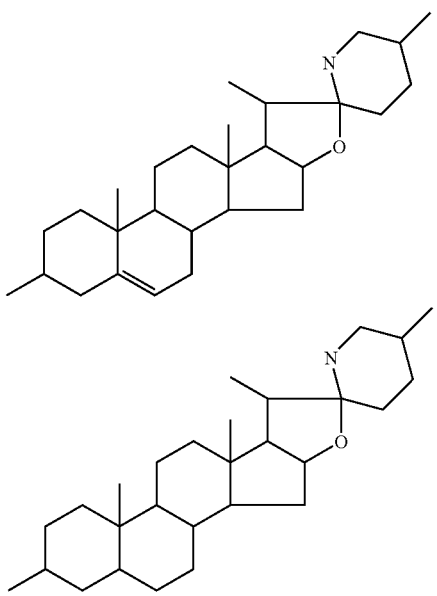

Particularly preferred steroidal sapogenins of the formula XVI are diosgenin, yamogenin, tigogenin, neotigogenin, sarsasapogenin, smilagenin, hecogenin, solasodine or tomatidine.

Particularly preferred compounds of the formula VIII are those combining preferred steroid groups with preferred saccharide groups.

Particularly preferred compounds of the formula I of the formulae I, IIIa and VIII are:

Protodioscin, pseudoprotodioscin, protoneodioscin, methylprotodioscin, methylprotoneodioscin, Trigoneoside IVa, glycoside F, Pardarinoside C, Pardarinoside D, dioscin, Balanitin VI, Deltonin, Shatavarin I and Shatavarin IV.

Further preferred compounds that are so far unnamed are Compounds 8a, 12a, 13a, 14a, 15a, 16a, 17a, 18a, 23a, 24a, 25a and 26a of table 1a.

The preferred compounds have the following chemical names:

Protodioscin is [(3β,22α,25R)-26-(β-D-glucopyranosyloxy)-22-hydroxyfurost-5-en-3-yl O-6-deoxy-α-L-mannopyranosyl (1→2)-046-deoxy-α-L-mannopyranosyl-(1→4)]-13-D-Glucopyranoside], pseudoprotodioscin is [(3β,22α,25R)-26-(β-D-glucopyranosyloxy)-furosta-5,20 (22)-dien-3-yl O-6-deoxy-α-L-mannopyranosyl (1→2)-046-deoxy-α-L-mannopyranosyl-(1→4)]-[3-D-Glucopyranoside], protoneodioscin is [(3(3β,22α,25S)-26-(β-D-glucopyranosyloxy)-22-hydroxyfurost-5-en-3-yl O-6-deoxy-α-L-mannopyranosyl (1→2)-O-[6-deoxy-α-L-mannopyranosyl-(1→4)]-13-β-Glucopyranoside], methylprotodioscin is [(3(3β,22α,25R)-26-(β-D-glucopyranosyloxy)-22-methoxyfurost-5-en-3-yl O-6-deoxy-α-L-mannopyranosyl (1→2)-O-[β-deoxy-α-L-mannopyranosyl-(1→4)]-β-D-Glucopyranoside], methylprotoneodioscin is [(3(3β,22α,25S)-26-(β-D-glucopyranosyloxy)-22-methoxyfurost-5-en-3-yl O-6-deoxy-α-L-mannopyranosyl (1→2)-O-[6-deoxy-α-L-mannopyranosyl-(1→4)]-β-D-Glucopyranoside], Trigoneoside IVa is (3β,25 S)-26-(β-D-glucopyranosyloxy)-22-hydroxyfurost-5-en-3-yl O-6-deoxy-α-L-mannopyranosyl-(1→2)-O-[β-D-glucopyranosyl-(1→4)]-β-D-glucopyranoside, glycoside F is (3β,25R)-26-(β-D-glucopyranosyloxy)-22-hydroxyfurost-5-en-3-yl O-6-deoxy-α-L-mannopyranosyl-(1→2)-O-[β-D-glucopyranosyl-(1→4)]-β-D-glucopyranoside, Pardarinoside C is (3β,5α,22α,25R)-26-(acetyloxy)-14,17-dihydroxy-22-methoxyfurostan-3-yl O-6-deoxy-α-L-annopyranosyl-(1→2)-O-[β-D-gluco-pyranosyl-(1→4)]-β-D-Glucopyranoside, Pardarinoside D is 13-D-glucopyranoside, (3β,5α,22α,25R)-26-(acetyloxy)-17-hydroxy-22-methoxyfurostan-3-yl O-6-deoxy-α-L-mannopyranosyl-(1→2)-O-[β-D-glucopyranosyl-(1→4)]-β-D-glucopyranoside, dioscin is [(3(3,25R)-spirost-5-en-3-yl O-6-deoxy-α-L-mannopyranosyl-(1→2)-046-deoxy-α-L-mannopyranosyl-(1→4)]-β-D-glucopyranoside], Balanitin VI is (3β,25 S)-spirost-5-en-3-yl-O-α-L-rhamnopyranosyl-(1→2)-O-[β-D-glucopyranosyl-β-D-glucopyranoside, Deltonin is (3β,25R)-spirost-5-en-3-yl-O-α-L-rhamnopyranosyl-(1→2)-O-[β-D-glucopyranosyl-β-D-glucopyranoside, Shatavarin I is (3β,5β,22α,25S)-26-(β-D-glucopyranosyloxy)-22-hydroxyfurostan-3-yl O-6-deoxy-α-L-mannopyranosyl-(1-42)-O-[β-D-glucopyranosyl-(1→4)]-β-D-glucopyranoside, Shatavarin IV is (3β,5β,25S)-spirostan-3-yl O-6-deoxy-α-L-mannopyranosyl-(1→2)-040-D-glucopyranosyl-β-D-glucopyranoside, Compound 8a is (3(3,25R)-26-(β-D-glucopyranosyloxy)-22-methoxyfurost-5-en-3-yl O-6-deoxy-α-L-mannopyranosyl-(1→2)-O-[β-D-glucopyranosyl-(1→4)]-β-D-Glucopyranoside, compound 12a is [(3β,12α,25R)-12-hydroxyspirostan-3-yl O-6-deoxy-α-L-mannopyranosyl-(1→2)-[β-D-glucopyranosyl-(1→4)]-β-D-glucopyranoside], compound 13a is [(25S)-spirost-5-ene-3β27-diol 3-O-{6-deoxy-α-L-mannopyranosyl-(1→2)-[β-D-glucopyranosyl-(1→4)]-β-D-glucopyranoside}], compound 14a is [(25R,26R)-26-methoxyspirost-5-en-3β-ol 3-O-{6-deoxy-α-L-mannopyranosyl-(1→2)-[β-D-glucopyranosyl-(1-4)]-β-D-glucopyranoside}], compound 15a is [3β,25R,27(S)]-27-(4-carboxy-3-hydroxy-3-methyl-1-oxobutoxy)spirost-5-en-3-yl O-6-deoxy-α-L-mannopyranosyl-(1→2)-O-[β-D-glucopyranosyl-(1-44)]-β-D-glucopyranoside], compound 16a is [313,25R,27(S)]-27-[(3-hydroxy-5-methoxy-3-methyl-1,5-dioxopentypoxy]spirost-5-en-3-yl O-6-deoxy-α-L-manriopyranosyl-(1→2)-O-[β-D-glucopyranosyl-(1→4)]-β-D-gluco-pyranoside], compound 17a is 13-D-Glucopyranoside, (3(3,25R,26R)-[7-hydroxy-26-methoxyspirost-5-en-3-yl O-6-deoxy-α-L-mannopyranosyl-(1→2)-O-[β-D-glucopyranosyl-(1→4)]-β-D-glucopyranoside, compound 18a is (3(3,25R,26R)-26-hydroxyspirost-5-en-3-yl O-6-deoxy-α-L-mannopyranosyl-(1→2)-041-D-glucopyranosyl-(1→4)]-β-D-glucopyranoside, compound 23a is 26-O-β-D-glucopyranosylnuatigenin 3-O-α-L-rhamnopyranosyl-(1→2)-O-[β-D-glucopyranosyl-(1→4)]-β-D-glucopyranoside Compound 24a is solanidine 3-O-α-L-rhamnopyranosyl-(1→2)-O-[β-D-glucopyranosyl-(1→4)]-β-D-glucopyranoside, compound 25a is (3(3,255)-26-(β-D-glucopyranosyloxy)-22-hydroxyfurost-5, 25 (27) dien-3-yl O-6-deoxy-α-L-mannopyranosyl-(1→2)-O-[β-D-glucopyranosyl-(1→4)]-β-D-glucopyranoside, and compound 26a is solasodine 3-O-α-L-rhamno-pyranosyl-(1→2)-O-[β-D-glucopyranosyl-(1→4)]-β-D-glucopyranoside Preferred compounds of the formula I of the formula IIIb are protogracillin proto neogracillin methylprotogracillin, methylprotoneogracillin, pseudoprotogracillin, dracenoside Q dioscoreside E , dracenoside P tuberoside C icogenin gracillin, collettiside IV 17-OH gracillin dracaenoside H dracaenoside L, dracaenoside I, lilioglycoside H, lilioglycoside I, dracaenoside D, neoalsoside A, neoalsoside C and hoduloside V, Lotoside II Further preferred compounds of the formula I of the formula Mb that are as yet unnamed are compounds 17b, 21b and 25b of table 2.

The preferred compounds of the formula I of the formula Mb have the following chemical names. Protogracillin is [(3β,22α,25R)-26-(β-D-glucopyranosyloxy)-22-hydroxyfurost-5-en-3-yl O-6-deoxy-α-L-mannopyranosyl (1→2)-O-[β-D-glucopyranosyl-(1→3)]-β-D-glucopyranoside], proto neogracillin is [(3β,22α,25S)-26-(β-D-glucopyranosyloxy)-22-hydroxyfurost-5-en-3-yl O-6-deoxy-α-L-mannopyranosyl (1→2)-O-[β-D-glucopyranosyl-(1→3)]-β-D-Glucopyranoside], methylprotogracillin is [(3β,22α,25R)-26-(β-D-gluco-pyranosyloxy)-22-methoxyfurost-5-en-3-yl O-6-deoxy-α-L-mannopyranosyl (1→2)-O-[β-D-glucopyranosyl-(1→3)]-β-D-Glucopyranoside], methylprotoneogracillin is [(3β,22α,25S)-26-(β-D-glucopyranosyloxy)-22-methoxyfurost-5-en-3-yl O-6-deoxy-α-L-mannopyranosyl (1→2)-O-[β-D-glucopyranosyl-(1→3)]-β-D-Glucopyranoside], pseudoprotogracillin is [(3β,25R)-26-(β-D-glucopyranosyloxy)furosta-5,20(22)-dien-3-yl O-6-deoxy-α-L-manno-pyranosyl-(1→2)-O-[β-D-glucopyranosyl-(1→3)]-β-D-Glucopyranoside], dracenoside Q is [(3β)-26-(β-D-glucopyranosyloxy)-14-hydroxyfurosta-5,20(22)-dien-3-yl O-6-deoxy-α-L-mannopyranosyl-(1→2)-O-[β-D-glucopyranosyl-(1→3)]-β-D-glucopyranoside], dioscoreside E is [26-O-β-D-glucopyranosyl-3β,26-dihydroxy-23(S)-methoxy]-25(R)-furosta-5,20(22)-dien-3-O-α-L-rhamnopyranosyl(1→2)-[β-D-glucopyranosyl(1→3)]-β-D-glucopyranoside], dracenoside P is [(3β)-26-(β-D-glucopyranosyloxy)-14,22-dihydroxyfurost-5-en-3-yl O-6-deoxy-α-L-mannopyranosyl-(1→2)-β-D-O-[β-D -glucopyranosyl-(1→3)]-glucopyranoside, tuberoside C is [(2β,3β,5α,25S)-26-(β-D-glucopyranosyloxy)-2-hydroxyfurost-20(22)-en-3-yl O-6-deoxy-α-L-mannopyranosyl -(1→2)-O-[β-D-gluco-pyranosyl-(1→3)]-β-D-glucopyranoside], icogenin is [(3β,22α,25R)-26-hydroxy-22-methoxyfurost-5-en-3-yl O-6-deoxy-α-L-mannopyranosyl-(1→2)-O-[β-D-glucopyranosyl-(1→3)]-β-D-glucopyranoside], gracillin is [(3β,25R)-spirost-5-en-3-yl O-6-deoxy-α-L-mannopyranosyl-(1→2)-O-[β-D-glucopyranosyl -(1→3)]-β-D-glucopyranoside, collettiside IV is [[(3 (3,25S)-spirost-5-en-3-yl O-6-deoxy-α-L-mannopyranosyl-(1→2)-O-[β-D-gluco-pyranosyl-(1→3)]-β-D-glucopyranoside], 17-OH gracillin is [(3β,25R)-17-hydroxyspirost-5-en-3-yl O-6-deoxy-α-L-mannopyranosyl-(1→2)-O-[β-D-glucopyranosyl-(1→3)]-(β-D-gluco-pyranoside], dracaenoside H is [(3β)-14-hydroxyspirost-5-en-3-yl O-6-deoxy-α-L-manno-pyranosyl-(1→2)-O-[β-D -glucopyranosyl-(1→3)]-[3-D-glucopyranoside, dracaenoside L is [(3β,24S ,25R)-14,24-dihydroxyspirost-5-en-3-yl O-6-deoxy-α-L-mannopyranosyl -(1→2)-O-[β-D-glucopyranosyl-(1→3)]-β-D-glucopyranoside], dracaenoside I is [(3 (3)-spirosta-5,25 (27)-dien-3-yl O-6-deoxy-α-L-mannopyranosyl -(1→2)-O-[β-D-glucopyranosyl -(1→3)]-β-D-glucopyranoside], lilioglycoside H is [(3(3,25S)-27-hydroxyspirost-5-en-3-yl O-6-deoxy-α-L-mannopyranosyl-(1→2)-O-[β-D-glucopyranosyl-(1→3)]-β-D-glucopyranoside], lilioglycoside I is [(3β,25R)-27-[(3S)-4-carboxy-3-hydroxy-3-methyl-1-oxobutoxy]spirost-5-en-3-yl O-6-deoxy-α-L-mannopyranosyl-(1→2)-O-[β-D-glucopyranosyl-(1→3)]-β-D-gluco-pyranoside], dracaenoside D is [3-[(O-6-deoxy-α-L-mannopyranosyl-(1→2)-O-[β-D-gluco-pyranosyl-(1→3)]-β-D-glucopyranosyl)oxy]-14-hydroxy-pregna-5, 16-dien-20-one, neoalsoside A is [(3β,12β,23S,24S)-20,24-epoxy-12,23,25-trihydroxydammaran-3-yl O-6-deoxy-α-L-mannopyranosyl-(1→2)-O-[β-D-glucopyranosyl-(1→3)]-β-D-glucopyranoside], neoalsoside C is [(3β,4α,12β,23S, 24S)-20,24-epoxy-12,23,25,28-tetrahydroxydammaran-3-yl O-6-deoxy-α-L-mannopyranosyl-(1→2)-O-[β-D-glucopyranosyl-(1→3)]-β-D-gluco-pyranoside], hoduloside V is [(3β,16β,23R)-16, 23:16,30-diepoxy-20-hydroxy-13-methyldammar-24-en-3-yl O-6-deoxy-α-L-mannopyranosyl-(1→2)-O-[β-D-glucopyranosyl-(1→3)]-β-D-glucopyranoside and Lotoside II is [(3β,15α,16β,22R)-16,22-epoxy-15, 16,20-trihydroxydammar-24-en-3-yl-O-6-deoxy-α-L-mannopyranosyl-(1→2)-O-[β-D-gluco-pyranosyl-(1→3)]-β-D-glucopyranoside].

compound 17b is [(3β,24R,25R)-17,24-dihydroxyspirost-5-en-3-yl O-6-deoxy-α-L-mannopyranosyl-(1→2)-O-[β-D-glucopyranosyl-(1→3)]-β-D-glucopyranoside], compound 21b is [(3β)-21-(β-D-glucopyranosyloxy)-20-hydroxydammar-24-en-3-yl O-6-deoxy-α-L-mannopyranosyl-(1→2)-O-[β-D-glucopyranosyl-(1→3)]-β-D-glucopyranoside] and compound 25b is [(313,1613,22R)-16, 22:16,30-diepoxy-20-hydroxydammar-24-en-3-yl O-6-deoxy-α-L-mannopyranosyl-(1→2)-O-[β-D-glucopyranosyl-(1→3)]-β-D-glucopyranoside]

Where any preferred substituent (such as $C_{1-6}$ alkyl, $C_{1-6}$ hydroxyalkyl) is said to be composed of from 1 to 6 carbon atoms (ie $C_{1-6}$) such substituents are more preferred with 1 to 4 carbon atoms (ie $C_{1-4}$), are more preferred still with 1 or 2 carbon atoms (ie methyl or ethyl) and are most preferred with only one carbon atom (ie are in the methyl form). Likewise where partial substituents such as the $C_{1-6}$ alkyl group or $C_{1-6}$ alkoxy group of $C_{1-6}$-alkoxy-$C_{1-6}$-alkyl are said to be composed of from 1 to 6 carbon atoms (ie $C_{1-6}$) such substituents are, independently one of the other, more preferred with 1 to 4 carbon atoms (ie $C_{1-4}$), are more preferred still with 1 or 2 carbon atoms (ie methyl or ethyl) and are most preferred with only one carbon atom (ie are in the methyl form).

Alkyl, alkenyl and alykynyl radicals may, where the number of carbons in the chain permits, be either straight-chain or branched chain. $C_{1-6}$ alkyl radicals may be, for example, methyl, ethyl, n-propyl or isopropyl, n-butyl, isobutyl or tert-butyl, isopentyl, 2,2-dimethyl propyl, n-hexyl, isohexyl and 1,3-dimethylbutyl. $C_{2-6}$ alkenyl radicals may be, for example, allyl, 1-methylprop-2-enyl, 2-methylprop-2-enyl, 2-methyl prop-1-enyl, but-2-enyl, but-3-enyl, 1-methyl-but-3-enyl, 1-methyl-but-2-enyl, 3-methylbut-2-enyl; where the alkenyl radical consists of 2-8 carbon atoms, the possible arrangements include, in addition to those possible for radicals with 2-6 carbon atoms, the following preferred radicals 5-methyl-hex-5-enyl, 4-methyl-hex-5-enyl, 3,4-dimethyl-hex-2-enyl. $C_{2-6}$. alkynyl may be, for example, propargyl, but-2-ynyl, but-3-ynyl, 1-methylbut-3-ynyl, A $C_{1-6}$ hydroxyalkyl group may, where chemically possible, be either a $C_{1-6}$ monohydroxyalkyl or a $C_{1-6}$ dihydroxyalkyl group.

Where moieties may be, in turn, substituted by a saccharide moiety it is preferred that the bond is through an oxygen to form a group such as:

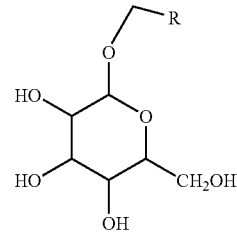

In the formula I the saccharide moiety A comprises multiple chiral centres. Thus each of the carbon atoms 1, 2, 3, 4 and 5 can, independently, be in the R or S form. Depending on the form of the anomeric carbon, A can, independently, be in either the alpha or beta anomeric form. For ring A the beta anomeric form is preferred. The saccharide moiety A can be in the D or L form; the D form is preferred. Depending on the arrangement around these chiral centres and the identity of the substituent $R_4$, the monosaccharide A can take a number of forms.

Thus, for example when $R^4$ is H, and $R^1$, $R^2$ and $R^3$ are —OH the saccharide moiety may, for example, be arranged as arabinopyranose, lyxopyranose, ribopyranose or xylopyranose; preferably it is xylopyranose or ribopyranose; more preferably it is xylopyranose.

When $R^4$ is —$CH_3$ and $R^1$, $R^2$ and $R^3$ are —OH the saccharide moiety is a 6-deoxy hexopyranose, and may be arranged as 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose preferably it is 6-deoxyallose or quinovose; preferably it is quinovose.

Where $R_4$ is —$CH_2OH$ and $R^1$, $R^2$ and $R^3$ are —OH the saccharide moiety is a hexopyranose and may be, for example, allose, altrose, galactose, glucose gulose, idose, mannose or talose; preferably it is allose, galactose or glucose, more preferably glucose. When $R_4$ is —$CH_2OH$, $R_2$ and $R_3$ are —OH, $R^1$ is $NR^5R^6$ and $R^5$ and $R^6$ are H the saccharide may be arranged as a pyranosamine, for example as glucosamine, mannosamine or galactosamine. When $R^4$ is —$CH_2OH$, $R^2$ and $R^3$ are —OH, $R^1$ is $NR^5R^6$ and $R^5$ is H and $R^6$ is —$COCH_3$ the saccharide may be arranged as an N-acetylpyranosamine for example N-acetylglucosamine (GlcNAc), N-acetylmannosamine or N-acetylgalactosamine (GalNAc); most preferably it is GalNAc.

In compounds of the formula IIb, when $R^4$ is H and $R^3$ is —OH, the saccharide moiety may, for example, be arranged as arabinopyranose, lyxopyranose, ribopyranose or xylopyranose; preferably the saccharide is xylopyranose or arabinopyranose; more preferably the saccharide is xylopyranose.

When $R^4$ is —$CH_3$ and $R^3$ is —OH the saccharide moiety A is a 6-deoxy hexopyranose, and may be arranged as 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose preferably it is fucose or quinovose; most preferably it is quinovose.

Where $R^4$ is —$CH_2OH$ and $R^3$ is —OH the saccharide moiety A is a hexopyranose and may be, for example, allose, altrose, galactose, glucose gulose, idose, mannose or talose; preferably it is galactose or glucose, and more preferably glucose.

Saccharides include, but are not limited to, monosaccharides, disaccharides, trisaccharides, tetrasaccharides and polysaccharides. Preferably saccharide moieties are monosaccharides, but may be independently selected as di- or oligosaccharides. Monosaccharides include, but are not limited to, tetroses pentoses, hexoses and heptoses; tetroses pentoses and hexoses are preferred.

Tetroses may be for example aldotetroses, such as erythrose and threose and aldoketoses erithrulose.

Pentoses include, but are not limited to aldopentoses, such as arabinose, lyxose, ribose and xylose and ketopentoses such as ribulose and xylulose and deoxypentoses such as 2-deoxyribose and 3-deoxyribose. Preferred pentoses are xylose and arabinose. Pentoses may be in the furanose (eg arabinofuranose, lyxofuranose, ribofuranose and xylofuranose) or the pyranose (eg arabinopyranose, lyxopyranose, ribopyranose and xylopyranose) forms.

Hexoses include, but are not limited to aldohexoses, such as, allose, altrose, galactose, talose, gulose, idose, mannose and glucose (preferred are glucose, mannose, galactose, altrose, allose idose and talose) and ketokexoses such as fructose, psicose, sorbose and tagatose.

Hexoses may also be deoxy hexoses wherein an —OH group is replaced by an —H group at any position other than the bonded group. 6-deoxyhexoses are for example 6-deoxyallose, 6-deoxyaltrose, 6-deoxygalactose (fucose), 6-deoxyglucose (quinovose), 6-deoxygulose, 6-deoxyidose, 6-deoxymannose (rhamnose) or 6-deoxytalose. Deoxyhexoses may also be 2-deoxy, 3-deoxy, 4-deoxy and 5-deoxy hexoses. The oxygen may be lacking at more than one position. Examples of deoxyhexoses are -2-deoxy-glucose, 2-deoxygalactose, 4-deoxyfucose, 3-deoxygalactose, 2-deoxyglucose, 3-deoxyglucose, 4-deoxyglucose. Deoxy-aldohexoses are preferred.

Hexoses also include hexosamines such as galactosamine, glucosamine and mannosamine, n-actyl hexosamines such as N-acetyl-galactosamine, N-acetyl-mannosamine and N-acetylglucosamine. Preferred hexoses are aldohexoses and deoxy hexoses, particularly preferred hexoses are glucose, galactose, quinovose, fucose and rhamnose.

Hexoses may be in the furanose or pyranose form; preferably in the pyranose form.

Other monosaccharides include uronic acids, for example fructuronic acid, galacturonic acid, iduronic acid, glucuronic acid, guluronic acid, mannuronic acid and tagaturonic acid; sedoheptulose, sialic acid, neuraminic acid, muramic acid, N-acetylneuraminic acid, N-acetylmuramic acid, O-acetylneuraminic acid, and N-glycolylneuraminic acid.

Of hexoses, aldohexoses and deoxyhexoses (particularly deoxyaldohexoses) are preferred; of pentoses, aldopentoses and deoxy-pentoses (particularly deoxyaldopentoses) are preferred.

Pharmaceutically acceptable esters of compounds of the formula I are for example, an ester with an aliphatic or aromatic carboxylic or sulphonic acid. Aliphatic carboxylic acids may be for example of up to 6 carbon atoms, for example a methyl, ethyl, tert-butyl succinyl or malyl. Aromatic carboxylic acids may for example benzoic acid, sulphonic acids may be methylsulphonic or p-toluenesulphonic acid, and include esters at any available esterifiable position.

Pharmaceutically acceptable esters further include known compounds in which the sugar —OH groups are esterified with an aliphatic carboxylic acid of up to 6 carbon atoms. Also included are known esters at the carbon 26-position with compounds such as hydroxymethylgluteryric acid or its methyl ester (for example compound 19(b) and structure VI xxiv).

Pharmaceutically acceptable ethers are, for example, with $C_{1-6}$ hydroxyallyl compounds which may be formed at any of the available —OH groups, for example on the saccharide moieties, or steroid moieties by converting one or more of the —OH groups to alkoxy groups (e.g. Li et al., *Carbohydr Res.* 20; 338(2): 117-21 (2003), Purdie and Irvine, *J. Chem. Soc.* 87, 1022 (1905), Haworth and Hirst, *J. Chem. Soc.* 119, 193 (1921) incorporated herein by reference).

A suitable pharmaceutically-acceptable salt form of the compounds of the formula I is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt.

Compounds of the formula I can be extracted from a variety of plant species. Examples of sources of compounds of the invention and example purification protocols are given in the references of tables 1 and 2 (which are incorporated herein by reference). Further sources of compounds of the invention and methods of isolation of such compounds are detailed in Hostettman K. and Marston A. Saponins. Cambridge University Press UK. (1995), particularly tables 2.2, 2.9, 2.10 and 2.11 and appendix 3—and references therein, which are incorporated herein by reference. Reference is made in this respect, and by way of example only, to Yoshikawa et al Heterocycles 47, 397-405 (1998), Sasheda et al., Chemical & Pharmaceutical Bulletin 39(9), 2362-8 (1991), Akhov et al., Journal of Agricultural and Food Chemistry 47(8), 3193-3196 (1999) Joshi and Dev, Indian J. Chem. 27B, 12-16 (1988), Ravikumar et al Indian J. Chem. 26B, 1012-1017 (1987), Vasil'eva and Paseshnichenko Appl. Biochem. Microbiol. 31, 206-209 (1995), Shimomura et al Phytochemistry 28, 3163-3170 (1989), Sharma and Sharma Phytochemistry. 33(3):683-6. (1993), Petit et al Journal of natural products 54, 1491-1502, Mimaki and Sashida Chemical & Pharmaceutical Bulletin 38(11), 3055-9 (1990). These documents are all incorporated herein by reference.

Many compounds of the invention are hydroxylated steroids. It is known in the art that such compounds, when exposed to solvent such as alcohols during purification or preparation, may be converted to alkoxy derivatives or to other derivatives such as methylketals (which revert to the original compounds upon drying). Particularly furostanol compounds of the formula VIa, in which the carbon at the at the 22-position of the furostanol structure, is substituted by —OH, may be converted to alkoxy derivatives when exposed to alcohols. Notably such compounds may become methoxy derivatives when purified from plant sources using methanol-containing solvents. Alternatively they may be converted to the corresponding alkoxy by reflux in an appropriate anhydrous alcohol at elevated temperature, for example methanol (Hu. et al Planta Medica, 63(2), 161-165 (1997)). Such alkoxylated compounds are also compounds of the invention.

Where the compounds of the invention are purified from natural sources it is preferred that they are used in isolated form. By isolated is meant that the compound is at least 1% pure, conveniently it is at least 10% pure, more conveniently at least 30% pure, preferably it is at least 50% pure more preferably it is at least 80% pure still more preferably it is at least 90% pure and most preferably it is at least 95% pure.

The purity of the compound is conveniently expressed as a ratio of UV absorption associated with the compound to UV absorption associated with other material in the sample, conveniently at 205 nm. The purity of the compound may be measured for example using a chromatography system such as for example TLC or HPLC such as are described in the references herein, particularly in those references relating to the compound in question, or in applicants co pending application WO05/060977

Alternatively, they can be synthesised by conventional organic chemistry methods and techniques. Reference in this respect is made to carbohydrate and steroid chemistry textbooks such as "Essentials of Carbohydrate Chemistry and Biochemistry" by Thisbe K. Lindhorst (2000) Wiley, "Carbohydrates in Chemistry and Biology" edited by Beat Ernst, Gerald W. Hart and Pierre Sinay (2000) Wiley, "Essentials of Carbohydrate Chemistry" by John F. Robyt (1998) Springer Verlag, "Carbohydrate Chemistry" by Hassan S. El Khadem (1988), "Carbohydrate Building Blocks" by Mikael Bols (1996), "Glycochemistry: Principles, Synthesis, and Applications" edited by P. G. Wang and C. R. Bertozzi (2001) Marcel Dekker, N.Y. and "Carbohydrate Chemistry" by the Royal Society of Chemistry Staff (1989) CRC Press.

The, compounds of the invention can be synthesised via a number of routes known to the skilled worker. For example by glycosylation of appropriate aglycones. The compounds of the present invention can be prepared from commercially available aglycones or by isolation of the aglycone or other precursor either from fenugreek seeds or from another plant source and subsequent chemical modification of the precursor.

A number of suitable aglycones are available commercially, alternatively an suitable aglycone may be prepared, either by isolation from a natural source, by deglycosylation of a suitable glycosylated compound (for example those compounds disclosed in Hostettman K. and Marston A. Saponins. Cambridge University Press UK. (1995) or herein), or by chemical synthesis from a variety of starting material that are readily available.

Methods of synthesising Galβ1-3(6-deoxy)GalNAcα-conjugates are given in Paulsen et al., Leibigs Ann. Chem. 747-758. (1992). These methods may be adapted by the skilled worker in combination with other methods referenced herein to synthesize other compounds of the formula I.

The skilled worker will be aware of many sources of spirostanol and furostanol aglycones suitable for preparing compounds for use in the invention. For example spirostanol aglycones wherein X=O or X=NH may be, for example, sarsapogenin, smilagenin, 12β-hydroxysmilagenin, Rhodeasapogenin, Isorhodiasapogenin, Samogenin, 12β-hydroxysamogenin, Markogenin, Yonogenin, Convallagenin A, Convallagenin B, Tokorogenin, Tigogenin, Neotigogenin, Gitogenin, Agigenin Digitogenin, Chlorogenin, Paniculogenin, (25R)-Spirostan-3β, 17α21-triol, Allogenin, (25R)-5α-Spirostan-2α,3β,5α,6α-tetraol, (24S,25R)-5α-Spirostan-2α, 3β,5α,6β,24-pentaol, Yamogenin Diosgenin, Yuccagenin, Lilagenin, Ruscogenin, (25S)-Ruscogenin, Neopraserigenin, Pennogenin, Isonuatigenin, Cepagenin, 24a-hydroxypennogenin, Ophiogenin, Sibiricogenin, Convallamarogenin, Neoruscogenin, Hecogenin, Neohecogenin, Manogenin, Sisalagenin, Solasodine, Soladulcidine, Tomatidine and 5-dehydrotomatidine.

Deglycosylation of, for example steroidal glycosides, may be simply carried out by acid hydrolysis, for example in a 50:50 mix of 2N HCl: dioxane at 100° C. in a sealed tube for 4.5 hrs (Hu K (1997) *ibid*).

Methods for the synthesis of a number of steroidal aglycones have been known for many years. For example synthesis of diosgenin, yamogenin, kryptogenin and isonarthogenin have been reported by Kessar et al., *Tetrahedron;* 24(2):905-7 (1968), Kessar et al., Tetrahedron 24(2):899-904 (1968) and Kessar et al., *Tetrahedron*. 24(2):887-92 (1968). General synthetic routes to a variety of tri saccharide substituted spirostanol saponins are known (Deng et al., Carbohydr Res. 30; 317(1-4):53-62. (1999), Li et al., Carbohydr Res.; 9; 331(1):1-7. (2001), Yu et al., Tetrahedron letters, 42, 77-79 (2001) Yu et al., J Org Chem.; 13; 67(25):9099-102 (2002)). Methods of synthesis of spirostanol saponins having 2,4 (Cheng et al., J Org Chem. 2; 68(9):3658-62 (2003), Deng et al 1999 ibid, Du et al., Org Lett.; 2; 5(20):3627-30. (2003), Lehmann. et al., *Carbohydr Res*. 337(21-23): 2153-9 (2002)). and 2,3 (Li C et al. *Carbohydr Res.;* 306(1-2):189-95. (1998), Zou C. C. et al *Carbohydr Res*. 4; 338(8): 721-7 (2003), Gu G et al *J Org Chem.* 69(16):5497-500 (2004)) branched oligosaccharide moieties are also known. Methods of synthesis of furostanol saponins, synthesis of derivatised saponins and interconversion of spirostanol and furostanol saponins have also been devised (Yu et al., J Comb Chem.; 3(5):404-6. (2001), Yu et al., J Org Chem.; 13; 67(25):9099-102 (2002), Cheng et al., J Org Chem.; 2; 68(9):3658-62 (2003), Du et al., Org Lett.; 2; 5(20):3627-30. (2003), Li et al., *Carbohydr Res.* 20; 338(2): 117-21 (2003), Lehmann et al., *Carbohydr Res.* 337(21-23): 2153-9 (2002), Tobari et al., *Eur J Med Chem.* 35(5): 511-27 (2000), Wang et al., *Steroids*. 69(10): 599-604 (2004)).

Furthermore, furostanol and spirostanol saponins can be inter converted using a β-glucosidase(Inoue et al., *Phytochemistry* 41(3), 725-7 (1996)) and pseudosaponins maybe cyclised to form the spirostanol derivative (Tobari et al., *Eur J Med Chem*. 35(5): 511-27 (2000)).

Combinatorial approaches to saponin synthesis have also been reported (Lautrette S. et al., *Chem Commun (Camb)*. 7; (5): 586-7 (2004), Yu et al., J Comb Chem.; 3(5):404-6. (2001)). These references also provide information and further references on derivatisation of saccharide hydroxyl and hydroxyalkyl groups and are incorporated herein by reference.

As used herein the term aglycone refers to steroidal glycosides wherein the saccharide moieties are not present. The compounds may have other substituents at the position originally occupied by the saccharide moiety. Particularly aglycones that are furostanol saponins when not glycosylated may be in the ring closed state as the equivalent spirostanol compounds. Steroidal glycosides are compounds having a steroid or substituted steroid core, to which is attached one or more saccharide moieties. A steroidal sapogenin is the aglycone of a steroidal saponin. A steroidal saponin is a naturally occurring or derived steroidal glycoside.

As used herein the term core 2 GlcNAc-T inhibitor means and inhibitor of the enzyme core 2-GlcNAc-T and preferably the ability of preparations comprising a core 2 GlcNAc-T enzyme activity described herein to incorporate UDP-6 [$^1$H]-N-acetylglucosamine into products as measured in the assays described herein.

An anti cell adhesion agent is an agent that reduces the adhesion of cells to a substrate such as platelets or the lining of blood vessels or other tissues, an anti cell-cell interaction agent is an agent that reduces the interaction between cells. An anti cellular extravasation agent is an agent that reduces the passage of cells from the blood stream through the walls of blood vessels.

The term "treating", as used herein, includes treating as prophylaxis or treatment of a current or remitting illness. For the avoidance of doubt the term $C_{1-6}$ acyl is —CO—$C_{1-5}$-alkyl.

In a second aspect of the invention is provided the use of compounds of the formula I in the manufacture of a medicament for the treatment of a condition associated with detrimental activity, particularly raised activity, of the enzyme core 2 GlcNAc-T .

In a third aspect of the invention is provided the use of a compound of formula I as an anti cell adhesion agent, an anti cell-cell interaction agent or an anti cellular extravasation agent.

In a fourth aspect of the invention is provided a pharmaceutical composition comprising compound of the formula I. These compositions preferably further comprise pharmaceutically acceptable carriers, diluents or excipients.

In a fifth aspect of the invention is provided a method of treatment of multiple sclerosis in a subject comprising administering to a subject in need thereof, a therapeutically effective amount of a compound capable of reducing the activity of Core 2 GlcNAc-T. Preferably the compound will be used to reduce the activity of Core 2 GlcNAc-T to normal or approximately normal levels.

The activity of Core 2 GlcNAc-T can be reduced in a number of ways, for example by inhibiting the transcription of the Core 2 GlcNAc-T gene, by inhibiting the translation of the Core 2 GlcNAc-T mRNA, by inhibiting the post translational modification of the protein (e.g. by inhibiting the phosphorylation of the protein through protein kinase and thereby inhibiting its activation) or by inhibiting the enzyme activity.

Inhibitors of both Core 2 GlcNAc-T enzyme activity and of the activation of Core 2 GlcNAc-T by protein kinase C are known. Conveniently the level of Core 2 GlcNAc-T enzyme activity is reduced either by inhibiting the enzyme or inhibiting the phosphorylation of the protein.

Examples of Core 2 GlcNAc-T inhibitors suitable for use in the invention are: βGal(1→3)α(6-deoxy)GalNAcα-Bn. (Hindsgaul et al (1991) *J Biol Chem*. 266(27):17858-62, Kuhns et al (1993) *Glycoconjugate Journal* 10, 381-394; the following compounds activated as described by Told et al (1994) *Biochem Biophys Res Commun*. 198(2):417-23.: Galβ1→3GalNAcα-pnp, Galβ1→3GalNAcα-onp Gal-NAcα-pnp GalNAcβ-pnp, GlcNAcβ-pnp, Galβ-pnp, GlcNAcβ1÷3GalNAcα-pnp, L-Fucα1→2Galβ-pnp, GlcNAcα-pnp, Galβ1→3 GlcNAcβ-pn, Galβ1→6GlcNAcP-pnp; steroidal glycosides described in applicants co pending WO05060977 (incorporated herein by reference) and herein; and analogues of uridine diphosphate and uridine diphosphate-N-acetylglucosamine and peptides of the formula X-$X^1$-$X^2$-$X^3$-$X^4$ as described in WO0185748.

Antibodies to Core 2 GlcNAc-T may also be used to reduce the activity of the enzyme and suitable examples are described in Li et al (1999) Glycoconjugate Journal 16, 555-562 (1999), U.S. Pat. No. 5,684,134, WO09043662).

Inhibitors of Protein Kinase-Cβ2 (PKCβ2) are known to inhibit Core 2 GlcNAc-T activation in diabetic complications, where Core 2 activity is known to be raised, (Chibber et al (2003) *Diabetes*. 52(6):1519-27—incorporated herein by reference) and are known to inhibit leukocyte binding to epithelial cells in vitro. Examples of 3,4-di-indoyl-pyrrol-2, 5-dione derivatives that inhibit PKCβ are found in, for example WO9535294 and WO9517182. A particular example of a PKCβ2 inhibitor is Ruboxistaurin (LY333531 & LY379196)

In a sixth aspect of the invention is provided the use of compound capable of reducing Core 2 GlcNAc-T activity in the manufacture of a medicament for the treatment of multiple sclerosis. For example such compounds are either inhibitors of Core 2 GlcNAc-T or inhibitors of PKCβ (especially of PKCβ2); preferably compounds are inhibitors of Core 2 GlcNAc-T.

In a seventh aspect of the invention is provided a pharmaceutical composition for the treatment of multiple sclerosis comprising a compound capable of lowering the activity of Core 2 GlcNAc-T and preferably also comprising a pharmaceutically acceptable carrier.

In an eighth aspect of the invention is provided a method of diagnosing multiple sclerosis in a subject comprising comparing the level of Core 2 GlcNAc-T activity associated with leukocytes of a subject with the level of Core 2 GlcNAc-T activity determined in healthy non afflicted individuals. A level of Core 2 GlcNAc-T higher than that of healthy non afflicted individuals being indicative that the subject is afflicted with MS.

The measurement of Core 2 GlcNAc-T activity is preferably carried out on isolated tissue samples, such as biopsy samples or blood samples. Conveniently the measurement will be carried out by assay of Core 2 GlcNAc-T from isolated blood cells and particularly on preparations containing leukocytes, preferably substantially free of red blood cells. One such suitable procedure using leukocytes isolated from blood samples is described in Chibber et al *Diabetes* 49, 1724-1730 (2000). Typically values of Core 2 GlcNAc-T activity associated with leukocytes of a subject will be compared to an established normal level for healthy non afflicted individuals.

The inventors have determined that the level of Core 2 GlcNAc-T activity in leukocyte preparations obtained from healthy individuals and assayed by the method of Chibber et al (2000) id or as detailed in Example 4 is between 40 and 1000 pmoles/hr/mg (oligosaccharide incorporated per mg protein) and typically between 50 and 500 pmoles/hr/mg of protein. values obtained for three groups of healthy control individuals were 249±35.9 (n=25), 334±86 (n=11) and 283±37 (n=31) pmols/hr/mg.

Levels of Core 2 GlcNAc-T in individuals afflicted with MS have been noted to be in the region of at least 2 times, for example at least 4 times, at least 6 times and most typically at least 8 times the level of healthy non afflicted individuals when leukocytes from blood samples assayed according to the above methods.

In a ninth aspect of the invention is provided a method of determining the utility of a test substance as useful in the treatment of MS comprising determining the ability of the substance to inhibit the activity of Core 2 GlcNAc-T, particularly that activity associated with leukocytes.

Conveniently inhibition of Core 2 GlcNAc-T activity can be determined by comparing the level of Core 2 GlcNAc-T activity obtained in an assay in which a test substance is incorporated to the level of Core 2 GlcNAc-T activity in the assay with no test substance.

Conveniently inhibition of Core 2 GlcNAc-T enzyme activity can be determined by a method comprising (a) contacting source of active Core 2 GlcNAc-T enzyme with an acceptor and a sugar donor for a Core 2 GlcNAc-T in the presence and absence of the test substance; (b) measuring the amount of sugar donor transferred to the acceptor, and relating decreased transfer in presence of test substance as compared to that in its absence to Core 2 GlcNAc-T inhibitory activity. It is particularly preferred and convenient to measure such activity on Core 2 GlcNAc-T present in or derived from leukocytes, particularly of an MS patient.

Any source of Core 2 GlcNAc-T activity may be used, for example an enzyme produced by recombinant means such as those disclosed in WO04111196, U.S. Pat. No. 5,658,778 or a tissue or cell culture or a preparation exhibiting measurable Core 2 GlcNAc-T activity derivable there from, for example U937 cells or heart lysates as described in applicants co pending WO05060977 and herein.

Examples of sugar donors and acceptors and the general conditions for assaying Core 2 GlcNAc-T activity are well known in the art e.g. Chibber et al (2000) id Hindsgaul et al (1991) id, Kuhns et al (1993) id Told et al (1994) id and Orlacchio et al (1997) id. Such methods can be adapted for use in the fourth aspect of the invention by incorporation of test substances as described above. Further examples of assays according to the invention are given in WO 0031109 in applicants co pending WO05060977 and herein. Conveniently the sugar donor is UDP-GlcNAc and the sugar acceptor is βGal(1-3)DαGalNAc-p-nitrophenol.

The term treating MS, as used herein, includes treating as prophylaxis and the treatment of existing disease. MS includes for example relapsing/remitting, secondary progressive, progressive relapsing and primary progressive forms of the condition. Other forms include benign, malignant, chronic/progressive and transitional/progressive MS.

Medicaments of the invention comprising compounds of the formula I will typically be prepared in a sterile and pyrogen free form. They can be administered by oral or parenteral routes, including intravenous, intramuscular, intraperitoneal, subcutaneous, transdermal, airway (aerosol), rectal, vaginal and topical (including buccal and sublingual) administration.

The medicament may be made up in liquid form in which case it will typically, in addition to the compound of the formula I, comprise a pharmaceutically acceptable diluent or it may be made up in solid form. For oral administration, the compounds of the invention will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavouring agents, colouring agents and preservatives. Examples of suitable inert diluents include sodium and calcium carbonate, sodium and calcium phosphate, and lactose, while corn starch and alginic acid are examples of suitable disintegrating agents. Binding agents include, for example starch and gelatine, while the lubricating agent, if present, may for example, be magnesium stearate, stearic acid or talc. If desired, the tablets may be coated with an enteric coating material, such as glyceryl mono stearate or glyceryl distearate, to delay absorption in the gastrointestinal tract. Capsules for oral use include hard gelatine capsules in which the active ingredient is mixed with a solid diluent, and soft gelatine capsules wherein the active ingredients is mixed with water or an oil such as peanut oil, liquid paraffin or olive oil Formulations for rectal administration may for example be presented as a suppository with a suitable base comprising, for example, cocoa butter or a salicylate.

Formulations suitable for vaginal administration may for example be presented as pessaries, tampons, creams, gels, pastes, foams or spray formulations containing in addition to the active ingredient such carriers as are known in the art to be appropriate.

In preparations for intramuscular, intraperitoneal, subcutaneous and intravenous use, the compounds of the invention will typically be provided in a pharmaceutically acceptable diluent to provide sterile solutions, emulsions, liposome formulations or suspensions. Typically the preparation will be buffered to an appropriate pH and isotonicity. For example suitable diluents include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives include ethyl and n-propyl p-hydroxybenzoate, and can be used for these aqueous suspensions.

The core 2 GlcNAc-T inhibitors of the present invention may also be presented as liposome formulations.

The isolated Core 2 GlcNAc-T inhibitors of the invention may also be incorporated into a food or beverage product.

In general a suitable dose of Core 2 GlcNAc-T inhibitor will be in the range of 10 ng to 50 mg per kilogram body weight of the recipient per day, preferably in the range 100 ng to 10 mg, more preferably in the range of 1 μg to 5.0 mg/kg/d. In some embodiments preferably in the range of 0.2 to 1.0 mg per kilogram body weight per day. The desired dose is preferably presented once daily or several times a day in sub doses. In some embodiments they may be dosed as two, three, four, five, six or more sub-doses administered at appropriate intervals throughout the day. These sub-doses may be administered in unit dosage forms, for example, containing 1 μg to 1500 mg, preferably 40 μg to 1000 mg, and most preferably 50 □g to 700 mg of active ingredient per unit dosage form, but in some embodiments may contain 10 to 1500 mg, preferably 20 to 1000 mg, and most preferably 50 to 700 mg of active ingredient per unit dosage form.

In the shorthand annotation used in structures herein Glc is glucose and Rha is rhamnose. The annotation 2,3 and 2,4 denote the position of attachment of the saccharides to the central monosaccharide.

The shorthand notation

used in structures herein denotes the structure:

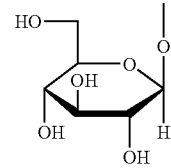

Table 1 Example Compounds of the Invention of the Formula I, IIIa and VIII

TABLE 1a

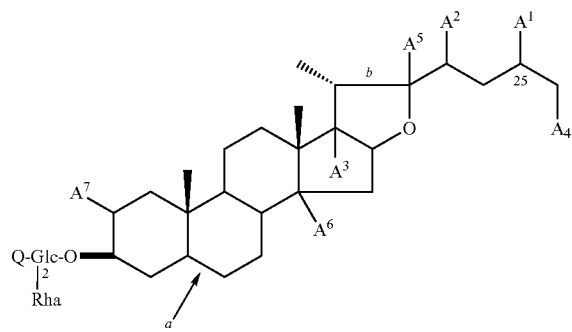

| Compound | Q | $A^1$ | $A^2$ | $A^3$ | $A^4$ | $A^5$ | $A^6$ | $A^7$ | 25 R/S | Bond a | Bond b |
|---|---|---|---|---|---|---|---|---|---|---|---|
| 1a | 4-Rha | Me | H | H | Glc | OH | H | H | R | Double | Single |
| 2a | 4-Rha | Me | H | H | Glc | Absent | H | H | R | Double | Double |
| 3a | 4-Rha | Me | H | H | Glc | OH | H | H | S | Double | Single |
| 4a | 4-Rha | Me | H | H | Glc | OMe | H | H | R | Double | Single |
| 5a | 4-Rha | Me | H | H | Glc | OMe | H | H | S | Double | Single |
| 6a | 4-Glc | Me | H | H | Glc | OH | H | H | S | Double | Single |
| 7a | 4-Glc | Me | H | H | Glc | OH | H | H | R | Double | Single |
| 8a | 4-Glc | Me | H | H | Glc | OMe | H | H | R | Double | Single |
| 9a | 4-Glc | Me | H | OH | —O•CO•CH$_3$ | OMe | OH | H | R | Single | Single |
| 10a | 4-Glc | Me | H | OH | —O•CO•CH$_3$ | OMe | H | H | R | Single | Single |
| 21a | 4-Glc | Me | H | H | Glc | OH | H | H | S | Single | Single |
| 25a | 4-Glc | =CH$_2$ | H | H | Glc | OH | H | H | — | Double | Single |

TABLE 1b

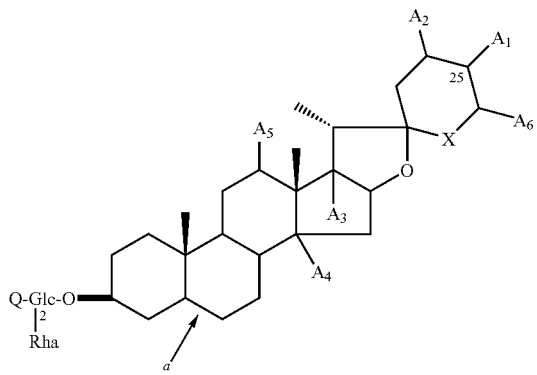

| Comp. | Q | A₁ | A₂ | A₃ | A₄ | A₅ | A₆ | 25R/S | Bond a |
|---|---|---|---|---|---|---|---|---|---|
| 11a | 4-Rha | Me | H | H | H | H | H | R | Double |
| 12a | 4-Glc | Me | H | H | H | OH | H | R | Single |
| 13a | 4-Glc | —CH₂OH | H | H | H | H | H | S | Double |
| 14a | 4-Glc | Me | H | H | H | H | OMe | R | Double |
| 15a | 4-Glc | * | H | H | H | H | H | R | Double |
| 16a | 4-Glc | ** | H | H | H | H | H | R | Double |
| 17a | 4-Glc | Me | H | OH | H | H | OMe | R | Double |
| 18a | 4-Glc | Me | H | H | H | H | OH | R | Double |
| 19a | 4-Glc | Me | H | H | H | H | H | S | Double |
| 20a | 4-Glc | Me | H | H | H | H | H | R | Double |
| 22a | 4-Glc | Me | H | H | H | H | H | S | Single |

Substituent "*" = 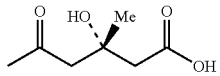

Substituent "**" = 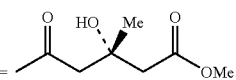

TABLE 1c

Further example compounds of the invention of the formula I, IIIa and VIII.

| Compound | Structure |
|---|---|
| 23a | 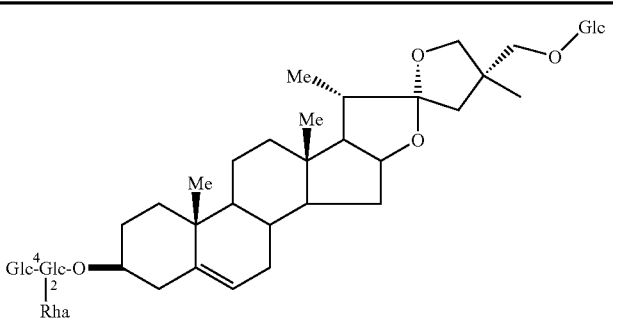 |
| 24a | 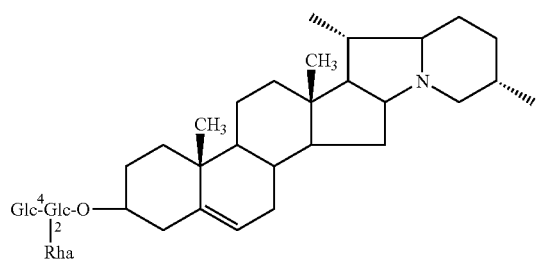 |

TABLE 1c-continued

Further example compounds of the invention of the formula I, IIIa and VIII.

| Compound | Structure |
|---|---|
| 26a | Glc-Glc(4,2)-O-[steroidal alkaloid], Rha at 2 |

TABLE 2

Key to example compounds of the invention of the formula I, IIIa and VIII and references

| Compound | Example references | Compound name |
|---|---|---|
| 1a | 1 | Protodioscin |
| 2a | 2 | Pseudoprotodioscin |
| 3a | 1 | Protoneodioscin |
| 4a | 1 | Methylprotodioscin |
| 5a | 1 | Methylprotoneodioscin |
| 6a | 3 | Trigoneoside IVa |
| 7a | 4, 3 | Glycoside F, protodeltonin, deltoside, |
| 8a | 5 | No name |
| 9a | 6 | Pardarinoside C |
| 10a | 6 | Pardarinoside D |
| 11a | 7 | Dioscin |
| 12a | 8 | Not named |
| 13a | 11, 9, 10, 5 | Not named |
| 14a | 9, 5 | Not named |
| 15a | 9, 10, 11, 12 | Not named |
| 16a | 10, 11 | Not named |
| 17a | 5 | Not named |
| 18a | 13 | Not named |
| 19a | 15, 5, 14 | Balanitin VI |
| 20a | 16, 17 | Deltonin |
| 21a | 19, 18 | Shatavarin I |
| 22a | 18, 23 | Shatavarin IV |
| 23a | 11 | Not named |
| 24a | 12 | Not named |
| 25a | WO05/060977 | Not named |
| 26a | 11 | Not named |

Table 3. Example Compounds of the Invention of the Formula IIIb

TABLE 3a

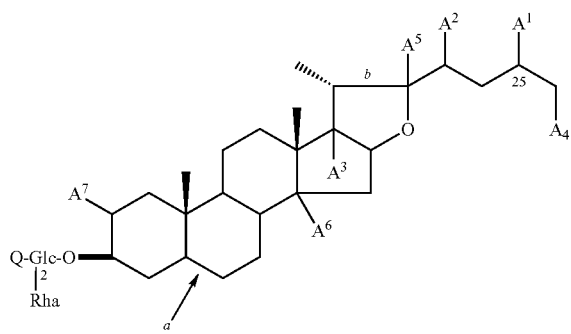

| Comp. | Q | $A^1$ | $A^2$ | $A^3$ | $A^4$ | $A^5$ | $A^6$ | $A^7$ | 25R/S | Bond a | Bond b |
|---|---|---|---|---|---|---|---|---|---|---|---|
| 1b | 3-Glc | Me | H | H | Glc | OH | H | H | R | Double | Single |
| 2b | 3-Glc | Me | H | H | Glc | OH | H | H | S | Double | Single |
| 3b | 3-Glc | Me | H | H | Glc | OMe | H | H | R | Double | Single |
| 4b | 3-Glc | Me | H | H | Glc | OMe | H | H | S | Double | Single |
| 5b | 3-Glc | Me | H | H | Glc | Absent | H | H | R | Double | Double |
| 6b | 3-Glc | Me | H | H | Glc | Absent | OH | H | R/S | Double | Double |
| 7b | 3-Glc | Me | OMe | H | Glc | Absent | OH | H | R | Double | Double |
| 8b | 3-Glc | Me | H | H | Glc | OH | OH | H | R/S | Double | Single |
| 9b | 3-Glc | Me | H | H | Glc | H | H | OH | S | Single | Double |
| 10b | 3-Glc | Me | H | H | OH | OMe | H | H | R | Double | Single |

TABLE 3b

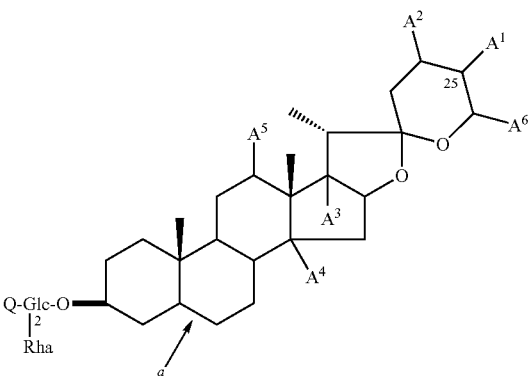

| Comp. | A | R₁ | R₂ | R₃ | R₄ | R₅ | R₆ | 25R/S | Bond a |
|---|---|---|---|---|---|---|---|---|---|
| 11b | 3-Glc | Me | H | H | H | H | H | R | Double |
| 12b | 3-Glc | Me | H | H | H | H | H | S | Double |
| 13b | 3-Glc | Me | H | OH | H | H | H | R | Double |
| 14b | 3-Glc | Me | H | H | OH | H | H | R/S | Double |
| 15b | 3-Glc | Me | OH | H | OH | H | H | S | Double |
| 16b | 3-Glc | =CH₂ | H | H | H | H | H | — | Double |
| 17b | 3-Glc | Me | OH | OH | H | H | H | R | Double |
| 18b | 3-Glc | —CH₂OH | H | H | H | H | H | R | Double |
| 19b | 3-Glc | * | H | H | H | H | H | R | Double |

Substituent "*" = 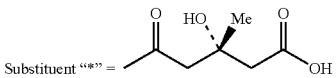

Compounds 27, 28 and 29 illustrate the structures of reference compounds in table 1

TABLE 3c

Further example compounds of the invention of the formula IIIb.

| Compound | Structure |
|---|---|
| 20 | 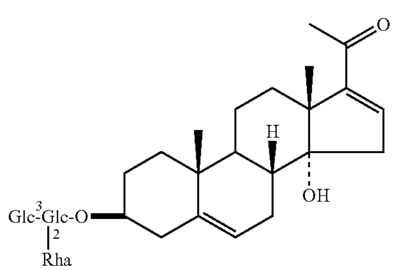 |
| 21 | 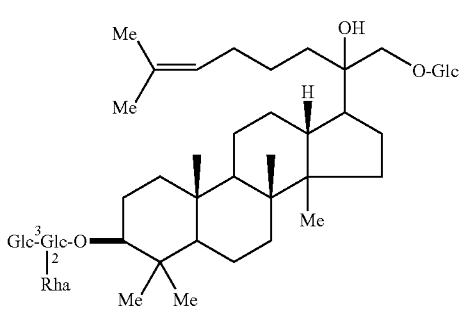 |

TABLE 3c-continued

Further example compounds of the invention of the formula IIIb.

| Compound | Structure |
|---|---|
| 22 | 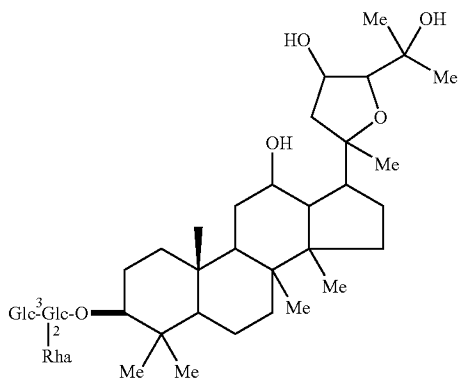 |
| 23 | 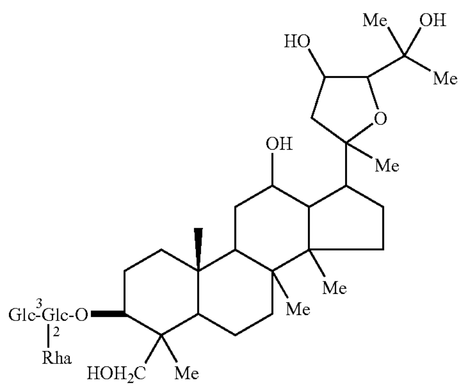 |
| 24 | 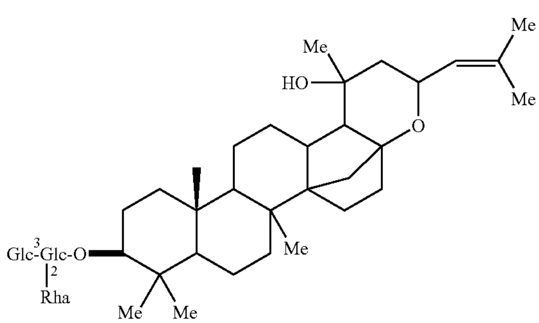 |
| 25 | 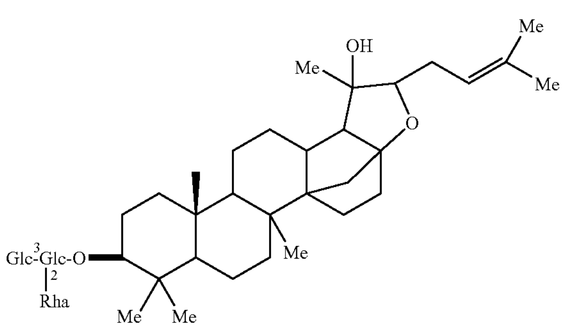 |

TABLE 3c-continued

Further example compounds of the invention of the formula IIIb.

| Compound | Structure |
|---|---|
| 26 | [Structure: steroid with HO, Me, OH, O, Me, Me groups; Glc-³Glc-O with ²Rha substituent; Me, Me groups] |

TABLE 4

Key to compound names of compounds of the
formula IIIb and example references.

| Compound | Example references | Compound name |
|---|---|---|
| 1b | 1 | Protogracillin |
| 2b | 1, 37 | protoneogracillin |
| 3b | 1, 20, 21, 22 | Methylprotogracillin |
| 4b | 1 | Methylprotoneogracillin |
| 5b | 23 | Pseudoprotogracillin |
| 6b | 25 | Dracenoside Q |
| 7b | 25 | Dioscoreside E |
| 8b | 25 | Dracenoside P |
| 9b | 24 | Tuberoside C |
| 10b | 26 | Icogenin |
| 11b | 28, 27, 7, 29, 37 | Gracillin |
| 12b | 30, 38 | Collettiside IV ((25S) Gracillin) |
| 13b | 29, 39 | 17-OH Gracillin |
| 14b | 25 | Dracaenoside H |
| 15b | 25 | Dracaenoside L |
| 16b | 25 | Dracaenoside I |
| 17b | 29, 39 | Not named |
| 18b | 31 | Lilioglycoside H |
| 19b | 31 | Lilioglycoside I |
| 20b | 25 | Dracaenoside D |
| 21b | 32 | Not named |
| 22b | 33 | Neoalsoside A |
| 23b | 33 | Neoalsoside C |
| 24b | 34 | Hoduloside V |
| 25b | 35 | Not named |
| 26b | 36 | Lotoside II |

The present invention will now be described further by reference to the following non-limiting Examples, Schemes and Figures. Further embodiments falling within the scope of the claim will occur to those skilled in the art in the light of these.

FIGURES

Figure 1:
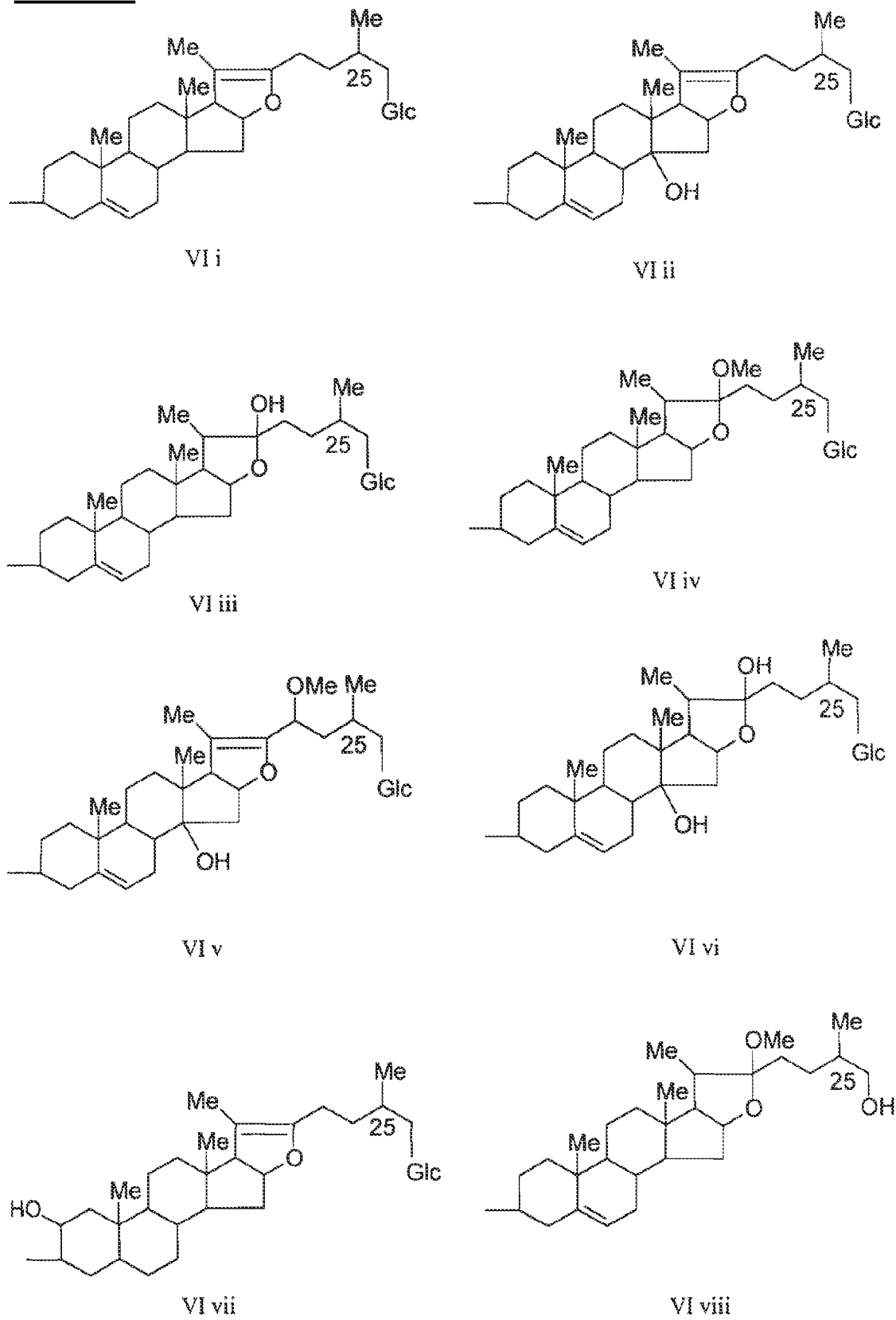
FIG. 1 illustrates preferred steroid moieties Z of formula VI a and VI b.
Figure 2:
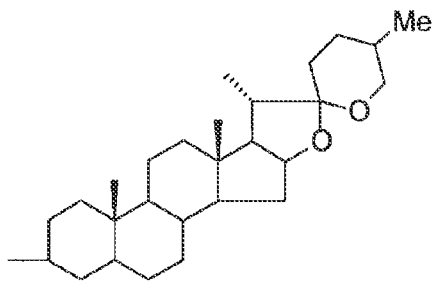
FIG. 2 illustrates preferred steroidal moieties Z of the formula VI c.
Figure 2:
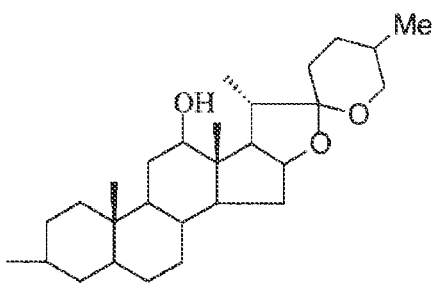
Figure 2:
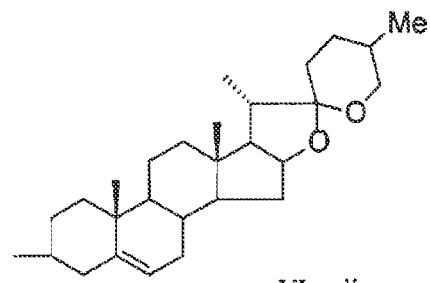
Figure 2:
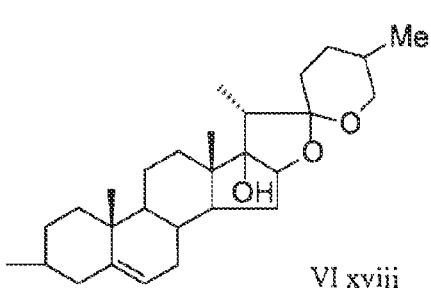
Figure 2:
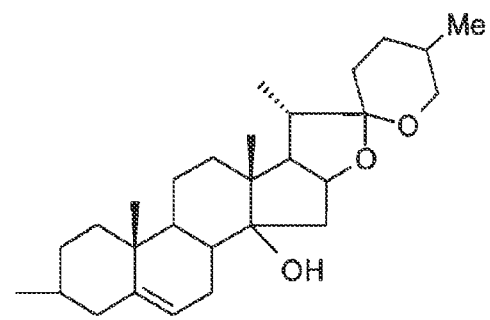
Figure 2:
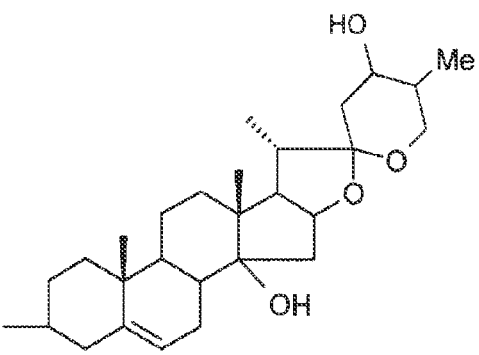
Figure 2:
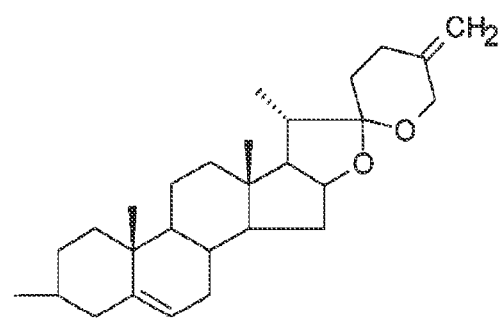
Figure 2:
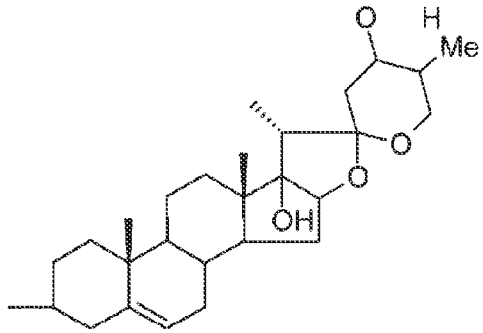
Figure 3:
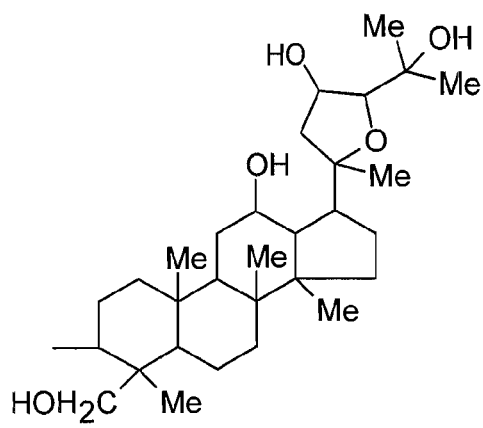
FIG. 3 illustrates preferred steroidal moieties Z of the formula VI
Figure 3:
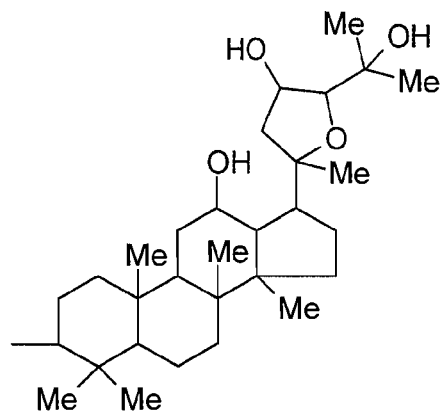
Figure 3:
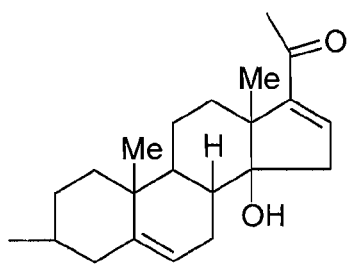
Figure 3:
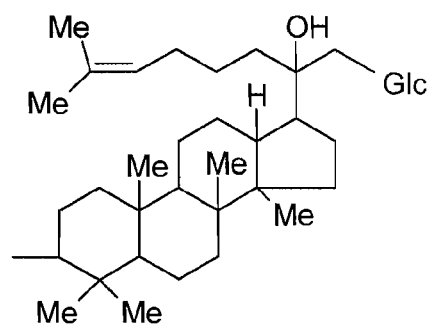
Figure 3:
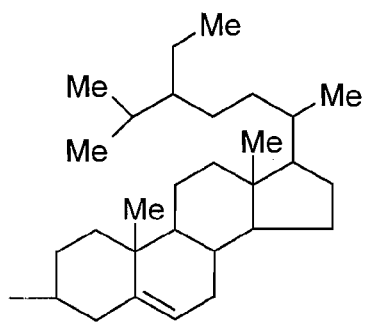
Figure 4A:
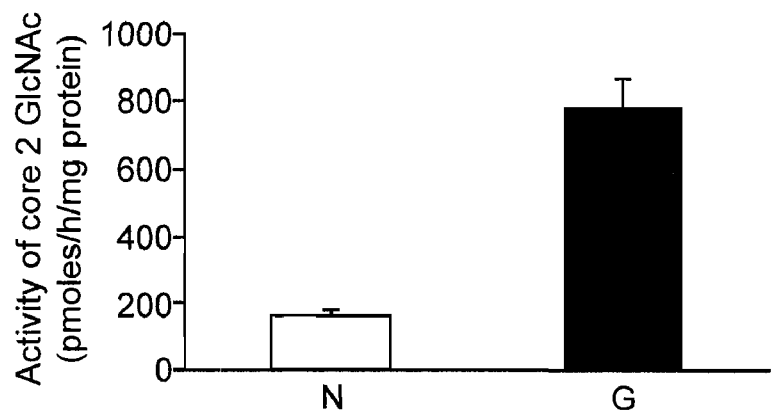

FIG. 4a is a graph illustrating that the activity of the enzyme core 2 GlcNAc-T can be induced by glucose. Human leukocytes (U937) were exposed to normal (5.8 mM) and high glucose (15 mM) for 24 hours at 37° C. Then the cells were lysed and the activity of core 2 GlcNAc-T measured. The data is presented as the means±s.e.m., n=28, the asterisk representing a significant difference (P<0.05).

Figure 4B:
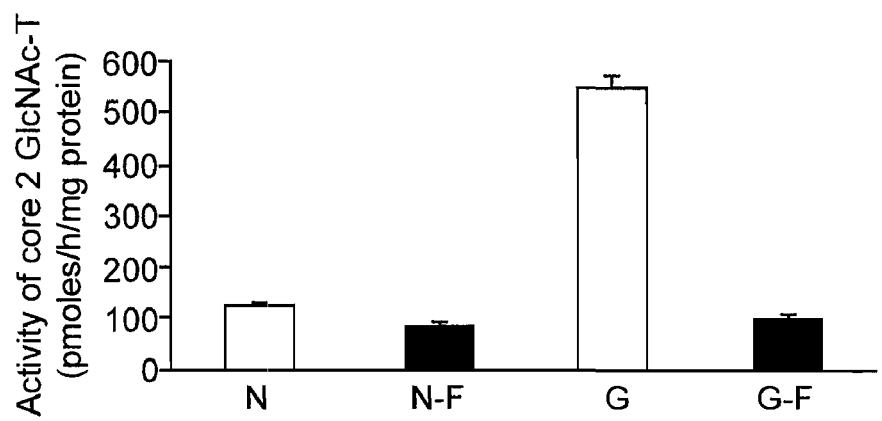

FIG. 4b is a graph illustrating that crude extract F1 prepared from fenugreek seeds inhibits glucose-induced core 2 GlcNAc-T activity. Human leukocytes (U937) were exposed to normal (N, 5.8 mM; n=3) and high glucose (G, 15 mM; n=3) in the presence of fenugreek extract (1:1000 dilution; N-F, G-F). After 24 hours incubation, the activity of core 2 GlcNAc-T was determined in leukocyte cell lysates. The activity of core 2 GlcNAc-T is presented as pmoles/h/mg protein.

Figure 4C:
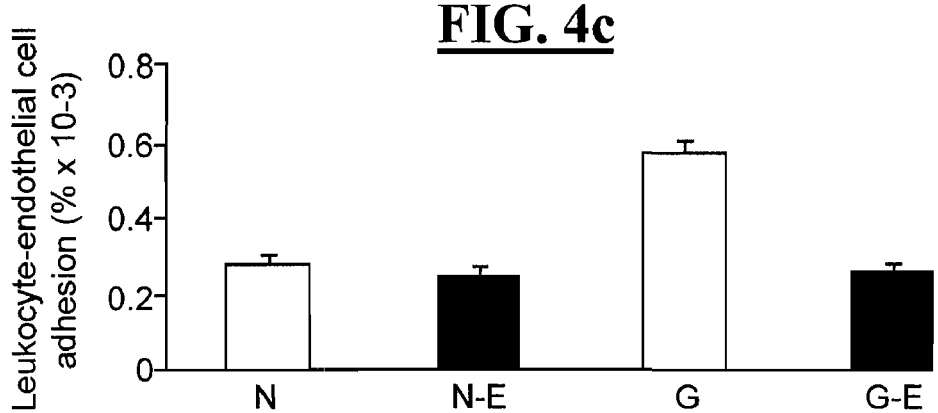

FIG. 4c is a graph illustrating that crude extract F1 prepared from fenugreek seeds inhibits adherence of human leukocytes (U937) to cultured retinal capillary endothelial cells. After exposure to elevated glucose (15 mM) the level of leukocyte-endothelial cell adhesion was determined by labelling the leukocytes with carboxyfluorescein. The data is presented as the mean±s.e.m., n=3, the asterisk representing a significant difference (P<0.05).

Figure 5:
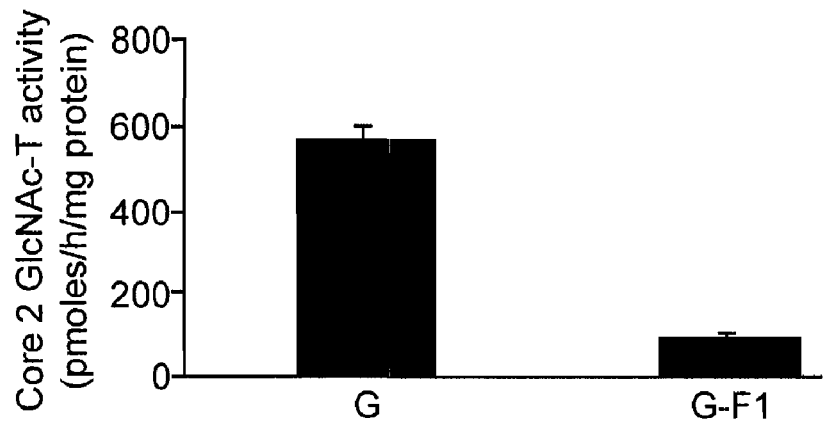

FIG. 5 is a graph illustrating that crude extract F1 prepared from fenugreek seeds inhibits core 2 GlcNAc-T activity. Human leukocytes (U937) were exposed to 15 mM glucose for 24 hours at 37° C. and the activity of core 2 GlcNAc-T was measured in leukocyte cell lysate in the presence of crude fenugreek seed extract (G-F1 ; 1:1000 dilution). The level of core 2 GlcNAc-T activity was measured by determining the formation of core 2 oligosaccharide
(attachment of β1,6-linked GlcNAc to the Galβ1, 3GlcNAc-acceptor). The data is presented as mean±s.e.m. of three separate experiments.

Figure 6:
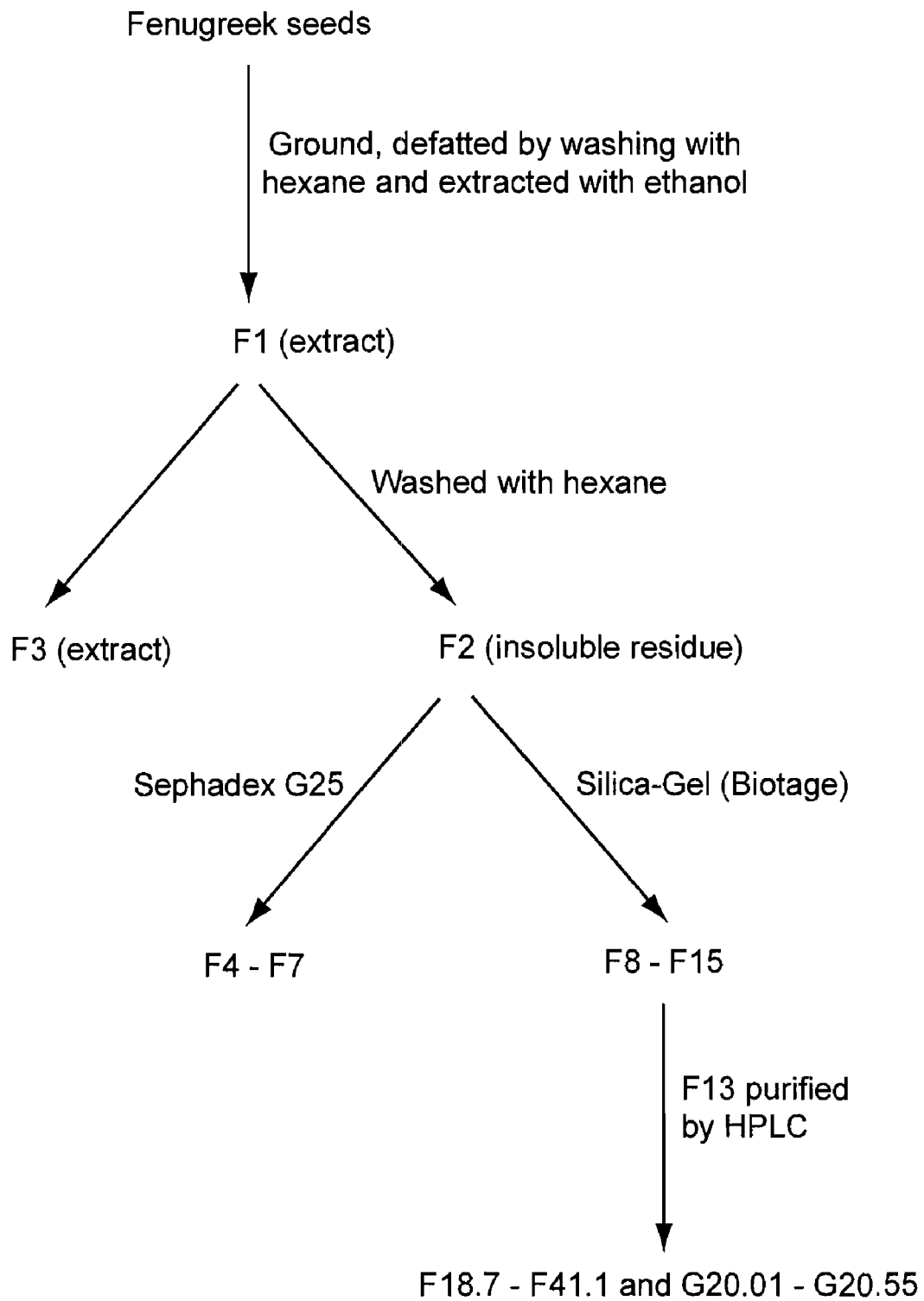

FIG. 6 is a schematic flow chart illustrating the extraction of fenugreek seeds and the subsequent purification of the fenugreek seed extract.

Figure 7:
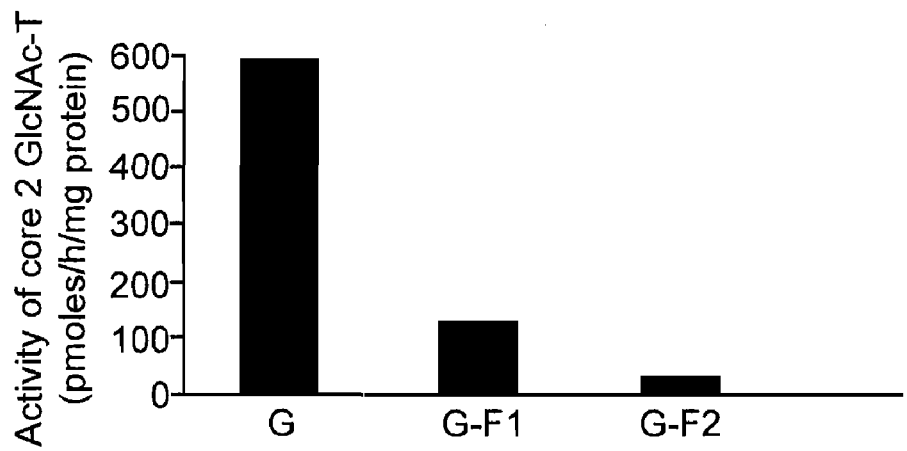

FIG. 7 is a graph illustrating the inhibitory effect of crude fenugreek seed extract F1 and sub-fraction F2 purified from crude extract F1 on glucose-induced activity of core 2 GlcNAc-T in human leukocytes (U937). Cells were exposed to elevated glucose (15 mM) in the presence and absence of sub-fractions F1 and F2. After 24 hours incubation, the core 2 GlcNAc-T activity was determined in leukocyte cell lysates. The data represents the mean of two separate experiments.

Figure 8A:
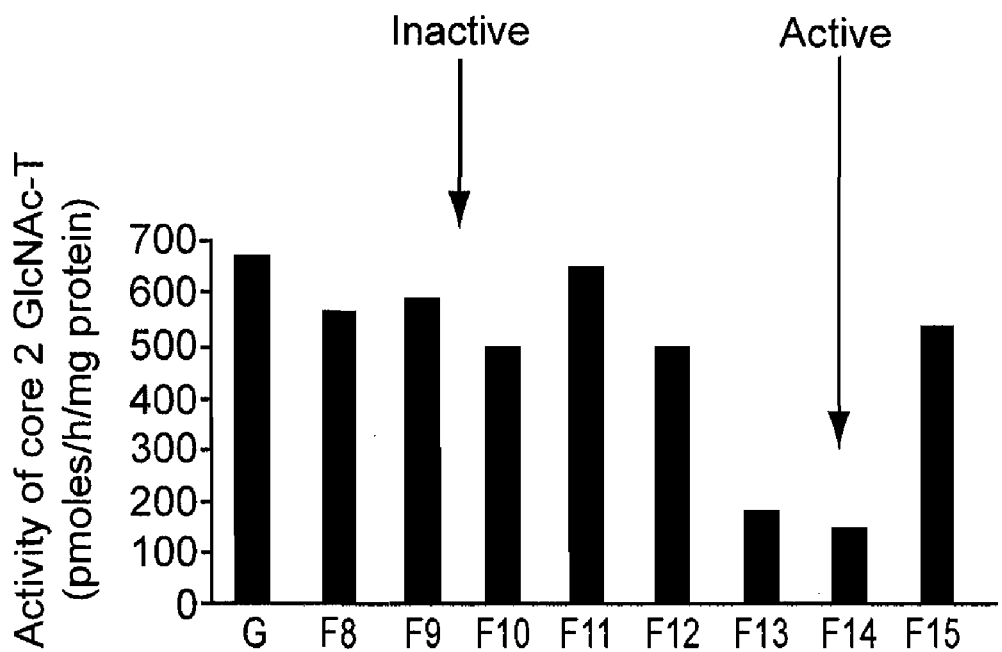
Figure 8B:
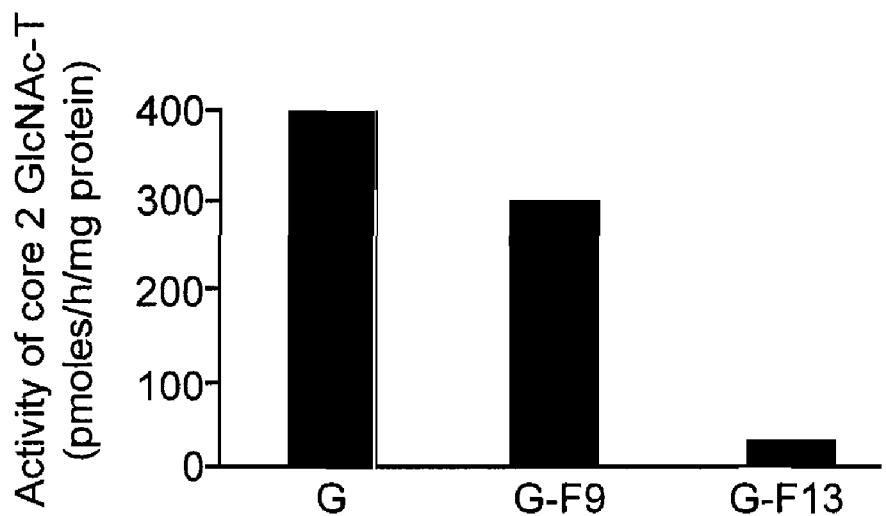

FIGS. 8a and 8b are graphs illustrating the inhibitory effect of sub-fractions F8-F15 purified from crude extract F1 by silica-gel flash chromatography (Biotage) on glucose induced activity of core 2 GlcNAc-T in human leukocytes (U937). Cells were exposed to elevated glucose (G, 15 mM) in the presence of the sub-fractions. After 24 hours incubation, the core 2 GlcNAc-T activity was determined in leukocyte cell lysates. The data is presented as the mean±s.e.m., n=3, the asterisk representing a significant difference (P<0.05).

Figure 9:
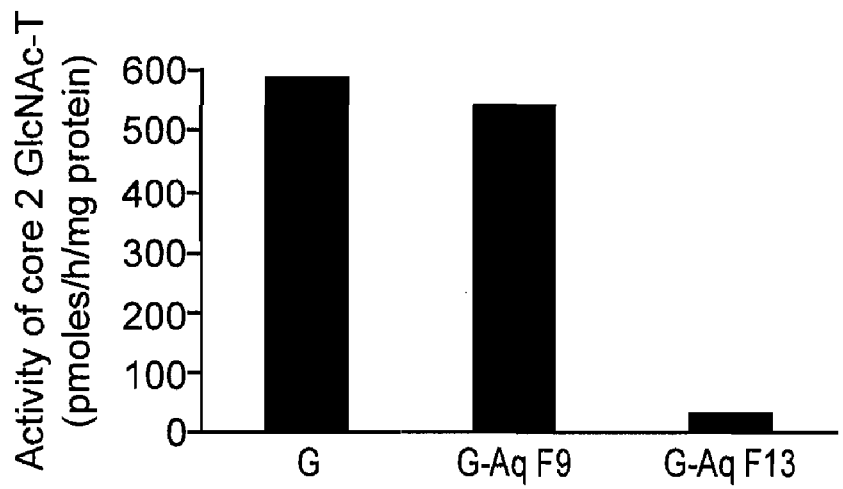

FIG. 9 is a graph illustrating that the aqueous phase of sub-fraction F13 inhibits glucose induced activity of core 2 GlcNAc-T in human leukocytes (U937). Sub-fractions F9 and F13 were thoroughly mixed with dichloromethane and the aqueous phase was filter sterilised and used in the cell-based assay for core 2 GlcNAc-T activity. Human leukocytes were exposed to elevated D-glucose (15 mM) in the presence and absence of the aqueous phases of sub-fractions F9 and F13. The results are presented as the mean of two separate experiments.

Figure 10:
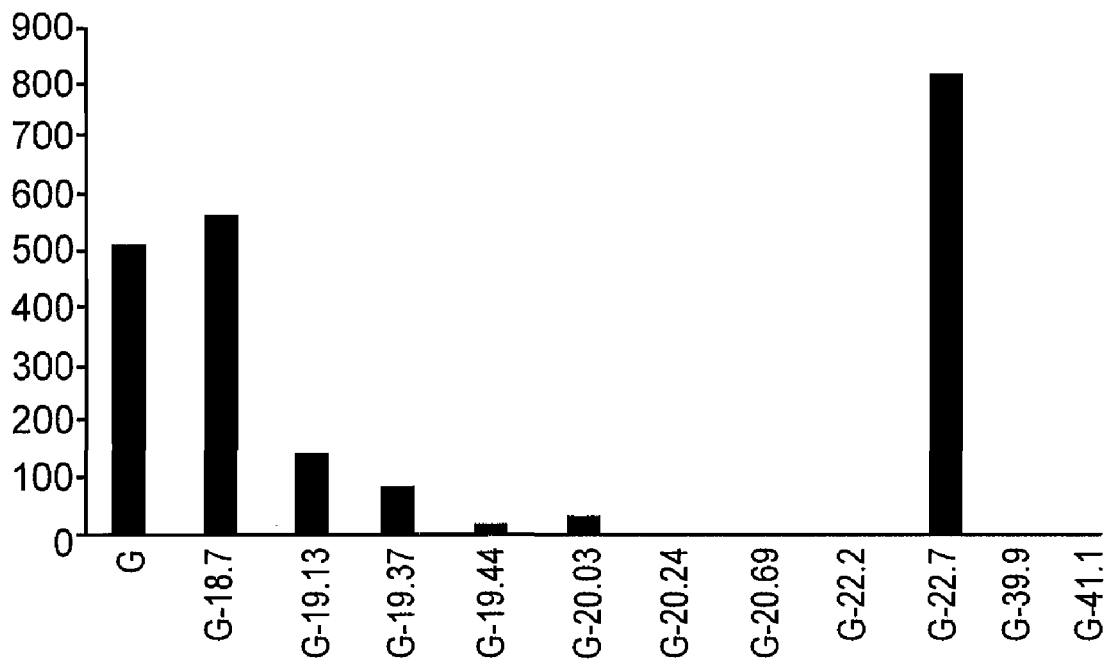
Figure 11:
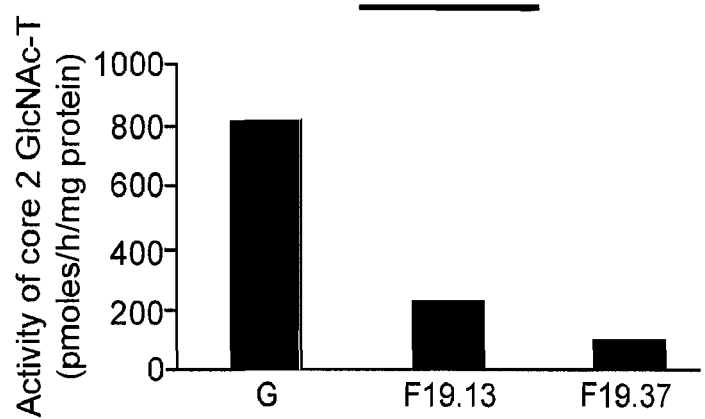

FIG. 10 is a graph illustrating the inhibitory effect on glucose-induced activity of core 2 GlcNAc-T of sub-fractions purified from the aqueous phase of sub-fraction F 13 by HPLC with retention times F18.7-F41.1. Human leukocytes (U937) were exposed to elevated D-glucose (15 mM) in the presence and absence of the HPLC sub-fractions with retention times F18.7-F41.1. The data presented is from one experiment. Sub-fractions G20.24, G20.69, G22.2, G39.9 and G41.1 (represented without a column in FIG. 8) were not tested for their inhibitory effect on glucose-induced activity of core 2 GlcNAc-T. FIG. 11 is a graph illustrating the inhibitory effect of HPLC sub-fractions with retention times F19.13 and F19.37. Human leukocytes (U937) were exposed to elevated D-glucose (15 mM) for 24 hours in the presence and absence of the sub-fractions with retention times F19.13 and F19.37 (1:1000 dilution). The data is presented as the mean±s.e.m., n=3, the asterisk representing a significant difference (P<0.05).

Figure 12:
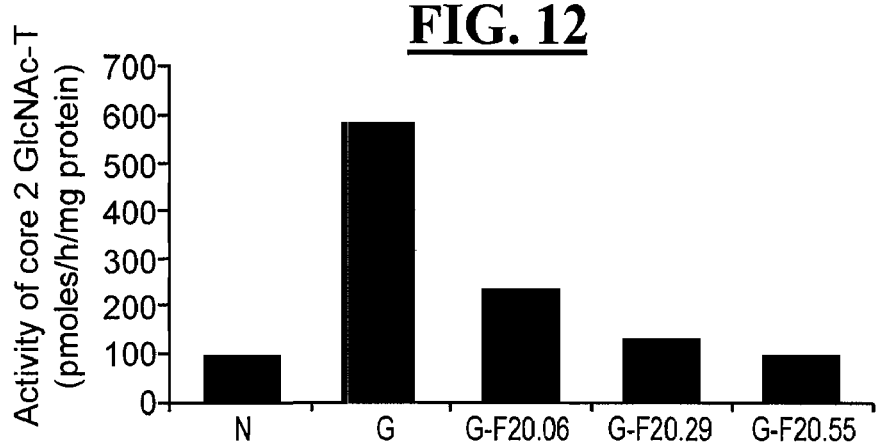

FIG. 12 is a graph illustrating the inhibitory effect on glucose-induced activity of core 2 GlcNAc-T of sub-fractions purified from the aqueous phase of sub-fraction F13 by HPLC with retention times F20.01, F20.29 and F20.55. Human leukocytes (U937) were exposed to elevated D-glucose (15 mM) in the presence and absence of the sub-fractions with retention times F20.01, F20.29 and F20.55 and the activity of core 2 GlcNAc-T was measured after 24 hours. The data is the mean of two separate experiments.

Figure 13:
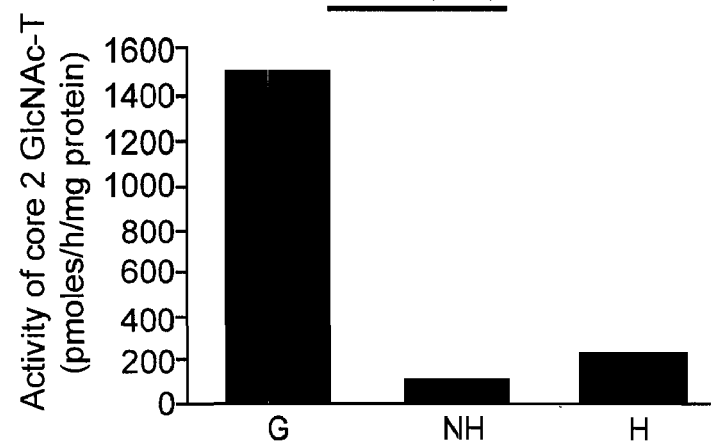

FIG. 13 is a graph illustrating that sub-fraction F20.55 inhibits core 2 GlcNAc-T in a cell-free assay. After exposing human leukocytes (U937) to 15 mM glucose for 24 hours at 37° C., the cells were lysed and then exposed to heated (H, 100° C.) and non-heated (NH) sub-fraction F20.55 (1:500 dilution). After 30 minutes exposure at 37° C., the activity of core 2 GlcNAc-T was measured. The level of core 2 GlcNAc-T activity was measured by determining the formation of core 2 oligosaccharide (attachment of ($3$-1,6-linked GlcNAc to the Gal-1,3-GlcNAc-acceptor). The data is presented as mean±s.e.m. of three separate experiments.

Figure 14A:
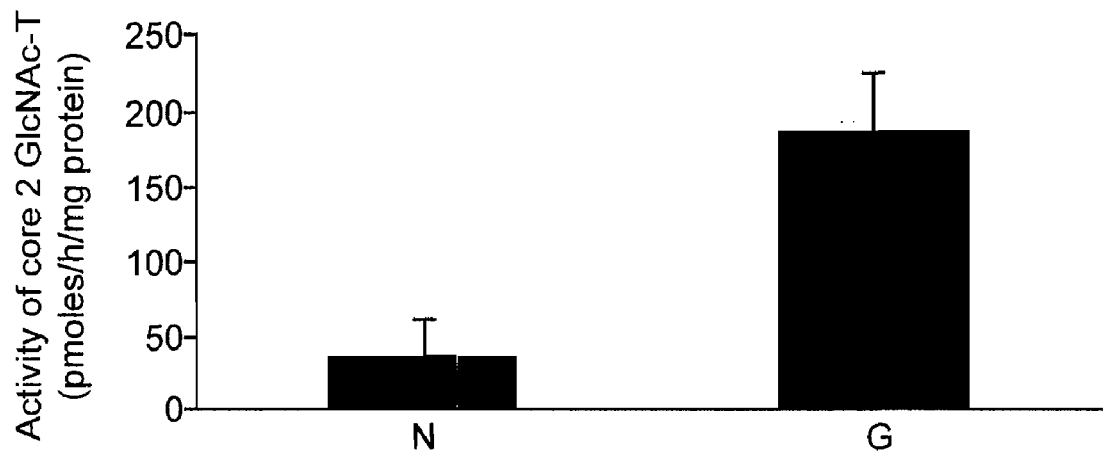
Figure 14B:
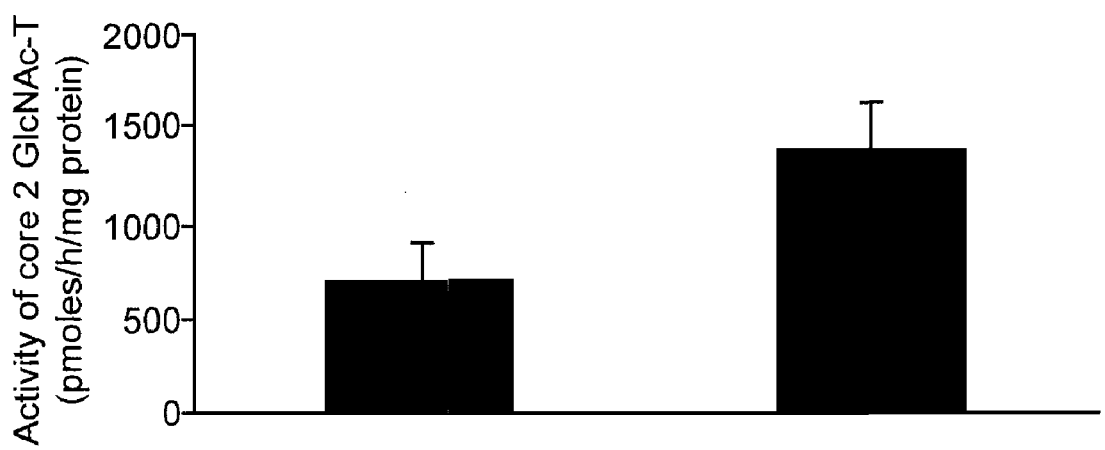

FIGS. 14a and 14b are graphs illustrating that elevated glucose increases core 2 GlcNAc-T activity in cultured bovine retinal vascular cells, namely capillary pericytes (FIG. 14a) and capillary endothelial cells (FIG. 14b). Near confluent cultures were exposed to normal glucose (N, 5.8 mM) and high glucose (G, 15 mM) for 24 hours at 37° C. The cells were lysed and the activity of core GlcNAc-T measured in cell lysates. The data is presented as the mean±s.e.m. (n=3-4), the asterisk representing a significant difference (P<0.05).

Figure 15A:
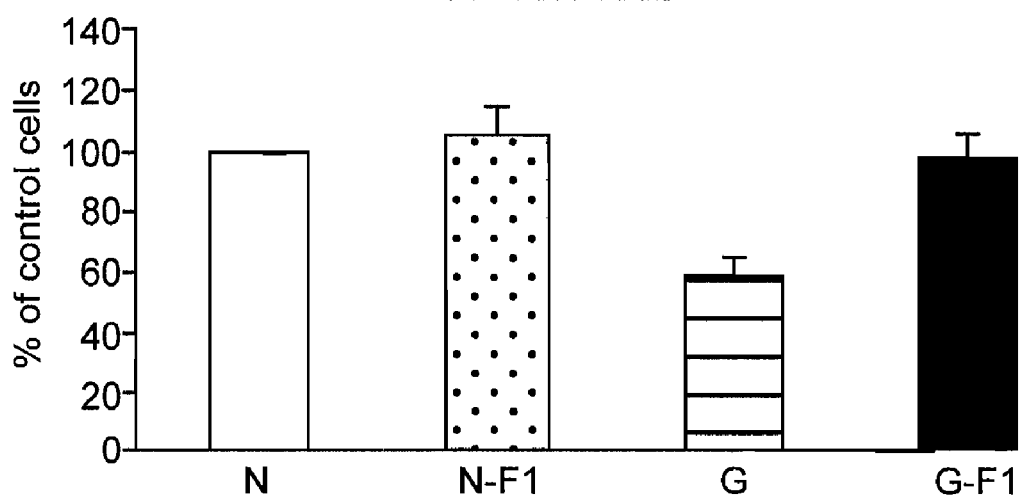
Figure 15B:
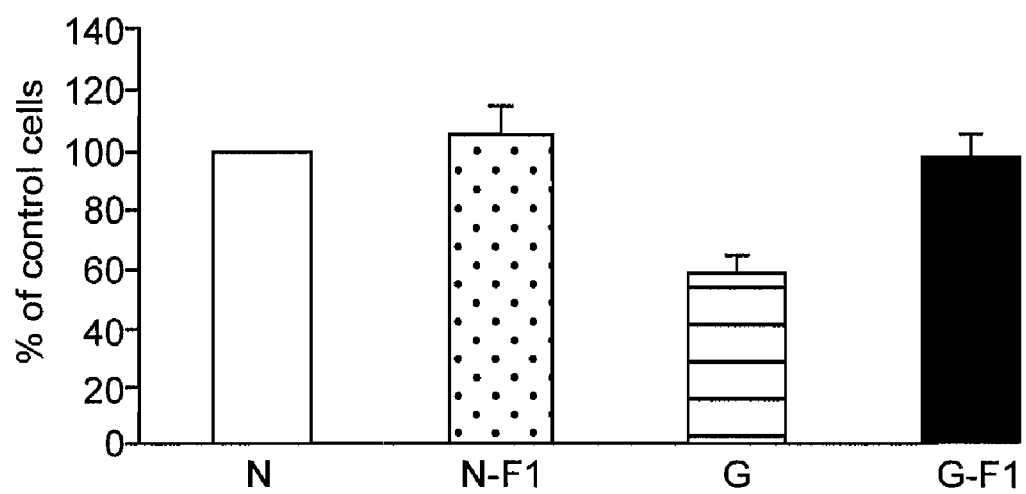

FIGS. 15a and 15b are graphs illustrating that a crude extract F1 of fenugreek seeds prevents glucose-induced toxicity in cultured bovine retinal vascular cells, namely capillary pericytes (FIG. 15a) and capillary endothelial cells (FIG. 15b). Cells were exposed to normal (N, 5.8 mM) and high glucose (G, 25 mM) in the presence (N-F, G-F) and absence (N, G) of the fenugreek seed extract. After 4 days incubation, the number of viable cells was determined using a haemocytometer and trypan blue exclusion. The data is presented as the mean±s.e.m., n=18 separate experiments, the asterisk representing a significant difference (P<0.05).

Figure 16:
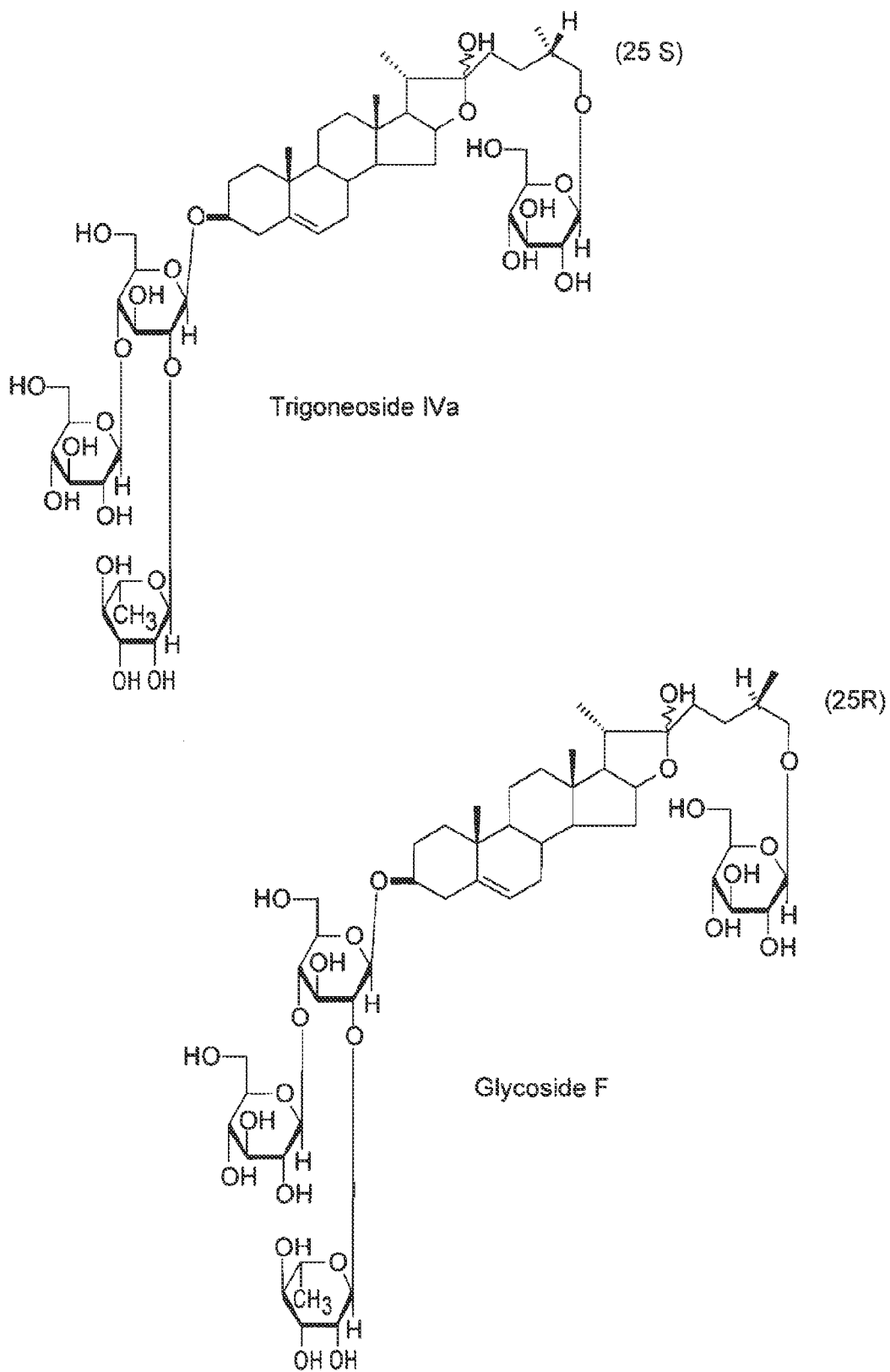
Figure 17A:
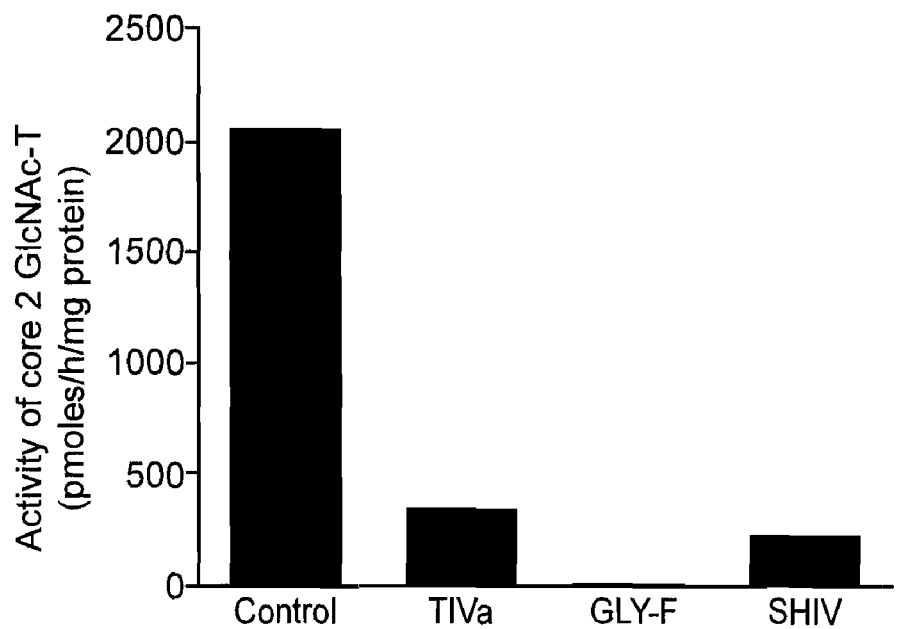
Figure 17B:
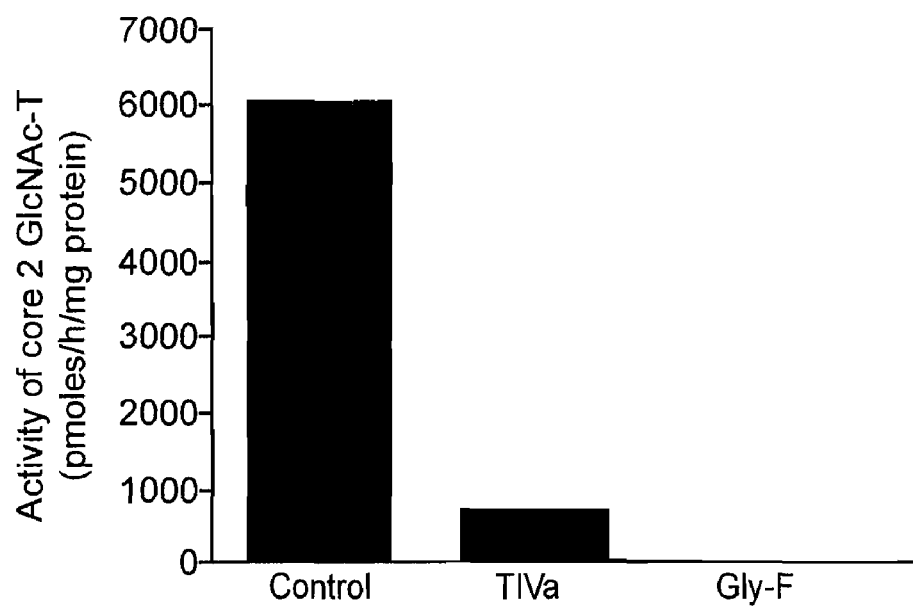

FIG. 16 illustrates the structures of the five compounds isolated from fenugreek seeds and shatavarin IV FIG. 17a and FIG. 17b are graphs illustrating the effect of purified trigoneoside IVa, glycoside F, and shatavarin IV on Core 2 GlcNAc-T activity in cell free (FIG. 17a) and cell based (FIG. 17b) assays. In cell free assays heart lysate from BB rats were incubated in the presence, and absence of 20 ng/ml of each compound. After 1 h incubation at 37° C., the activity of core 2 GlcNAc-T was measured, and expressed as pmoles/h/mg protein. The results are the mean of 3-5 separate experiments. In cell based assays human leukocytes (U937 cells) were exposed to 8 pg/ml human recombinant TNF-alpha in the presence and absence of 20 ng/ml of the test compound. After 24 h incubation, the activity of core 2 GlcNAc-T was measured, and expressed as pmoles/h/mg protein.

Figure 18:
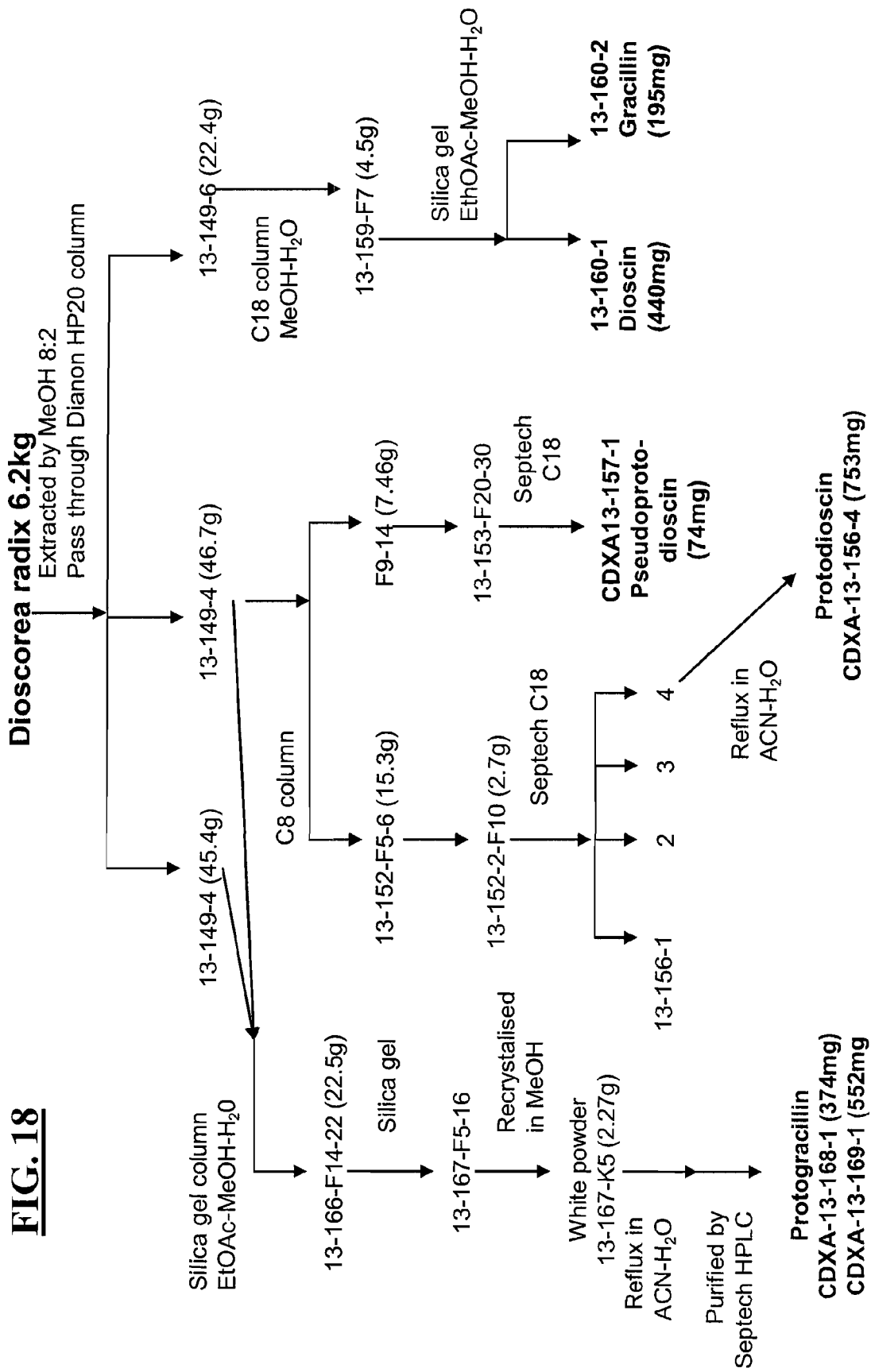

FIG. 18 is a schematic diagram illustrating the process of purifying protogracillin and gracillin for *Dioscorea radix* tissue. Purification of dioscin is included for reference. Also illustrated are the purification of protodioscin and pseudoprotodioscin, which may also be purified from *Dioscorea radix*.

Figure 19:
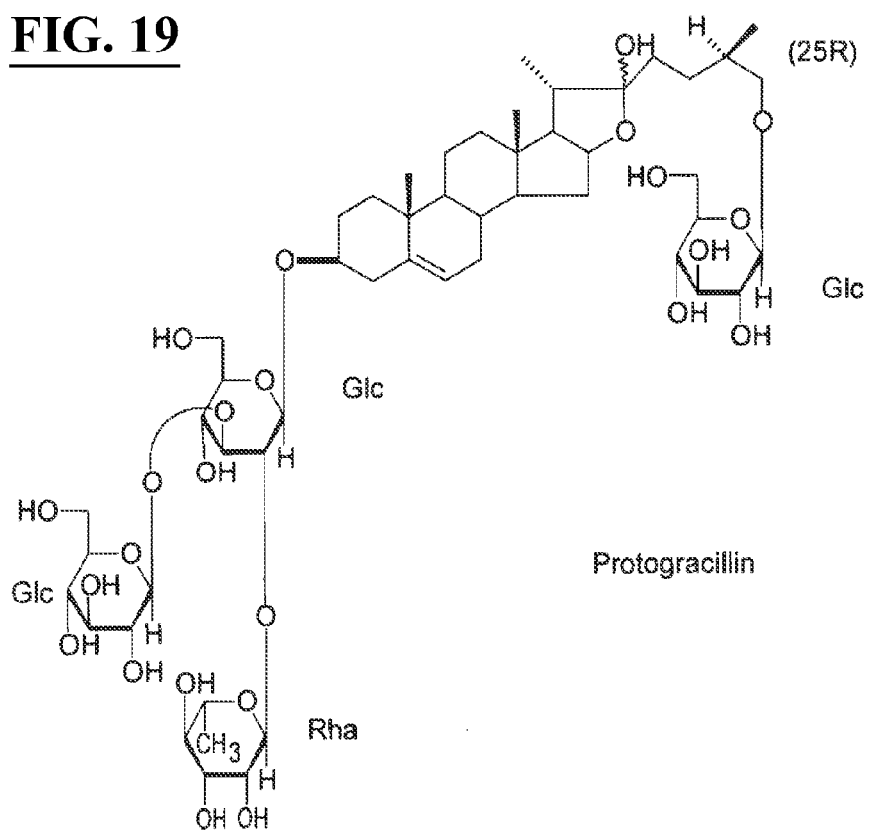
Figure 19:
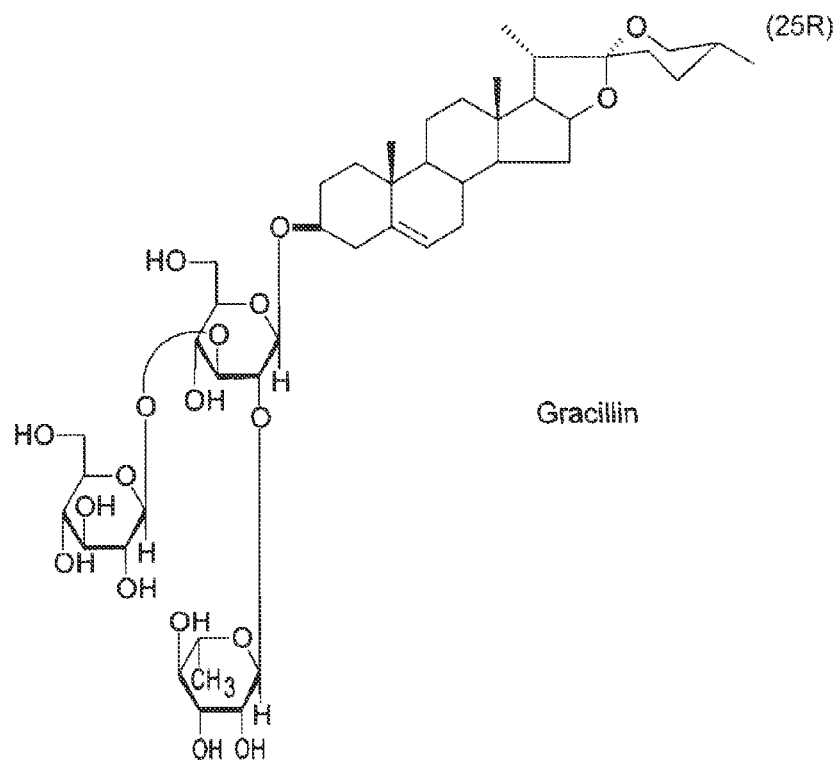

FIG. 19 illustrates the structures of protogracillin and gracillin isolated from *D. radix*.

Figure 20:
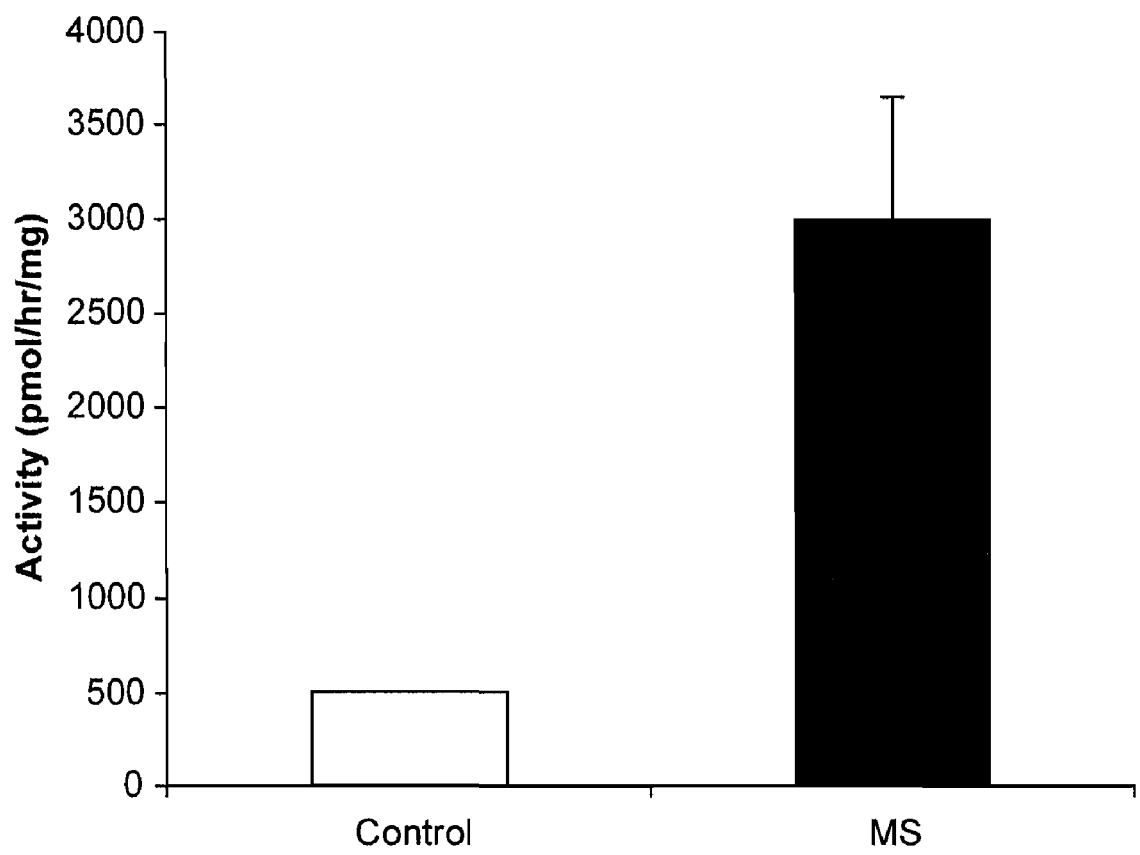

FIG. 20 is a graph illustrating the levels of Core 2 GlcNAc-T activity in leukocytes from healthy control individuals and subjects with newly diagnosed MS.

Figure 21:
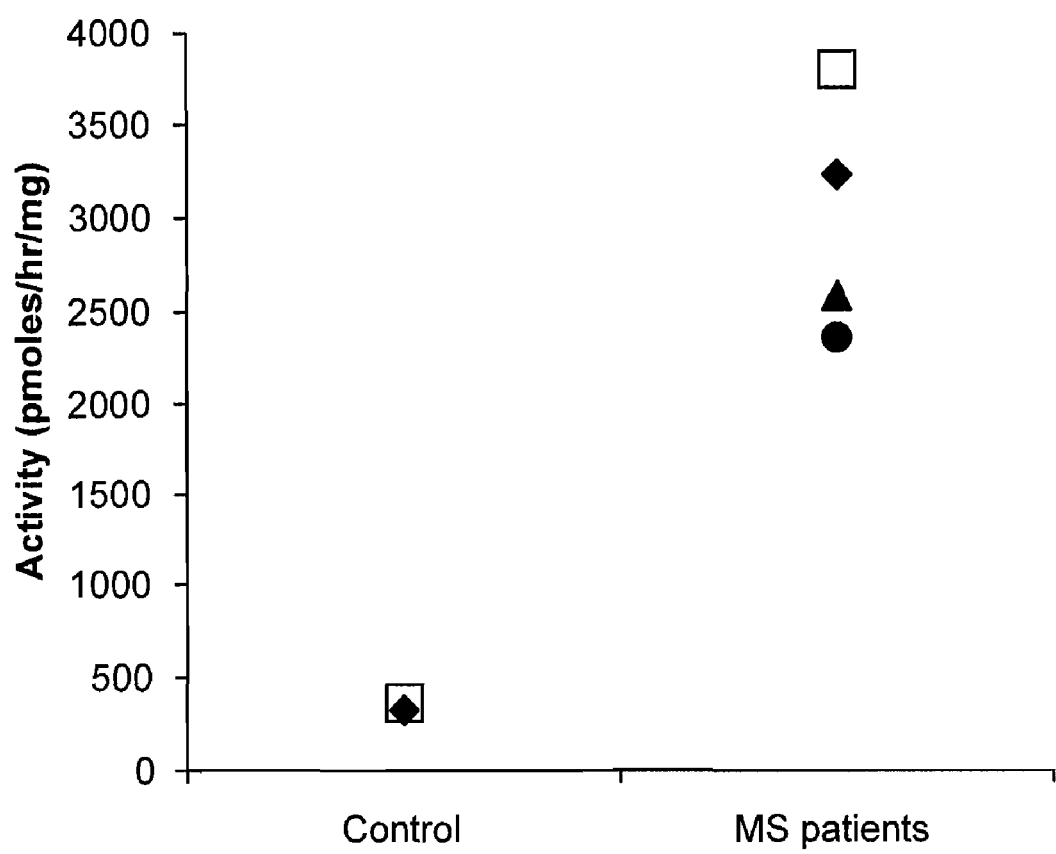

FIG. 21 is a graph illustrating the data of FIG. 20 as a scatter plot.

EXPERIMENTAL EXAMPLES

All compounds used herein were supplied by Chromadex Inc. 2952 S. Daimler Street Santa Ana Calif. 92705. Compounds used were at least 88% pure, except those prepared under example 8

1. Cell Culture

Bovine retinal capillary endothelial cells (BREC) and pericytes (BRP) were established from bovine retinas dissected from eyes of freshly slaughtered cattle as described previously. Briefly, the isolated retinas were homogenised in serum-free minimal essential medium (MEM, Gibco, Paisley, UK) and filtered through 85 μm nylon mesh. The trapped microvessels were digested with collagenase-dispase (1 mg/ml) for 30 minutes (BRP) and 90 minutes (BREC) at 37° C. and filtered through a 53 μm nylon mesh. For growth of endothelial cells (BREC), the digested microvessels were plated in gelatine coated tissue culture flasks and maintained in MEM supplemented with 10% pooled human serum, 2 mM glutamine, 100 Mimi penicillin and 100 μg/ml streptomycin. For growth of pericytes (BRP), the microvessels were plated in tissue culture flasks in growth medium supplemented with 10% foetal calf serum. The cells were used at passage 2-3. The cells were characterised using morphological criteria and by immunostaining with an antibody against factor VIII related antigen and 3G5-pericyte marker.

The human leukocytic cell-line (U937) was cultured in RPMI supplemented with 10% foetal calf serum, 2 mM glutamine, 100 IU/ml penicillin and 100 μg/ml streptomycin.

The human leukocytic cell-line (U937) is cultured in RPMI supplemented with 10% foetal calf serum, 2 mM glutamine, 100 IU/ml penicillin and 100 μg/ml streptomycin.

For Glucose induction of Core 2 GlcNAc-T leukocytes (U937 cells) are exposed to normal glucose (5.8 mM) or high glucose (15 mM) for 24 hours at 37° C. After incubation, the cells maybe lysed and frozen at −20° C. until used for the measurement of core 2 GlcNAc-T. or used immediately. For TNF-α induction of core 2 GlcNAc-T, Human leukocytes (U937 cells) are exposed to human recombinant TNF-alpha (8 pg/ml) in the presence and absence of test compounds After 24 h incubation, the activity of core 2 GlcNAc-T was measured, and expressed as pmoles/h/mg protein. For cell free assay of core 2 GlcNAc-T heart lysates from either from TNF-alpha over expressing transgenic mice (female, B6.5JL-Tg (TNF) supplied by Taconic-M+B, Bomholtveg 10, 8680 Ry, Denmark) or from BB rats (Festing 1979) are exposed to various concentrations of test compound for 1 h at 37° C. Activity of core 2

GlcNAc-T is measured, and expressed as pmoles/h/mg protein.

2. Cell-Based Assay of Core 2 GlcNAc-T Activity

To investigate the potential of fenugreek to pharmacologically inhibit core 2 GlcNAc-T, enzyme activity was measured in leukocytes exposed to normal glucose (5.8 mM) and high glucose (15 mM) for 24 hours at 37° C. After incubation, the cells were lysed and frozen at −20° C. until used for the measurement of core 2 GlcNAc-T. The activity of core 2 GlcNAc-T in cultured bovine retinal capillary pericytes (BRP) and endothelial cells (BREC) was also measured.

3. Cell-Free Assay of Core 2 GlcNAc-T Activity

Core 2 GlcNAc-T immobilised on Sepharose beads were used for this assay. For core 2 GlcNAc-T immunoprecipitation, as well as for Western blots, a polyclonal antibody against core 2 GlcNAc-T was used. Cells were lysed on ice in the following lysis buffer: 20 mM Tris-HCL, pH 7.4/1% Triton X-100, 150 mM NaCl, 1 mM EDTA, 1 mM EGTA, 0.2 mM sodium vandate, 1 mM PMSF 1 µg/ml aprotinin, 10 µg/ml leupeptin. The lysate was incubated at 4° C. for 20 minutes with constant agitation and insoluble material removed by centrifugation (14,000 g for 5 minutes at 4° C.). The clarified lysate was incubated with staphylococcal protein A-Sepharose CL-4B conjugated primary antibody for 2 hours with constant agitation at 4° C. The immunoprecipitates were washed with Tris buffered saline (10 mM Tris-HCL, pH 7.4, 150 mM NaCl) containing 0.5% Triton X-100 and used in the measurement of core 2 GlcNAc-T in the presence and absence of potential inhibitors.

4. Measurement of Core 2 GlcNAc-T Activity

To measure core 2 GlcNAc-T activity, leukocytes were washed in PES, frozen and lysed in 0.9% Triton X-100 at 0° C. The activity of core 2 GlcNAc-T was measured as described previously (Chibber, *Diabetes* 49, 1724-1730 (2000)). Briefly, the reaction was performed in a reaction mixture containing 50 mM 2(N-morpholino)ethanesulfonic acid (MES, Sigma, Dorset, UK), pH 7.0, 1 mM UDP-6 [$^1$H]-N-acetylglucosamine (16,000 dpm/nmol, NEN Life Science Products, Hounslow, UK), 0.1 M GlcNAc (Sigma, Dorset, Okla.), 1 mM Galβ1-3GalNAcα-p-nitrophenol (Sigma, Dorset, UK) as substrate, and 16 µA of cell lysate (100-200 µg protein) for a final volume of 32 pd. After incubating the mixture for 1 hour at 37° C., the reaction was terminated with 1 ml of ice-cold distilled water and processed on a C18 Sep-Pak column (Waters-Millipore, Watford, UK). After washing the column with 20 ml of distilled water, the product was eluted with 5 ml of methanol. The radioactivity of the samples was counted in a liquid scintillation β-counter (LKB-Wallac, London, UK). Endogenous activity of core 2 GlcNAc-T was measured in the absence of the added acceptor. The specific activity was expressed as pmoles/h/mg of cell protein. In each case, the protein concentration was determined with BioRad protein assay (BioRad, Hertfordshire, UK).

5. Leukocyte-Endothelial Adhesion Assay

Adhesion of leukocytes to endothelial cells was examined by labelling with carboxyfluorescein (Molecular Probe, UK). The assay is well established (Chibber, *Diabetes* 49, 1724-1730 (2000)). Briefly, endothelial cells were grown to a confluent state in order to provide an endothelial cell surface for the adhesion of the carboxyfluorescein-labelled leukocytes (U937). After treatment, the leukocytes were centrifuged (14 000 g for 1 minute) and washed twice with serum-free RPML The cells were then resuspended in 1 ml of serum-free RPMI containing 50 µg/ml carboxyfluorescein. The cells were counted with a haemocytometer and a known number added to the endothelial cells. After 30 minutes incubation at 37° C., non-adherent leukocytes were removed by washing with serum-free RPMI and the dishes fixed in 3.7% formalin in PBS. Attached leukocytes were counted in 10 random high-powered fields (×100) by fluorescence microscopy. The results were expressed as percentage of adherent leukocytes/field.

6. Glucose Toxicity

BRP and BREC were plated in 3 cm tissue culture dishes and incubated in growth medium for 24 hours at 37° C. Then the cells were incubated in fresh growth medium containing normal glucose (5.8 mM) or elevated glucose (25 mM) in the absence or presence of fenugreek sub-fractions. After 4 days incubation, the number of viable cells was counted using a haemocytometer and trypan blue and the results expressed as percentage of control (5.8 mM glucose). After treatment, some of the cells were stored for measurement of core 2 GlcNAc-T activity.

7. Biological Activity of Crude Fenugreek Seed Extract

As shown in FIG. 4*a*, 24 hour exposure to elevated D-glucose significantly increases the activity of core 2 GlcNAc-T in human leukocytes (U937). It has now been found that crude extract prepared from fenugreek seeds has the potential to inhibit glucose-induced activity of core 2 GlcNAc-T in human leukocytes (FIG. 4*b*) and leukocyte-endothelial cell adhesion (FIG. 4*c*). Leukocyte-endothelial cell adhesion was measured by adding a known number of leukocytes stained with carboxyfluorescein to a monolayer of retinal capillary endothelial cells. The number of attached leukocytes was then counted under a fluorescence microscope using 10-random fields.

The results illustrated in FIG. 5 were obtained by exposing human leukocytes (U937) to elevated glucose for 24 hours. The cells were then lysed, incubated with crude fenugreek seed extract F1 and core 2 GlcNAc-T activity was measured after 30 minutes incubation.

8. Extraction Example 1

Preparation and Purification of Fenugreek Seed Extracts

Fenugreek seed extracts were obtained as follows (see FIG. 6). Fenugreek seeds (Indian fenugreek seeds obtained as Methi seeds from FUDCO, 184 Ealing Road, Wembley, Middlesex, UK) were ground in a hammer mill and filtered through nylon mesh. 820 g of the dark-yellow powder obtained were defatted by continuous washing with hexane in a soxhlet apparatus for eight hours. Then the plant material was dried and continuously extracted for 8 hours with ethanol. Filtration to remove solid residues and concentration in vacuo of the ethanol yielded a semi-solid brown crude extract labelled F1 (65 g). Since this appeared to contain residual oil, 50 g of the crude extract F1 were shaken with cold hexane (500 ml). The hexane soluble material was filtered off and the solvent removed to give. F3 (15.4 g), while the insoluble residue was collected on the filter paper and dried to give F2 (27 g).

Normal phase silica-gel flash chromatography was now employed using a commercial kit (Biotage). F2 (5 g) was adsorbed onto silica-gel (5 g) and packed into the sample barrel that was connected by short tubing to the main chromatography column (20 cm×4 cm) containing silica-gel KP-Sil. The sample was eluted onto and through the column with a succession of solvents of increasing polarity consisting of varying mixtures of light petroleum (40/60), chloroform, methanol and acetone. Eluting sub-fractions were examined by TLC and similar ones pooled to give seven main eluted sub-fractions F8 to F14 representing compounds of increasing polarity. The silica was removed and shaken with 100% methanol, filtered and dried to give a residue labelled F15. Weights and approximate elution solvents for each sub-fraction are set out in Table 5.

TABLE 5

Separation of sub-fraction F2 into sub-fractions F8-F15 using flash chromatography

| Sub-fraction | Weight | Eluent |
| --- | --- | --- |
| F8 | 0.03 g | light petroleum (40/60) 100% to chloroform 100% |
| F9 | 0.10 g | chloroform:methanol 90:10 |
| F10 | 0.02 g | chloroform:methanol from 90:10 to 80:20 |
| F11 | 0.03 g | chloroform:methanol from 80:20 to 70:30 |
| F12 | 0.82 g | chloroform:methanol from 70:30 to 60:40 |
| F13 | 1.58 g | chloroform:methanol 50:50 |
| F14 | 0.01 g | chloroform:methanol:acetone 30:30:40 to acetone 100% |
| F15 | 0.14 g | eluted from silica-gel with methanol |

9. Biological Activity of Purified Fenugreek Seed Extracts

The potential of these purified sub-fractions to inhibit glucose-induced activity of core 2 GlcNAc-T in leukocytes was examined. Firstly, it was demonstrated that sub-fraction F2 can inhibit glucose-induced core 2 GlcNAc-T activity in leukocytes (FIG. 7). Further experiments demonstrated the presence of the inhibitor of core 2 GlcNAc-T in sub fractions F13 and F14 (FIGS. 8a and 8b).

Sub-fractions F9 and F13 were then analysed. An aqueous aliquot (0.5 ml) of both subtractions F9 and F13 was extracted with 1 ml of dichloromethane, the aqueous phase was removed, filter-sterilised by filtration through 0.22 µm filter and used in the cell-based assay for core 2 GlcNAc-T activity. Human leukocytes were exposed to elevated D-glucose (15 mM) in the presence and absence of the aqueous phases of sub-fractions F9 and F13, The results are presented in FIG. 9 showing the presence of the core 2 GlcNAc-T inhibitor in the aqueous phase of sub-fraction F13.

The aqueous phase of sub-fraction F13 was purified by HPLC into sub-fractions F18.7-F41.1 coded by their HPLC retention times. The aqueous phase of sub-fraction F13 was directly injected onto the HPLC operating under reversed-phase conditions (Hewlett Packard 1050^100 series), Separation was achieved with an octadecyl-bonded column with a methanol/water mobile phase, Components eluted from the column were detected by a UV detector operating at a fixed wavelength of 22 nm, These components were revealed as peaks on the chromatographic trace from the mass spectrometer detector. The sub-fractions thus obtained were concentrated in vacuo to dryness, re-dissolved in phosphate buffered saline (PBS) and filter-sterilised. Cell-based assays for core 2 GlcNAc-T activity were carried out and the results suggested the presence of core 2 GlcNAc-T inhibitor in sub-fractions F19-F20.03 (see FIGS. 10 and 11).

Subsequently larger amounts of the aqueous phase of sub-fraction F13 were purified similarly by HPLC operating under reversed-phase conditions on a phenyl-bonded column with a methanol/water mobile phase into sub-fractions with retention times of 20,01, 20.29 and 20.55, which are equivalent to sub-fractions F19.13, F19.37 and F19.44 above. Cell based assays for core 2 G1 cNAc-T activity confirmed the presence of the core 2 G1 cNAc-T inhibitor in these sub-fractions F20,01, F20.29 and F20.55 (FIG. 12). The inhibition of core 2 GlcNAc-T by HPLC purified sub-fraction F20.55 has been demonstrated using the cell-free assay system (FIG. 13). After exposing human leukocytes (U937) to 15 mM glucose for 24 hours at 37° C., the cells were lysed and then exposed to heated (H, 100° C.) and non-heated (NH) sub-fraction F20.55 (1:500 dilution). After 30 minutes exposure at 37° C., the activity of core 2 GlcNAc-T was measured. As shown in FIG. 13, it was found that sub-fraction F20.55 directly inhibits core 2 GlcNAc-T in a cell-free assay. Heating of sub-fraction F20.55 only slightly altered the level of core 2 GlcNAc-T inhibition.

10. Structural Analysis of the Core 2 GlcNAc-T Inhibitor

The core 2 GlcNAc-T inhibitor in the sub-fraction F20.55 has been identified through NMR analysis of a sample dissolved in $CD_3OD$. The following NMR experiments were performed: 1D proton, 2D DQF-COSY ($^1H$-$^1H$ correlation) [8 hours], 2D edited HSQC ('H-$^{13}C$ one-bond correlation with multiplicity editing) [22 hours], 2D TOCSY ($^1H$-$^1H$ relayed correlation) [2×8 hours].

$^1H$ and $^{13}C$ NMR data for the core 2 GlcNAc-T inhibitor in sub-fraction F20.55 is presented in Tables 6 and 7.

TABLE 6

$^1H$ NMR data (sample in deuteriopyridine)

| Sample | Assignment |
| --- | --- |
| 0.90 singlet | 18-H |
| 1.03 doublet 1 6.7 Hz | 27-H |
| 1.06 singlet | 19-H |
| 1.33 doublet J 7.1 Hz | 21-H |
| 1.77 doublet J 604 Hz | Sugar-Me |
| 2.24 dq J 6.9 Hz | 20-H |
| 5.29 multiplet | 6-H |

TABLE 7

$^{13}C$ NMR data (sample in deuteriopyridine)

| Sample | Assignment |
| --- | --- |
| Aglycone portion | |
| 37.5 | 1 |
| 30.1 | 2 |
| 78.0 | 3 |
| 38.9 | 4 |
| 140.7 | 5 |
| 121.8 | 6 |
| 32.3 | 7 |
| 31.6 | 8 |
| 50.3 | 9 |
| 37.2 | 10 |
| 21.1 | 11 |
| 39.9 | 12 |
| 40.7 | 13 |
| 56.5 | 14 |
| 32.5 | 15 |
| 81.1 | 16 |
| 63.8 | 17 |
| 16.4 | 18 |
| 19.4 | 19 |

TABLE 7-continued $^{13}$C NMR data (sample in deuteriopyridine)

| Sample | Assignment |
|---|---|
| 40.7 | 20 |
| 16.4 | 21 |
| 10.6 | 22 |
| 110.6 | 23 |
| 37.1 | 24 |
| 28.3 | 25 |
| 34.4 | 26 |
| 75.3 | 27 |
| 17.4 | 28 |
| Sugar portion | |
| 100.2 | Glc 1' |
| 77.7 | 2' |
| 76.3 | 3' |
| 81.9 | 4' |
| 77.7 | 5' |
| 62.1 | 6' |
| 102.0 | Rha 1" |
| 72.5 | 2" |
| 72.7 | 3" |
| 74.1 | 4" |
| 69.5 | 5" |
| 18.6 | 6" |
| 105.1 | Glc 1''' |
| 75.1 | 2''' |
| 78.4 | 3''' |
| 71.6 | 4''' |
| 78.2 | 5''' |
| 61.6 | 6''' |
| 105.1 | Glc 1'''' |
| 75.2 | 2'''' |
| 78.6 | 3'''' |
| 71.6 | 4'''' |
| 78.4 | 5'''' |
| 62.8 | 6'''' |

The compound of interest was identified as Trigoneoside IVa, a known constituent of Fenugreek seeds 11. Bulk Preparation of Trigoneoside IVa, Protodioscin, Compound 3 and Glycoside F from Fenugreek Seeds Crushed seeds (360 g, product of Deep Foods, Inc., Union, N.J. 07083, USA) were extracted successively with heptane (2×700 ml), acetone (4×600 ml) and MeOH (4×600 ml) by boiling under reflux for 2 hrs each. The extracts were filtered and evaporated to dryness under vacuum and analyzed by LC/MS for the presence of furostanol saponins previously reported from this plant (Yoshikawa K et al. *Chemical & Pharmaceutical Bulletin*, 40(9), 2287-91 (1992); Yoshikawa K. et al *Chemical & Pharmaceutical Bulletin*, 40(9), 2275-8 (1992), Murakami T., Chem. Pharm. Bull. (Tokyo); 48(7): 994-1000 (2000)). The methanol extract (82 g, 22.7% (w/w) of the seeds) was found to contain the target compounds.

The initial extraction of the seeds with heptane and acetone removed most of the less polar materials and improved subsequent chromatography. Further de-fatting can be accomplished by partitioning the methanol extract between butanol and water. However, methanol extract contained relatively little polar material and an enriched saponin containing fraction can be obtained by a solid phase extraction using a styrenic resin such as Diaion HP20 (or SP207, HP20SS, SP207SS, all available from Sigma-Aldrich) resin without subjecting the extract to further de-fatting.

The MeOH extract (CDXA-13-132-1, 81.2 g) was dissolved in water-MeOH (6:4, 400 ml) and loaded onto a Diaion HP20 (Supelco Diaion HP 20, 350 g, 5.0×30 cm) and eluted with water-MeOH (4:6, 600 ml), MeOH (2 L), and acetone (2 L). 250 ml fractions were collected. The fractions were analyzed by HPLC and those with similar compositions were combined to produce 7 pools (CDXA-13-133 F1 to F7). The pool CDXA-13-133-F5 (22.5 g, 27.7% w/w of the extract) was found to contain the majority of the desired saponins.

This pool (22.0 g) was chromatographed on normal phase silica (445 g, Merck silica gel 60, 70-230 mesh, 0.0763 to 0.200 mm, 5.0×30 cm) and eluted with 3 L each of dichloromethane-MeOH-water systems of following compositions: a) 80:20:3, b) 75:25:3, c) 70:30:3, and d) 65:35:3. 250 ml fractions were collected, analyzed by HPLC and combined into 11 pools (CDXA-13-137-F1 to F11).

The fractions F6 and F7 were combined, dried (10.0 g, 45%) and chromatographed on C8 Silica (350 g, Phenomenex Luna C8(2), 5 micron, 100 A, 5.0×28 cm) and eluted with MeOH-water systems of following compositions: 4:6 (800 ml), b) 5:5 (2 L), c) 55:45 (5 L) 6:4 (1 L), d) 65:35 (1 L), e) 7:3 (1 L), f) 8:2 (1 L) and MeOH (1 L). The fractions were analyzed by HPLC and combined to give 29 pools (CDXA-13-138-F1 to F29). 250 ml fractions were collected.

Fractions F13 to F16 were dried (1.155 g, 11.6%) and purified by reverse phase HPLC using a Gilson semi preparative HPLC system consisting of a UV/Vis detector model 155, pump model 321, and liquid handler model 215.

Chromatographic Conditions:

| Column: | Phenomenex Luna C18(2), 5 micron, 150 × 21.2 mm |
|---|---|
| Mobile Phase: | Acetonitrile-Water (28:72) |
| Flow Rate: | 10 ml/min |
| Sample size: | 15 mg of each fraction per injection |
| Detection: | UV 205 nm |

Five peaks were collected, P1 to P5, and were identified by comparison of $^1$H, $^{13}$C NMR and Mass spectral data with those reported in the literature for trigoneoside IVa, its 25 (S) isomer-glycoside F. A further similar compound, compound 3 was detected. This compound has not been previously described.

NMR spectra were recorded in $d_5$ Pyridine. The proton spectra were recorded on a Varian Inova VXRs −300 instrument at 300 MHz and the carbon spectra were recoded on a Varian Inova 400 instrument at 100 MHz.

Mass spectra were recorded on a Finnigan LCQ Deca instrument in APCI mode.

Peak 1, Trigoneoside IVa: White solid (90 mg, 0.025 w/w of the seeds). NMR (pyridine-d5, 400 MHz, δ): 0.90 (3H, s, 18-H$_3$), 1.04 (3H, d, J=6.8 Hz, 27-H$_3$), 1.07 (3H, s, 19-H$_3$), 1.34 (3H, d, J=6.8 Hz, 21-H$_3$), 1.79 (3H, s, J=6.0 Hz, Rha-6"-H$_3$), 3.88 (1H, m, 3-H), 4.09 (2H, m, 16-H$_2$), 4.84 (1H, d, J=7.6 Hz, Glc-1''''-H), 4.97 (1H, overlapped, Glc-1'-H), 5.16 (1H, d, J=7.6 Hz, Glc-1'''-H), 5.29 (1H, d like, 6-H), 6.29 (1H, br s, Rha-1"-H).

Peak 2, Compound C/protodioscin: White solid (120 mg, 0.033%). $^1$H NMR (pyridine-d5, 400 MHz, δ): 0.90 (3H, s, 18-H$_3$), 1.04 (3H, d, J=6.8 Hz, 27-H$_3$), 1.07 (3H, s, 19-H$_3$), 1.34 (3H, d, J=6.8 Hz, 21-H$_3$), 1.66 (3H, s, J=6.0 Hz, Rha-6'''-H$_3$), 1.79 (3H, s, J=6.0 Hz, Rha-6"-H$_3$), 3.88 (1H, m, 3-H), 4.09 (2H, m, 16-H$_2$), 4.84 (1H, d, J=8.0 Hz, Glc-1''''-H), 4.97 (1H, overlapped, Glc-1'-H), 5.90 (1H, br s, Rha-1'''-H), 5.32 1H, d like, 6-H), 6.45 (1H, br s, Rha-1"-H).

Peak 3, Compound 3: White solid (30 mg, 0.008%). $^1$H NMR (pyridine-d5, 400 MHz, δ): 0.89 (3H, s, 18-H$_3$), 1.06 (3H, s, 19-H$_3$), 1.34 (3H, d, J=6.4 Hz, 21-H$_3$), 1.66 (3H, s, J=6.0 Hz, Rha-6"1-H$_3$), 1.79 (3H, s, J=6.0 Hz, Rha-6"-H$_3$), 3.88 (1H, m, 3-H), 4.84 (1H, d, J=8.0 Hz, Glc-1''''-H), 4.97 (1H, overlapped, Glc-1'-H), 5.32 1H, d like, 6-H), 5.90 (1H, br s, Rha-1'''-H), 6.45 (1H, br s, Rha-1"-H).

Peak 4, Glycoside F: White solid (120 mg, 0.033%). $^1$H NMR (pyridine-d5, 400 MHz, δ): 0.90 (3H, s, 18-H$_3$), 1.00 (3H, d, J=6.4 Hz, 27-H$_3$), 1.06 (3H, s, 19-H$_3$), 1.35 (3H, d, J=6.4 Hz, 21-H$_3$), 1.79 (3H, s, J=6.0 Hz, Rha-6-H$_3$), 3.88 (1H, m, 3-H), 3.97 (2H, m, 16-H$_2$), 4.84 (1H, d, J=7.6 Hz, Glc-1''''-H), 4.97 (1H, overlapped, Glc-1'-H), 5.16 (1H, d, J=7.6 Hz, Glc-1'''-H), 5.29 (1H, d like, 6-H), 6.29 (1H, br s, Rha-1''-H).

TABLE 8

Summary

| Compound ID | Name | Yield (mg) |
|---|---|---|
| F1 | Trigoneoside IVa | 90 mg |
| F2 | Compound C/Protodioscin | 120 mg |
| F3 | Compound 3 | 30 mg |
| F4 | Glycoside F | 120 mg |
| F5 | Trigonelloside C | 300 mg |

Chemical structures for the five compounds are given in FIG. 16.

Other Compounds

Shatavarin IV (FIG. 16) which can be isolated from *Asparagus racemosus* (Ravikumar P. R. Indian J. Chem. 26B, 1012-1017 (1987)) and protodioscin from *Tribulus terrestris* (but also isolatable from fenugreek as compound C of Yoshikawa M. et al., Heterocycles 47, 397-405 (1998)) were both supplied by Chromadex inc. 2952 S. Daimler St. Santa Ana Calif. Protodioscin was also isolated from the above preparation of fenugreek as peak 2 conforming to published NMR spectra of protodioscin.

12. Preparation and Purification of Dioscorea Radix Extracts

Extraction: Dried, powdered *Dioscorea radix* (6.2 Kg) was extracted three times with MeOH—H$_2$O (8:2, 36 L, 26 L and 24 L, respectively). The first extract (CDXA-13-148-1) was concentrated to 5 L by evaporation under vacuum. The second and third extracts (CDXA-13-148-2 and 13-148-3) were combined and concentrated to 3.3 L.

Fractionation: The concentrated extracts were loaded on to a Dianion HP20 column (2.7 Kg) in 2.0 L batches and eluted with H$_2$O and H$_2$O-MeOH (8:2, 6:4 and 4:6 and MeOH 1 L each). The column eluent was monitored by TLC and 8 fractions were collected (CDXA-13-149-1 to 8).

Column Chromatography 1: CDXA-13-149-4 and 13-149-5 were combined (45.4 g), absorbed on to silica gel (101 g), loaded on to a silica gel column (255 g) and eluted with EtOAc-MeOH—H$_2$O (80:20:3, 1.7 L; 75:25:3, 2.0 L; 70:30:4, 1.04 L; 65:35:4, 2.08 L; and 60:40:5, 1.05 L). The eluent was monitored by TLC and 26 fractions were collected (CDXA-13-166-F1 to F26).

Column Chromatography 2: CDXA-13-166-F14 to F22 were combined (25.2 g), absorbed on to silica gel (48.2 g), loaded on to a silica gel column (305 g), and eluted with EtOAc-MeOH—H$_2$O (80:20:3, 600 ml; 75:25:3, 4120 ml; 70:30:4, 2080 ml; 65:35:4, 1050 ml; and 60:40:5, 1050 ml). The eluent was monitored by TLC and 28 fractions were collected (CDXA-13-167-F1~F28).

Purification of Protogracillin: Fractions 13-167-F5 to F16 were combined and concentrated under vacuum, the white powder separated was filtered, dried (CDXA-13-167-K5, 2.27 g) and heated under refluxed in ACN—H$_2$O (28:72; 100 ml) at 90° C. oil bath overnight. The product was further purified by HPLC (Novaprep 5000 semi-preparative HPLC column (C18, 5.0×20.0 cm) eluted with ACN—H$_2$O (25:75) for 41.2 minutes then eluted with ACN—H$_2$O (50:50) for another 20 minutes at a flow rate of 100 ml/minute. Monitored at UV 205 nm and the major peak was collected) to give two batches of protogracillin (CDXA-13-168-1, 374 mg; CDXA-13-169-1, 552 mg).

Purification of dioscin and gracillin: Fraction CDXA-13-149-F6 (22.4 g) was loaded on to a C18 column (296 g, 5×20 cm), eluted with MeOH—H$_2$O (3:7, 4:6, 45:55, 50:50, 55:45, 60:40, 65:35, 7:3, 75:25, 80:20, 85:15 and 90:10, 1000 ml each), and 8 fractions were collected (CDXA-13-159-F1 to F8). Fraction CDXA-13-159-F7 (4.5 g) was separated on silica gel (257 g silica gel) eluting with EtOAc-MeOH—H$_2$O (85:15:2, 1020 ml; 80:20:3, 3090 ml; 75:25:3, 1030 ml) giving 14 fractions (CDXA-13-160-F1 to F14). The fractions CDXA-13-160-F2 and F3 gave dioscin (CDXA-13-160-1, 404 mg) while fraction CDXA-13-160-F4 gave gracillin (CDXA-13-160-2, 195 mg) both as white powders.

Protogracillin was 96.7% pure as a white powder
Gracillin was 90.8% pure as a white powder
Mass Spec and $^1$H NMR Data of the Compounds Isolated from Dioscorea:

Gracillin: (+) ESI-MS m/z 907.56 [M+Na$^+$]; $^1$H NMR (400 Hz, C$_5$D$_5$N) δ 0.69 (311, d, J=5.6 Hz, 27-H$_3$), 0.83 (3H, s, 18-H$_3$), 1.07 (3H, s, 19-H$_3$), 1.14 (3H, d, J=7.2 Hz, 21-H$_3$), 1.79 (3H, d, J=6.4 Hz, rha 6'-H$_3$), 4.96 (1H, d, J=7.2 Hz, glc 1-H), 5.12 (1H, d, J=7.6 Hz, glc 1''-H), 5.33 d, J=5.2 Hz, 6-H), 6.41 (1H, s, rha 1''-H).

Protogracillin: (+) ESI-MS m/z 1087.56 [M+Na$^+$]; $^1$H NMR (400 Hz, C$_5$D$_5$N) δ 0.91 (3H, s, 18-H$_3$), 1.00 (3H, d, J=6.4 Hz, 27-H$_3$), 1.08 (3H, s, 19-H$_3$), 1.35 (3H, d, J=6.8 Hz, 21-H$_3$), 1.78 (3H, s, J=6.0 Hz, Rha-6'-H$_3$), 4.84 (1H, d, J=7.6 Hz, Glc-1'''-H), 4.97 (1H, d, J=6.8 Hz, Glc-1'-H), 5.13 (1H, d, J=8.0 Hz, glc 1''-H), 5.33 (1H, d, J=4.0 Hz, 6-H), 6.42 (1H, s, Rha-1'-H).

Dioscin: (+) ESI-MS m/z 891.55 [M+Na$^+$]; $^1$H NMR (400 Hz, C$_5$D$_5$N) δ 0.70 (3H, d, J=4.8 Hz, 27-H$_3$), 0.84 (3H, s, 18-H$_3$), 1.06 (3H, s, 19-H$_3$), 1.15 (3H, d, J=6.8 Hz, 21-H$_3$), 1.66 (3H, d, J=4.8 Hz, rha 6''-H$_3$), 1.79 (3H, d, J=6.4 Hz, rha 6''-H$_3$), 4.97 (1H, d, J=6.8 Hz, glc 1-H), 5.31 (1H, d, J=4.0 Hz, 6-H), 5.91 (1H, s, rha 1''-H), 6.45 s, rha 1'-H).

TABLE 9

Approximate Ic$_{50}$ values (nM) for example compounds

| Compound | Number | Cell free assay | | Cell based assay |
|---|---|---|---|---|
| Protodioscin | 1 | 20 | ** | a |
| Pseudoprotodioscin | 2 | 35 | * | 50 |
| Dioscin | 11 | 40 | * | 75 |
| Trigoneoside IVa | 6 a | 0.9 | * | 75 |
| Glycoside F | 7 a | 5 | ** | b |
| Shatavarin I | 21 a | 1 | * | 0.75 |
| Shatavarin IV | 22 a | c | ** | † |
| Protogracillin | 1 b | 3 | * | 0.25 |
| Gracillin | 18 b | 4.5 | * | 2.5 |

\* Cell free assays were carried out on heart lysates of TNF-α mice as described above.
\*\* Cell free assays were carried out on heart lysates of BB rats as described above.
a 33% inhibition at 20 nM
b 100% inhibition at 22 nM n BB rat heart lysate
c 89% inhibition at 22 nM in BB rat heart lysate
† no activity detected at 22.5 nM

TABLE 10

Purity of compounds used

| Compound | Number | Purity |
|---|---|---|
| Protodioscin | 1a | 93.3% |
| Pseudoprotodioscin | 2a | 88.6% |
| Dioscin | 11a | 90.8% |

TABLE 10-continued

Purity of compounds used

| Compound | Number | Purity |
|---|---|---|
| Trigoneoside IVa | 6a | 89% |
| Glycoside F | 7a | 80.3% |
| Shatavarin I | 21a | >95% |
| Protogracillin | 1b | 98.8% |
| Gracillin | 18b | 98% |

Purity was determined by HPLC using UV absorption at 205 nm

Compound C (at 20 ng/ml) was found to inhibit Core 2 GlcNAc-T approximately 98.5% compared to controls, in TNF-α treated Human leukocytes (U937 cells). The sample of compound C was approximately 82.5% pure by HPLC at 205 nM The approximate $IC_{50}$ of Trigoneoside IVa was found to be between 0.25 nM and 0.9 nM in cell free systems. Further analysis of a sample prepared according to applicants co pending WO05/060977 indicates that it contains approximately 7.5% protodioscin and 9% Trigonelloside C (Yoshikawa et al., Heterocycles 47, 397-405 (1998)).

The $IC_{50}$ of Glycoside F was found to be approximately 5 nM. Further analysis of the preparation indicates that it contains a small amount of Trigonelloside C.

The $IC_{50}$ of Protodioscin (93.3% pure) produced as described in applicants co pending WO05/060977 was found to be approximately 20 nM. The sample contained 1.5% Trigoneoside Na. A sample prepared from *Tribulus terrestris* (Chromodex Inc. 2952 S. Daimler Street Santa Ana Calif. 92705), which was 97% pure, and had an NMR spectrum consistent with protodioscin, appeared to demonstrate no activity at concentrations of 50 μM. Thus Trigoneoside Na activity could account for at least some of the activity seen in the protodioscin sample prepared as per WO05/060977.

Trigonelloside C is similar to Protodioscin but is the opposite isomer at carbon 25. A preparation of this compound according to co pending WO05/060977 was 98.2% pure and contained no measurable quantity of other Core 2 GlcNAc-T inhibitors. A preparation of Trigonelloside C prepared according to WO05/060977 inhibited Core 2 GlcNAc-T 69% at 2.5 nM.

13. Determination of Core 2 GlcNAc-T Activity in Leukocytes Isolated from Patients Newly Diagnosed with MS Blood samples were taken from 4 patients newly diagnosed with active MS and 2 age matched healthy control subjects and placed in heparinised tubes. The blood sample was layered onto an equal volume of Histo-Paque 1077™ (Sigma, Poole, Dorset, UK). and centrifuged at 400 g for 30 mins. The Buffy coat (containing peripheral blood mononuclear cells (PBMNC) and polymorphonuclear (PMN) leukocytes) was washed in phosphate buffered saline. Isolated leukocytes were frozen and lysed in 0.9% NaCl 0.4% Triton-X100 1 mM PMSF and the Core 2 GlcNAc-T assayed. The reaction was performed in 50 mmol/l 2(N-morpholino) 2(N-morpholino) ethanesulfonic acid pH 7.0; 1 mmol/l UDP GlcNAc, 0.5 μCi UDP-6 [3H]-N-acetylglucosamine (16,000 dpm/nmol, NEN Life Science Products, Hounslow, U.K.); 0.1 mol/l GlcNAc; 1 mmol/l βDgal (1-3)Dα-GalNAc-p-nitrophenol and 15 μl cell lysate (100-200 μg protein) for a final volume of 30 μl. After incubating the mixture for 1 h at 37° C., the reaction was terminated by adding 1 ml of ice cold water and processed on a C18 Sep-Pak column (Waters-Millipore, Watford, U.K.). After washing the column with 20 ml water, the product was eluted with 5 ml methanol and radioactivity counted. Endogenous activity of core 2 transferase was measured in the absence of the added acceptor. The results are shown in FIGS. 20 and 21.

References

1. Hu K. et al Planta Medica, 63(2), 161-165 (1997).
2. Dong M. et al., Planta Med. 67(9):853-7 (2001).
Yoshikawa M. et al., Heterocycles 47, 397-405 (1998).
4. Akhov L. S. et al., J. Agric. Food Chem. 47(8), 3193-3196 (1999)
5. Mimaki Y. et al., *Chem Pharm Bull* (Tokyo). 46(11):1829-32 (1998).
6. Shimomura H. et al., Phytochemistry 28, 3163-3170 (1989).
7. Kawasaki T. et al., *Chemical & Pharmaceutical Bulletin,* 22(9), 2164-75 (1974).
8. On K. et al. *Phytochemistry.* 31(8):2767-75 (1992).
9. Mimaki Y. et al *Phytochemistry* 37(1):227-32 (1994).
10. Nakamura O. et al., *Phytochemistry.* 36(2):463-7 (1994).
11. Mimaki Y and Sasheda Y. Chem. Pharm. Bull. 38(11), 3055-9 (1990).
12. Sashida Y. et al., Chem. Pharm. Bull. 39(9), 2362-8 (1991)
13. Haladova M. et al., *Pharmazie,* 54(2), 159-160 (1999).
14. Sharma et al., Phytochemistry. 33(3):683-6. (1993).
15. Petit G. et al., Journal of natural products 54, 1491-1502.
16. Vasil'eva I. S. et al., *Appl. Biochem. Microbiol.* 31, 206-209 (1995).
17. Vasil'eva I. et al., *Prikl Biokhim Mikrobiol.* 20(3):404-6 (1984).
18. Joshi J. et al., Indian J. Chem. 27B, 12-16 (1988).
19. Ravikumar P. R. et al., Indian J. Chem. 26B, 1012-1017 (1987).
20. Yang D. et al *Journal of Agricultural and Food Chemistry,* 51(22), 6438-6444 (2003).
21. Aquino R. et al *J. Nat. Products* 49(2) 1096-1101 (1986).
22. Tomova M. et al *Int Conf. Chem. Biotechnol.* 3, (1) 298-302.
23. Liu H. W. et al *J Asian Nat Prod Res.* 5(4):241-247 (2003).
24. Sang S. *Phytochemistry,* 52(8), 1611-1615 (1999).
25. Zheng Q. et al *Steroids,* 69(2), 111-119 (2004).
26. Hernandez, J. C. *Bioorganic & Medicinal Chemistry* 12(16), 4423-4429 (2004).
27. Inoue T. et al *Phytochemistry* 40(2), 521-5 (1995).
28. Tsukamoto T and Kawasaki T. *Pharm Bull* 4(2):104-8 (1956).
29. Chen C. et al *Yunnan Zhiwu Yanjiu,* 9(4), 495-502 (1987).
30. Tang S. et al *Yunnan Zhiwu Yanjiu,* 9(2), 233-8 (1987).
31. Kintya P. (Translation of *Khimiya Prirodnykh Soedinenii*), [Volume Date 1997], 33(6), 658-662 (1998).
32. Yin F. et al *J. Nat. Products,* 67(6), 942-952 (2004).
33. Fujita S. et al *Phytochemistry,* 38(2), 465-72 (1995).
34. Yoshikawa K et al. *Chemical & Pharmaceutical Bulletin,* 40(9), 2287-91 (1992).
35. Yoshikawa K. et al *Chemical & Pharmaceutical Bulletin,* 40(9), 2275-8 (1992).
36. Renault J. et al, *Phytochemistry,* 44(7), 1321-1327 (1997).
37. Mimaki Y. et al *Phytochemistry.* 33(3):675-82 (1993).
38. Liu C. et al. *Yaoxue Xuebao,* 18(8), 597-606 (1983).
39. Chen C. et al *Yunnan Zhiwu Yanjiu,* 6(1), 111-17 (1984).

TABLE 11

13C NMR data of Peaks 1 to 5 (in pyridine-d5, 100 MHz) of example

| Carbon | Peak 1 | 2 | 3 | 4 | 5 |
|---|---|---|---|---|---|
| 1 | 37.5 | 38 | 38 | 38 | 38 |
| 2 | 30.1 | 30.7 | 30.7 | 30.6 | 30.7 |
| 3 | 78.1 | 78.6 | 78.6 | 78.6 | 78.6 |
| 4 | 38.9 | 39.4 | 39.5 | 39.4 | 39.5 |
| 5 | 140.7 | 141.2 | 141.3 | 141.2 | 141.2 |
| 6 | 121.8 | 122.4 | 122.4 | 122.4 | 122.4 |
| 7 | 32.3 | 32.9 | 32.9 | 32.7 | 32.8 |
| 8 | 31.7 | 32.2 | 32.2 | 32.2 | 32.2 |
| 9 | 50.3 | 50.8 | 50.9 | 50.8 | 50.8 |
| 10 | 37.1 | 37.6 | 37.6 | 37.6 | 37.6 |
| 11 | 21.1 | 21.6 | 21.6 | 21.6 | 21.6 |
| 12 | 39.9 | 40.4 | 40.4 | 40.4 | 40.4 |
| 13 | 40.8 | 41.3 | 41.3 | 41.3 | 41.3 |
| 14 | 56.6 | 57.1 | 57.1 | 57.1 | 57.1 |
| 15 | 32.5 | 33 | 33 | 32.8 | 33 |
| 16 | 81.1 | 81.6 | 81.6 | 81.6 | 81.6 |
| 17 | 63.8 | 64.3 | 64.3 | 64.3 | 64.3 |
| 18 | 16.5 | 17 | 17 | 17 | 17 |
| 19 | 19.4 | 19.9 | 20 | 19.9 | 19.9 |
| 20 | 40.7 | 41.2 | 41.2 | 41.2 | 41.2 |
| 21 | 16.5 | 17 | 17 | 17 | 17 |
| 22 | 110.7 | 111.2 | 111.2 | 111.2 | 111.2 |
| 23 | 37.1 | 37.6 | 37.7 | 37.7 | 37.7 |
| 24 | 28.3 | 28.8 | 28.9 | 28.9 | 28.9 |
| 25 | 34.4 | 34.9 | 35 | 34.8 | 34.8 |
| 26 | 75.4 | 75.9 | 75.9 | 75.8 | 75.8 |
| 27 | 17.4 | 18 | 18 | 18 | 18 |
| G1' | 100 | 100.5 | 100.8 | 100.5 | 100.8 |
| G2' | 77.3 | 77.8 | 78.5 | 77.7 | 78.4 |
| G3' | 76.2 | 76.7 | 78.3 | 76.6 | 78.2 |
| G4' | 81.9 | 82.5 | 78.8 | 82.5 | 78.9 |
| G5' | 77.7 | 78.2 | 77.4 | 78.2 | 77.4 |
| G6' | 62.1 | 62.5 | 61.8 | 62.5 | 61.7 |
| rha1" | 101.8 | 102.3 | 102.6 | 102.3 | 102.5 |
| rha2" | 72.4 | 73 | 73.1 | 73 | 73 |
| rha3" | 72.7 | 73.3 | 73.3 | 73.3 | 73.3 |
| rha4" | 74.1 | 74.6 | 74.6 | 74.6 | 74.6 |
| rha5" | 69.5 | 70 | 70.1 | 70 | 70 |
| rha6" | 18.7 | 19.2 | 19.2 | 19.2 | 19.2 |
| glc1/rha1''' | 105.2 | 105.7 | 103.4 | 105.7 | 103.4 |
| glc2/rha2''' | 75 | 75.5 | 73.1 | 75.5 | 73 |
| glc3/rha3''' | 78.4 | 79 | 73.2 | 79 | 73.2 |
| glc4/rha4''' | 71.2 | 71.7 | 74.4 | 71.7 | 74.4 |
| glc5/rha5''' | 78.2 | 78.7 | 70.9 | 78.8 | 70.9 |
| glc6/rha6''' | 61.8 | 62.3 | 19 | 62.3 | 19 |
| 26-O-G1'''' | 105.1 | 105.7 | 105.7 | 105.4 | 105.4 |
| G2'''' | 75.2 | 75.7 | 75.7 | 75.7 | 75.7 |
| G3'''' | 78.6 | 79.1 | 79 | 79.1 | 79.1 |
| G4'''' | 71.6 | 72.1 | 72.1 | 72.1 | 72.1 |
| G5'''' | 78.4 | 79 | 79 | 79 | 79 |
| G6'''' | 62.8 | 63.3 | 63.3 | 63.3 | 63.3 |

TABLE 12

13C NMR data of the compounds from *Dioscorea* (in pyridine-d5)

| | Gracillin 13-160-2 | Dioscin 13-160-1 | Protogracillin 13-168-1 |
|---|---|---|---|
| 1 | 37.8 | 37.8 | 37.8 |
| 2 | 30.4 | 30.5 | 30.4 |
| 3 | 78.3 | 78.4 | 78.9 |
| 4 | 39.0 | 39.3 | 39.0 |
| 5 | 141.1 | 141.1 | 141.1 |
| 6 | 122.1 | 122.2 | 122.3 |
| 7 | 32.7 | 32.6 | 32.7 |
| 8 | 32.1 | 32.0 | 32.0 |
| 9 | 50.6 | 50.6 | 50.6 |
| 10 | 37.5 | 37.5 | 37.5 |
| 11 | 21.4 | 21.4 | 21.4 |
| 12 | 40.2 | 40.2 | 40. |
| 13 | 40.8 | 40.8 | 41.1 |
| 14 | 57.0 | 56.9 | 56.9 |
| 15 | 32.6 | 32.5 | 32.8 |
| 16 | 81.4 | 81.4 | 81.5 |
| 17 | 63.2 | 63.2 | 64.2 |
| 18 | 16.7 | 16.7 | 16.8 |
| 19 | 19.7 | 19.7 | 19.7 |
| 20 | 42.3 | 42.3 | 41.0 |
| 21 | 15.4 | 15.4 | 16.8 |
| 22 | 109.6 | 109.6 | 111.0 |
| 23 | 32.0 | 32.1 | 37.6 |
| 24 | 29.6 | 29.6 | 28.7 |
| 25 | 30.9 | 30.9 | 34.6 |
| 26 | 67.2 | 67.2 | 75.6 |
| 27 | 17.7 | 17.7 | 17.8 |
| 3-O- | | | |
| Glc1 | 100.3 | 100.6 | 100.3 |
| 2 | 78.0 | 78.4 | 78.0 |
| 3 | 89.9 | 78.1 | 89.9 |
| 4 | 69.9 | 78.8 | 69.9 |
| 5 | 77.3 | 77.3 | 77.3 |
| 6 | 62.7 | 61.6 | 62.7 |
| Rha1' | 102.6 | 102.4 | 102.6 |
| 2' | 72.8 | 72.9 | 72.8 |
| 3' | 73.1 | 73.2 | 73.1 |
| 4' | 74.4 | 74.5 | 74.5 |
| 5' | 69.9 | 69.9 | 69.9 |
| 6' | | 18.9 | 19.1 |
| Glc1/rha1" | 104.9 | 103.2 | 104.9 |
| 2" | 75.3 | 72.9 | 75.3 |
| 3" | 79.0 | 73.1 | 78.9 |
| 4" | 71.8 | 74.2 | 71.8 |
| 5" | 78.9 | 70.7 | 78.9 |
| 6" | 62.7 | 19.0 | 62.8 |
| 26-O- | | | |
| Glc1''' | | | 105.3 |
| 2''' | | | 75.6 |
| 3''' | | | 79.1 |
| 4''' | | | 72.0 |
| 5''' | | | 79.0 |
| 6''' | | | 63.1 |

The invention claimed is:

1. A method of diagnosing Multiple Sclerosis in a subject comprising comparing the level of Core 2 GlcNAc-T activity associated with samples isolated from the subject with the level of Core 2 GlcNAc-T activity determined in samples isolated from healthy non afflicted individuals, a level of Core 2 GlcNAc-T activity higher than that in samples isolated from healthy non afflicted individuals being indicative that the subject is afflicted with MS.

2. A method according to claim 1 wherein a level of Core 2 GlcNAc-T activity associated with samples isolated from the subject that is least 2 times higher than that in samples isolated from healthy non afflicted individuals is indicative of MS in the subject.

3. A method according to claim 1 in which the samples isolated from the subject are biopsy samples or blood samples.

4. A method according to claim 1 in which the samples isolated from the subject are leukocytes.

5. A method of determining the utility of a substance for use in the treatment of Multiple Sclerosis comprising measuring the ability of the substance to inhibit the activity of Core 2 GlcNAc-T.

* * * * *